(12) United States Patent
Ban et al.

(10) Patent No.: US 10,975,358 B2
(45) Date of Patent: Apr. 13, 2021

(54) METHOD FOR IMPROVING EFFICIENCY OF INDUCING PLURIPOTENT STEM CELL

(71) Applicant: ID PHARMA CO., LTD., Tokyo (JP)

(72) Inventors: Hiroshi Ban, Ibaraki (JP); Akihiro Iida, Ibaraki (JP); Mamoru Hasegawa, Ibaraki (JP)

(73) Assignee: ID Pharma Co., Ltd., Tokyo (JP)

( * ) Notice: Subject to any disclaimer, the term of this patent is extended or adjusted under 35 U.S.C. 154(b) by 0 days.

(21) Appl. No.: 15/023,484

(22) PCT Filed: Sep. 24, 2014

(86) PCT No.: PCT/JP2014/075248
§ 371 (c)(1),
(2) Date: Mar. 21, 2016

(87) PCT Pub. No.: WO2015/046229
PCT Pub. Date: Apr. 2, 2015

(65) Prior Publication Data
US 2016/0215270 A1 Jul. 28, 2016

(30) Foreign Application Priority Data
Sep. 24, 2013 (JP) .............................. JP2013-197308

(51) Int. Cl.
*C12N 5/074* (2010.01)
*A61K 35/545* (2015.01)
*C12N 7/00* (2006.01)

(52) U.S. Cl.
CPC .......... *C12N 5/0696* (2013.01); *A61K 35/545* (2013.01); *C12N 7/00* (2013.01); *C12N 2501/602* (2013.01); *C12N 2501/603* (2013.01); *C12N 2501/604* (2013.01); *C12N 2501/606* (2013.01); *C12N 2506/09* (2013.01); *C12N 2510/00* (2013.01); *C12N 2523/00* (2013.01); *C12N 2760/18843* (2013.01); *C12N 2830/00* (2013.01); *C12N 2840/00* (2013.01)

(58) Field of Classification Search
None
See application file for complete search history.

(56) References Cited

U.S. PATENT DOCUMENTS

| | | | |
|---|---|---|---|
| 9,090,909 B2 | 7/2015 | Ban et al. | |
| 9,127,256 B2 | 9/2015 | Fusaki et al. | |
| 2011/0287538 A1 | 11/2011 | Fusaki et al. | |
| 2013/0029423 A1 | 1/2013 | Yamanaka et al. | |
| 2013/0210150 A1 | 8/2013 | Ban et al. | |
| 2015/0337334 A1 | 11/2015 | Fusaki et al. | |

FOREIGN PATENT DOCUMENTS

| | | | |
|---|---|---|---|
| CN | 102159710 A | 8/2011 | |
| CN | 103189508 A | 7/2013 | |
| EP | 1437593 A1 | 7/2004 | |
| EP | 2612911 A1 | 7/2013 | |
| JP | WO2012/029770 | * 3/2012 | ............. C12N 15/09 |
| JP | 2013-519371 A | 5/2013 | |
| WO | WO 03/025570 A1 | 3/2003 | |
| WO | WO-2010/008054 A1 | 1/2010 | |
| WO | WO-2011/102531 A1 | 8/2011 | |
| WO | WO-2012/029770 A1 | 3/2012 | |

OTHER PUBLICATIONS

U.S. Appl. No. 15/063,929, Fusaki et al.
Ban et al., "Efficient generation of transgene-free human induced pluripotent stem cells (iPSCs) by temperature-sensitive Sendai virus vectors," Proc Natl Acad Sci USA. 108(34):14234-9 (2011).
Kawaguchi et al., "Yori Shinpo shita Taisaibo Reprogramming-ho: Sendai Virus Vector (CytoTune-iPS) ni yoru Shinpo," ("The novel cell reprogramming method using Sendai virus vectors (CytoTune-iPS") The Cell. 46(5):29-30 (2014).
Lowry et al., "Generation of human induced pluripotent stem cells from dermal fibroblasts," Proc Natl Acad Sci USA. 105(8):2883-8 (2008).
Maherali et al., "Directly reprogrammed fibroblasts show global epigenetic remodeling and widespread tissue contribution," Cell Stem Cell. 1:55-70 (2007) (38 pages, including supplemental data).
Masaki et al., "Heterogeneity of pluripotent marker gene expression in colonies generated in human iPS cell induction culture," Stem Cell Res. 1(2):105-15 (2008) (11 pages).
Okita et al., "Generation of germline-competent induced pluripotent stem cells," Nature. 448(7151):313-7 (2007) (6 pages).
Okita et al., "Generation of mouse induced pluripotent stem cells without viral vectors," Science. 322(5903):949-53 (2008).
Park et al., "Reprogramming of human somatic cells to pluripotency with defined factors," Nature. 451(7175):141-6 (2008).
Stadtfeld et al., "Induced pluripotent stem cells generated without viral integration," Science. 322(5903):945-9 (2008).
Takahashi et al., "Induction of pluripotent stem cells from mouse embryonic and adult fibroblast cultures by defined factors," Cell. 126(4):663-76 (2006) (55 pages, including supplemental data).
Takahashi et al., "Induction of pluripotent stem cells from adult human fibroblasts by defined factors," Cell. 131(5):861-72 (2007).

(Continued)

Primary Examiner — Arthur S Leonard
(74) Attorney, Agent, or Firm — Clark & Elbing LLP

(57) ABSTRACT

The present invention provides methods for improving the efficiency of inducing pluripotent stem cells, as well as vectors and compositions for use therein. In the induction of pluripotent stem cells which contains the step of introducing a vector that contains the KLF gene, OCT gene, and SOX gene in this order, the efficiency of pluripotent stem cell induction was successfully increased significantly by further introducing a vector that contains the KLF gene but not the OCT gene and the SOX gene. The methods of the present invention have an excellent feature in that they allow efficient induction of pluripotent stem cells under a temperature condition closer to the physiological environment, and prompt vector removal after the pluripotent stem cell induction. The present invention enables more efficient induction of pluripotent stem cells.

3 Claims, 29 Drawing Sheets

Specification includes a Sequence Listing.

(56) References Cited

OTHER PUBLICATIONS

Wernig et al., "In vitro reprogramming of fibroblasts into a pluripotent ES-cell-like state," Nature. 448(7151):318-24 (2007) (8 pages).
Yu et al., "Induced pluripotent stem cell lines derived from human somatic cells," Science. 318(5858):1917-20 (2007).
Yu et al., "Human induced pluripotent stem cells free of vector and transgene sequences," Science. 324(5928):797-801 (2009) (7 pages).
Zhou et al., "Adenoviral gene delivery can reprogram human fibroblasts to induced pluripotent stem cells," Stem Cells. 27(11):2667-74 (2009).
International Search Report for International Patent Application No. PCT/JP2014/075248, dated Dec. 22, 2014 (English language translation provided) (6 pages).
Written Opinion of the International Searching Authority for International Patent Application No. PCT/JP2014/075248, dated Dec. 22, 2014 (English language translation provided) (10 pages).
International Preliminary Report on Patentability for International Patent Application No. PCT/JP2014/075248, dated Mar. 29, 2016 (English language translation provided) (12 pages).
Bernal, "RNA-based tools for nuclear reprogramming and lineage-conversion: towards clinical applications," J Cardiovasc Transl Res. 6(6):956-68 (2013).
Fujie et al., "New type of Sendai virus vector provides transgene-free IPS cells derived from chimpanzee blood," PLoS One. 9(12):e113052 (2014) (19 pages).
Ye et al., "Blood cell-derived induced pluripotent stem cells free of reprogramming factors generated by Sendai viral vectors," Stem Cells Transl Med. 2(8):558-66 (2013).
Extended European Search Report for European Patent Application No. 14847286.3, dated Feb. 3, 2017 (8 pages).

\* cited by examiner

CONDITION 1

CONDITION 2

CONDITION 3

CONDITION 4

CONDITION 5

CONDITION 6

CONDITION 1

CONDITION 2

CONDITION 3

CONDITION 4

CONDITION 5

CONDITION 6

METHOD FOR IMPROVING EFFICIENCY OF INDUCING PLURIPOTENT STEM CELL

TECHNICAL FIELD

The present invention relates to methods for improving efficiency of the induction of pluripotent stem cells. Furthermore, the present invention relates to gene delivery vectors and gene delivery compositions for use in the induction of pluripotent stem cells, and uses thereof. Specifically, the present invention relates to techniques for enhancing the efficiency of inducing pluripotent stem cells, in the induction of pluripotent stem cells which contains the step of introducing a vector that contains the KLF gene, OCT gene and SOX gene in one vector in this order.

BACKGROUND ART

Since the reported induction of pluripotent stem cells (induced pluripotent stem (iPS) cells; also called as "artificial pluripotent stem cells" or "induced pluripotent stem cells") from somatic cells (Non-Patent Document 1), iPS cells have been produced by introducing reprogramming factors into various mammalian cells including human and mouse cells (Non-Patent Documents 1 to 9). Many of them use retrovirus vectors to introduce reprogramming factors. However, since retrovirus vectors carry the risk of tumorigenesis as a result of integration into the host genome, their use is limited (Non-Patent Document 3). To solve this problem, attempts of inducing iPS cells using adenovirus vectors or plasmids have been made, but as long as DNA-type vectors are used, it is impossible to completely remove concerns over integration into the genome. Furthermore, the induction efficiency of iPS cells by these vectors is extremely low (Non-Patent Documents 10 to 13).

To solve these problems, the present inventors have previously developed a system for inducing iPS cells using a Sendai virus vector which is an RNA-type virus (Patent Documents 1 and 2). Induction efficiency of iPS cells using the Sendai virus vector was significantly higher than that in previous cases using other vectors. Since the Sendai virus vectors do not have a DNA phase during their lifecycle, and therefore there is no concern that they will become integrated into the host genome, they are excellent in terms of safety. Also, the vectors can be easily removed after induction of iPS cells. However, techniques of the present invention for further increasing the induction efficiency of iPS cells are not known.

PRIOR ART DOCUMENTS

Patent Documents

[Patent Document 1] International Publication No. WO 2010/008054
[Patent Document 2] International Publication No. WO 2012/029770

Non-Patent Documents

[Non-Patent Document 1] Takahashi, K. and Yamanaka, S. (2006) Cell 126, 663-676
[Non-Patent Document 2] Maherali, et al., (2007) Cell Stem Cell 1, 55-70
[Non-Patent Document 3] Okita, K. et al., (2007) Nature 448, 313-317
[Non-Patent Document 4] Wernig, M. et al., (2007) Nature 448, 318-324
[Non-Patent Document 5] Takahashi, K. et. al., (2007) Cell 131, 861-872
[Non-Patent Document 6] Yu, et al., (2007) Science 318, 1917-1920
[Non-Patent Document 7] Lowry, W. E. et al., (2008) Proc. Natl. Acad. Sci. USA 105, 2883-2888
[Non-Patent Document 8] Park, I. H. et al., (2008) Nature 451, 141-146
[Non-Patent Document 9] Masaki, H. et al., (2008) Stem Cell Res. 1, 105-115
[Non-Patent Document 10] Stadtfeld, M. et al., (2008) Science 322, 945-949
[Non-Patent Document 11] Okita, K. et al., (2008) Science 322, 949-953
[Non-Patent Document 12] Yu, J. et al., (2009) Science 324, 797-801
[Non-Patent Document 13] Zhou, W. et al., (2009) stem cells 27, 2667-2674

SUMMARY OF THE INVENTION

Problems to be Solved by the Invention

The present invention relates to methods for improving efficiency of the induction of pluripotent stem cells. Furthermore, an objective of the present invention is to provide gene delivery vectors and gene delivery compositions for use in the induction of pluripotent stem cells, and uses thereof. Specifically, an objective of the present invention is to provide methods for enhancing the efficiency of inducing pluripotent stem cells, and gene delivery vectors and compositions for use therein, in the induction of pluripotent stem cells which comprises the step of introducing a vector that comprises in one vector the KLF gene, OCT gene and SOX gene in this order.

Means for Solving the Problems

The present inventors searched for methods for further enhancing the efficiency of inducing pluripotent stem cells in the induction of pluripotent stem cells which comprises the step of introducing a vector that comprises in one vector the KLF gene, OCT gene and SOX gene in this order (i.e., reprogramming factors). In particular, when a temperature-sensitive vector is used as this vector to induce pluripotent stem cells, although pluripotent stem cells are induced with a relatively high efficiency if cultured at a low temperature (36° C.) after vector introduction, the induction efficiency of pluripotent stem cells may be significantly reduced if they are cultured at the standard cell culture temperature of 37° C. While the temperature-sensitive vector is superior in that the vector may be promptly removed after induction of pluripotent stem cells, the problem is that it is necessary to culture at a low temperature after vector introduction in order to efficiently induce such pluripotent stem cells.

The present inventors conducted dedicated research on methods that can induce pluripotent stem cells with high efficiency, by using a temperature-sensitive Sendai virus vector and not culturing at a low temperature after vector introduction. As a result, it was discovered that it is possible to significantly increase the efficiency of pluripotent stem cell induction in the introduction of a vector that comprises in one vector the KLF gene, OCT gene and SOX gene in this order without culturing at a low temperature, by further introducing a vector that comprises the KLF gene but not the OCT gene and the SOX gene. Specifically, compared with when a vector comprising the KLF gene, OCT gene and SOX gene in one vector in this order is used in combination with only a vector expressing the MYC gene, iPS cells can be induced with remarkably high efficiency without low-temperature culturing by further combining these vectors with a vector that comprises the KLF gene but not the OCT gene and the SOX gene.

This allows high-efficiency induction of pluripotent stem cells without low-temperature cell culturing, and establishment of a system of rapid vector removal after induction of pluripotent stem cells.

That is, the present invention relates to methods of enhancing the efficiency of inducing pluripotent stem cells, and gene delivery vectors and compositions and such for use therein, in the induction of pluripotent stem cells which contains the step of introducing a vector that contains in one vector the KLF gene, OCT gene, and SOX gene in this order, and more specifically to inventions described in each of the claims. Inventions consisting of any combination of two or more inventions described in claims that cite the same claim are also inventions intended herein. More specifically, the present invention relates to the following:

[1] a method of improving efficiency of pluripotent stem cell induction in a method of inducing pluripotent stem cells without low-temperature culturing, which introduces a temperature-sensitive Sendai virus vector that comprises in one vector the KLF gene, OCT gene, and SOX gene in this order, wherein the method comprises further introducing a Sendai virus vector that comprises the KLF gene but not the OCT aerie and the SOX gene;

[2] the method of [1], wherein the culturing is carried out at about 37° C.;

[3] the method of [1] or [2], wherein the temperature-sensitive Sendai virus vector comprising in one vector the KU gene, OCT gene, and SOX gene in this order is an F gene-deleted Sendai virus vector that comprises G69E, T116A, and A183S mutations in the M protein, A262T, G264R, and K461G mutations in the HN protein, D433A, R434A, K437A, and L511F mutations in the P protein, and N1197S and K1795E mutations in the L protein;

[4] the method of any one of [1] to [3], wherein the Sendai virus vector that comprises the KLF gene but not the OCT aerie and the SOX gene is an F gene-deleted Sendai virus vector that comprises G69E. T116A, and A183S mutations in the M protein, A262T, G264R, and K461G mutations in the HN protein, L511F mutation in the P protein, and N1197S and K1795E mutations in the L protein;

[5] the method of any one of [1] to [4], which further comprises introducing a temperature-sensitive Sendai virus vector inserted with a MYC gene;

[6] the method of [5], wherein the MYC gene-inserted temperature-sensitive Sendai virus vector is an F gene-deleted Sendai virus vector that comprises G69E, T116A, and A183S mutations in the M protein, A262T, G264R, and K461G mutations in the HN protein, D433A, R434A, K437A, and L511F mutations in the P protein, and L1361C, L1558I, N1197S, and K1795E mutations in the L protein;

[7] use of a Sendai virus vector that comprises the KLF gene but not the OCT gene and the SOX gene in the manufacture of a pharmaceutical for improving efficiency of pluripotent stem cell induction in a method of inducing pluripotent stem cells without low-temperature culturing, which introduces a temperature-sensitive Sendai virus vector that comprises in one vector the KLF gene, OCT gene, and SOX gene in this order;

[8] the use of [7], wherein the method of inducing pluripotent stem cells is a method which involves culturing at about 37° C.;

[9] the use of [7] or [8], wherein the temperature-sensitive Sendai virus vector comprising in one vector the KLF gene, OCT gene, and SOX gene in this order is an F gene-deleted Sendai virus vector that comprises G69E, T116A, and A183S mutations in the M protein, A262T, G264R, and K461G mutations in the HN protein, D433A, R434A, K437A, and L511F mutations in the P protein, and N1197S and K1795E mutations in the L protein;

[10] the use of any one of [7] to [9], wherein the Sendai virus vector that comprises the KLF gene but not the OCT gene and the SOX gene is an F gene-deleted Sendai virus vector that comprises G69E, T116A, and A183S mutations in the M protein, A262T, G264R, and K461G mutations in the HN protein, L511F mutation in the P protein, and N1197S and K1795E mutations in the L protein;

[11] a composition for inducing pluripotent stem cells, wherein the composition comprises:
(a) a temperature-sensitive Sendai virus vector that comprises in one vector the KLF gene, OCT gene, and SOX gene in this order, and
(b) a Sendai virus vector that comprises the KLF gene but not the OCT gene and the SOX gene;

[12] a composition for inducing pluripotent stem cells, wherein the composition comprises:
(a) a temperature-sensitive Sendai virus vector comprising in one vector the KLF gene, OCT gene and SOX gene in this order, which is F gene-deleted Sendai virus vector that comprises G69E, T116A and A183S mutations in the M protein, A262T, G264R and K461G mutations in the HN protein, D433A, R434A, K437A and L511F mutations in the P protein, and N1197S and K1795E mutations in the L protein; and
(b) a Sendai virus vector comprising the KLF gene but not the OCT gene and the SOX gene, which is an F gene-deleted Sendai virus vector that comprises G69E, T116A and A183S mutations in the M protein, A262T, G264R and K461G mutations in the HN protein, L511F mutation in the P protein, and N1197S and K1795E mutations in the protein;

[13] the composition of [11] or [12], which further comprises a temperature-sensitive Sendai virus vector inserted with a MYC gene;

the composition of [13], wherein the MYC gene-inserted temperature-sensitive Sendai virus vector is an F gene-deleted Sendai virus vector that comprises G69E, T116A, and A183S mutations in the M protein, A262T, G264R, and K461G mutations in the HN protein, D433A, R434A, K437A, and L511F mutations in the P protein, and L1361C, L1558I, N1197S, and K1795E mutations in the L protein;

[15] the composition of any one of [11] to [14], which is a composition for inducing pluripotent stem cells by culturing without low-temperature culturing;

[16] a kit for inducing pluripotent stem cells, wherein the kit comprises:
(a) a temperature-sensitive Sendai virus vector that comprises in one vector the KLF gene, OCT gene, and SOX gene in this order, and
(b) a Sendai virus vector that comprises the KLF gene but not the OCT gene and the SOX gene;

[17] a kit for inducing pluripotent stem cells, wherein the kit comprises:
(a) a temperature-sensitive Sendai virus vector comprising in one vector the KLF gene, OCT gene, and SOX gene in this order, which is an F gene-deleted Sendai virus vector that comprises G69E, T116A, and A183S mutations in the M protein, A262T, G264R, and K461G mutations in the HN protein, D433A, R434A, K437A, and L511F mutations in the P protein, and N1197S and K1795E mutations in the L protein; and
(b) a Sendai virus vector comprising the KLF gene but not the OCT gene and the SOX gene, which is an F gene-deleted Sendai virus vector that comprises G69E, T116A, and A183S mutations in the M protein, A262T, G264R, and K461G mutations in the HN protein, L511F mutation in the P protein, and N1197S and K1795E mutations in the L protein;
[18] the kit of [16] or [17], which further comprises a temperature-sensitive Sendai virus vector inserted with a MYC gene;
the kit of [18], wherein the MYC gene-inserted temperature-sensitive Sendai virus vector which is an F gene-deleted Sendai virus vector that comprises G69E, T116A and A183S mutations in the M protein, A262T, G264R and K461G mutations in the HN protein, D433A, R434A, K437A and L511F mutations in the P protein, and L1361C, L1558I, N1197S and K1795E mutations in the L protein; and
[20] the kit of any one of [16] to [19], which is a kit for inducing pluripotent stem cells by culturing without low-temperature culturing.

Any matters of the inventions described herein and any combination thereof are intended herein. In these inventions, inventions excluding any matters described herein, or any combinations thereof are also intended herein. Furthermore, certain specific embodiments described herein regarding the present invention not only disclose these embodiments, but also disclose inventions excluding these embodiments from generic inventions disclosed herein which include these embodiments.

Effects of the Invention

The present invention enables significant improvement of the efficiency of pluripotent stem cell induction using a vector that contains the KLF gene, OCT gene, and SOX gene in this order. Specifically, it is useful that pluripotent stem cells can be induced with high efficiency without low-temperature culturing, and use of a temperature-sensitive vector enables prompt removal of the vector after the induction of pluripotent stem cells.

BRIEF DESCRIPTION OF THE DRAWINGS

FIG. 10 shows a karyotype analysis of the induced artificial pluripotent stem cells.

FIG. 26 shows induction of iPS cells from human monocytes (appearance of cells of Donor 3).

MODE FOR CARRYING OUT THE INVENTION

Figure 1:
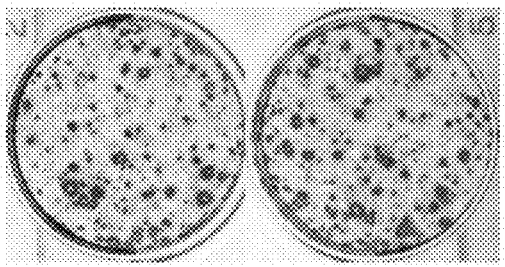
FIG. 1 shows the induction efficiency of alkaline phosphatase-positive iPS-like cells. Alkaline phosphatase-staining images of the vector-infected human neonatal foreskin-derived fibroblasts (BJ) on day 28 are shown.
Figure 1:
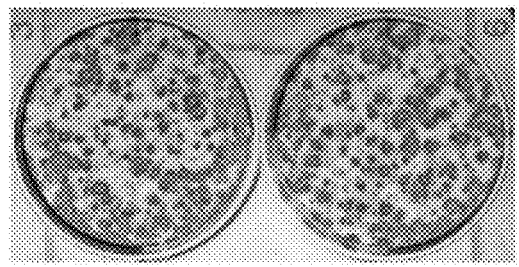
Figure 1:
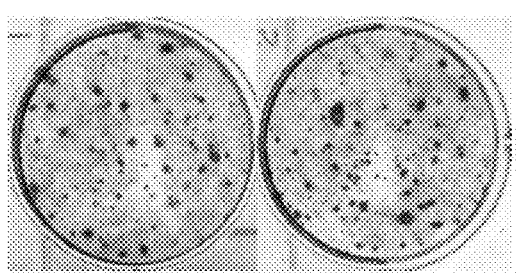
Figure 1:
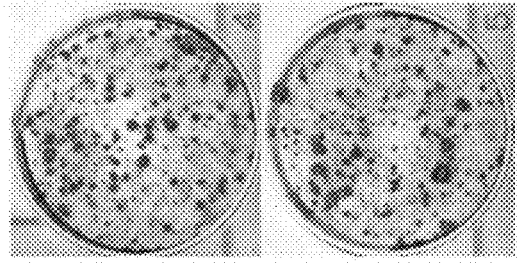
Figure 1:
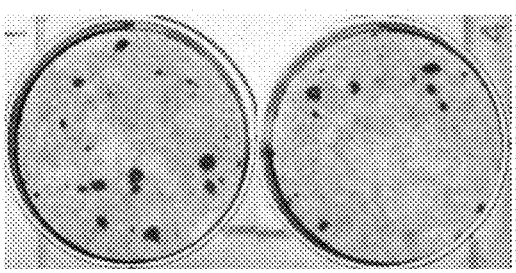
Figure 1:
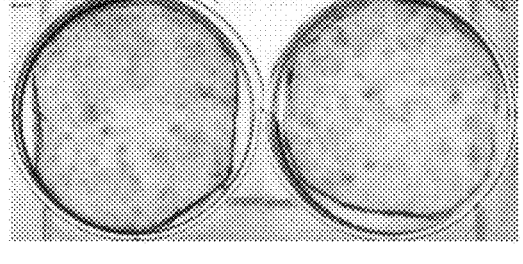

Hereinafter, the mode for carrying out the present invention will be described in detail.

The present invention relates to methods for increasing the efficiency of pluripotent stem cell induction, which comprise the step of introducing a vector that contains the KLF gene but not the OCT gene and the SOX gene in pluripotent stem cell induction that comprises the step of introducing a vector containing in one vector the KLF gene, OCT gene, and SOX gene in this order. More specifically, the methods of the present invention are methods of improving the efficiency of pluripotent stem cell induction in methods that induce pluripotent stem cells by introducing a temperature-sensitive virus vector containing the KLF gene, OCT gene, and SOX gene in this order in one vector, and which comprise the step of further introducing a virus vector that contains the KLF gene but not the OCT gene and the SOX gene.

After vector introduction, it is not necessary to culture at a low temperature (for example, under 36.5° C. and more specifically, for example, 36° C. or lower). That is, with the use of a temperature-sensitive variant vector, the methods of the present invention are superior in that pluripotent stem cells can be induced with high efficiency without low-temperature culturing (for example, culturing at lower than 36.5° C.) and the vector is rapidly eliminated after the induction of pluripotent stem cells. For example, the present invention relates to methods of improving the efficiency of pluripotent stem cell induction in methods that induce pluripotent stem cells without low-temperature culturing by introducing a temperature-sensitive Sendai virus vector containing in one vector the KLF gene, OCT gene, and SOX gene in this order, which include the step of further introducing a Sendai virus vector that contains the KLF gene but not the OCT gene and the SOX gene. The temperature for cell culture can be appropriately selected, and for example, it can be about 37° C., specifically 36.5° C. to 37.5° C., preferably 36.6° C. to 37.4° C. and more preferably 36.7° C. to 37.3° C. In the present invention, pluripotent stem cell induction includes generation of pluripotent stem cells, and improvement of the efficiency of pluripotent stem cell induction includes improvement of the efficiency of pluripotent stem cell generation.

While introduction of the MYC gene is not essential for the induction of pluripotent stem cells, the efficiency of pluripotent stem cell induction can be increased by introducing the MYC gene. The MYC gene can be introduced, for example, by using a temperature-sensitive virus vector, preferably a temperature-sensitive Sendai virus vector.

The present invention provides methods for reprogramming cells, which comprise the step of introducing into differentiated cells such as somatic cells or contacting them with a vector containing the KLF gene, OCT gene, and SOX gene in one vector in this order, and a vector that contains the KLF gene but not the OCT gene and the SOX gene. Moreover, the present invention provides methods for introducing the above reprogramming factor genes in cellular reprogramming, which comprise introducing these reprogramming factor genes using a vector containing the KLF gene, OCT gene, and SOX gene in one vector in this order and a vector that contains the KLF gene but not the OCT gene and the SOX gene, as well as compositions comprising the vectors for use in those methods.

In the present invention, "pluripotent stem cells" refer to stem cells produced from the inner cell mass of an embryo of an animal in the blastocyst stage or cells having phenotypes similar to those cells. Specifically, pluripotent stem cells induced in the present invention are cells that express alkaline phosphatase which is an indicator of ES-like cells. Here, "ES-like cells" indicate pluripotent stem cells having properties and/or morphologies that are similar to ES cells. Furthermore, preferably, when pluripotent stem cells are cultured, they form flat colonies containing cells with a higher proportion of nucleus volume than cytoplasm. Culturing may be carried out suitably with a feeder. Moreover, while cultured cells such as MEF stop proliferating in a few weeks, pluripotent stem cells can be passaged for a long period of time, and this can be confirmed based on their proliferative character that is not lost even when they are passaged, for example, 15 times or more, preferably 20 times or more, 25 times or more, 30 times or more, 35 times or more, or 40 times or more every three days. Furthermore, pluripotent stem cells preferably express endogenous OCT3/4 or Nanog, or more preferably, they express both of them. Furthermore, pluripotent stem cells preferably express TERT, and show telomerase activity (activity to synthesize telomeric repeat sequences). Moreover, pluripotent stem cells preferably have the ability to differentiate into three germ layers (the endoderm, mesoderm, and ectoderm) (this can be confirmed, for example, during teratoma formation and/or embryoid body formation). More preferably, pluripotent stem cells produce germline chimera when they are transplanted into blastocysts, Pluripotent stem cells capable of germline transmission are called germline-competent pluripotent stem cells. Confirmation of these phenotypes can be carried out by known methods (WO 2007/69666; Ichisaka T. et al., Nature 448 (7151): 313-7, 2007).

Furthermore, in the present invention, "differentiated" refers to that a differentiation stage of a cell is progressed more than before, and may refers to, for example, be more differentiated as compared to pluripotent stem cells, and includes states still possessing the ability to differentiate into multiple cell lineages for example, somatic stem cells) and terminally differentiated states. Differentiated cells are cells (other than pluripotent stem cells) derived from pluripotent stem cells. Differentiated cells may be, for example, cells that do not have the ability to differentiate into the three germ layers (the endoderm, mesoderm, and ectoderm). Such cells will not have the ability to form the three germ layers unless they are reprogrammed. Furthermore, differentiated cells may be, for example, cells that cannot produce cells that are not of the germ layer type to which they belong. Differentiated cells may be somatic cells, and for example, they may be cells other than germ cells.

In the present invention, reprogramming refers to converting the differentiation state of a particular cell to a less differentiated state, and includes for example, dedifferentiation of differentiated cells, such as inducing cells with differentiation pluripotency, for example pluripotent stem cells, from cells without differentiation pluripotency. Furthermore, in the present invention, dedifferentiation refers to conversion of a particular cell into a more premature (for example, undifferentiated) state. Dedifferentiation may be reversion of a cell to its initial state or intermediate state in its path of differentiation. Furthermore, dedifferentiation may be a change from a cell unable to produce cells that are not of the same germ layer type to which the cell belongs, into a cell that can differentiate into other germ layer type cells. Dedifferentiation also includes, for example, cells not having triploblastic differentiation ability acquiring this triploblastic differentiation ability. Additionally, dedifferentiation includes the production of pluripotent stem cells.

Furthermore, in the present invention, somatic cells are, for example, cells other than pluripotent stem cells and germ cells. Somatic cells include, for example, multicellular organism-constituting cells other than pluripotent stem cells, and cultured cells thereof. Somatic cells include for example, somatic stem cells and terminally differentiated cells.

The low-temperature culturing in the present invention refers to culturing at a temperature lower than 36.5° C. The low-temperature culturing refers to culturing at a low temperature of preferably under 36.4° C., more preferably, 36.3° C., 36.2° C., 36.1° C., 36° C., 35.9° C., 358° C., 35.7° C., 356° C., 35.5° C., 354° C., 35.3° C., 352° C. or 35.1° C., and even more preferably lower than 35° C. The lower limit is, for example, 30° C., preferably 31° C., and more preferably 32° C., 33° C. or 34° C. Further, about 37° C. in the present invention refers to specifically, 36.5° C. to 37.5° C., preferably 36.6° C. to 37.4° C., and more preferably 36.7° C. to 37.3° C.

Temperature sensitivity in the present invention means that the activity is significantly reduced at the standard temperature for cell culture (for example, 37° C. to 38° C.) compared to that at a low temperature (for example, 30° C. to 36° C.). More preferably, it means that the activity is significantly reduced at 37° C. compared to that at 36° C. For example, in the case of an expression vector, the level of expression of the temperature-sensitive vector is significantly lower at the standard temperature for cell culture (for example, 37° C. to 38° C.) compared to the level of expression at a low temperature (for example, 30° C. to 36° C.). For example, the TS 7 (Y942H/L1361C/L1558I mutations in the L protein), TS 12 (D433A/R434A/K437A mutations in the P protein), TS 13 (D433A/R434A/K437A mutations in the P protein and L1558I mutation in the L protein), TS 14 (D433A/R434A/K437A mutations in the P protein and L1361C in the L protein), TS 15 (D433A/R434A/K437A mutations in the P protein and L1361C/L1558I in the L protein) mutations and such in Sendai virus are temperature-sensitive mutations.

Vectors in the present invention are preferably viral vectors. In the present invention, virus vectors are vectors having genomic nucleic acids derived from the virus, and that can express transgenes by incorporating the transgenes into the nucleic acids. Since Sendai virus vectors are chromosomally non-integrating virus vectors and are expressed in the cytoplasm, there is no risk that the introduced gene will become integrated into the chromosome (nucleus-derived chromsome) of the host. Therefore, the vectors are safe and can be removed after completion of reprogramming. In the present invention, Sendai virus vectors include infectious virus particles, as well as complexes of the viral core, viral genome, and viral proteins, and complexes comprising non-infectious viral particles and such, which are complexes having the ability to express loaded genes upon introduction into cells. For example, in Sendai viruses, ribonucleoproteins (the viral core portion) consisting of a Sendai virus genome and bound Sendai virus proteins (NP, P, and L proteins) can express transgenes in cells when they are introduced into cells (WO 00/70055). Introduction into cells can be appropriately carried out using transfection reagents and the like. Such ribonucleoproteins (RNPs) are also included in the Sendai virus vectors of the present invention.

Sendai virus is a Mononegavirales virus, belongs to Paramyxoviridae including the genera Paramyxovirus, Morbillivirus, Rubulavirus, and Pneumovirus), and contains a single-stranded minus-strand (antisense strand of a viral protein-encoding sense strand) RNA as the genome. Minus-strand RNA is also called negative-strand RNA.

Mononegavirales includes viruses belonging to families such as Rhabdoviridae (including the genera *Vesiculovirus*, *Lyssavirus*, and *Epheinerovirus*), and Filoviridae, in addition to Paramyxovirus (Paramyxoviridae virus) (Virus, vol. 57, No, 1: pp 29-36, 2007; Annu. Rev. Genet. 32, 123-162, 1998; Fields virology fourth edition, Philadelphia, Lippincott-Raven, 1305-1340, 2001; Microbiol. Immunol. 43, 613-624, 1999; Field Virology, Third edition pp. 1205-1241, 1996). Other examples of Paramyxoviridae virus other than Sendai virus include Newcastle disease virus, mumps virus, measles virus, respiratory syncytial virus (RS virus), rinderpest virus, distemper virus, simian parainfluenza virus (SV5), and human parainfluenza viruses I, II, and III; influenza virus belonging to the Orthomyxoviridae family; and the vesicular stomatitis virus and Rabies virus belonging to the Rhabdoviridae family. Further examples include Sendai virus (SeV), human parainfluenza virus-1 (HPIV-1), human parainfluenza virus-3 (HPIV-3), phocine distemper virus (PDV), canine distemper virus (CDV), dolphin molbillivirus (DMV), peste-des-petits-ruminants virus (PDPR), measles virus (MV), rinderpest virus (RPV), Hendra virus (Hendra), Nipah virus (Nipah), human parainfluenza virus-2 (FIPIV-2), simian parainfluenza virus 5 (SV5), human parainfluenza virus-4a (HPIV-4a), human parainfluenza virus-4b (HPIV-4b), mumps virus (Mumps), and Newcastle disease virus (NDV). More preferably, examples include viruses selected from the group consisting of Sendai virus (SeV), human parainfluenza virus-1 (HPW-1), human parainfluenza virus-3 (HPIV-3), phocine distemper virus (PDV), canine distemper virus (CDV), dolphin molbillivirus (DMV), peste-des-petits-ruminants virus (PDPR), measles virus (MV), rinderpest virus (RPV), Hendra virus (Hendra), and Nipah virus (Nipah).

For examples of accession numbers in the database for the nucleotide sequences of Sendai virus genes, see M29343, M30202, M30203, M30204, M51331, M55565, M69046, and X17218 for the NP gene; M30202, M30203, M30204, M55565, M69046, X00583, X17007, and X17008 for the P gene; D11446, K02742, M30202, M30203, M30204, M69046, U31956, X00584, and X53056 for the M gene; D00152, D11446, D17334, D17335, M30202, M30203, M30204, M69046, X00152, and X02131 for the F gene; D26475, M12397, M30202, M30203, M30204, M69046, X00586, X02808, and X56131 for the HN gene; and 1700053, M30202, M30203, M30204, M69040, X00587, and X58886 for the L gene. Examples of viral genes encoded by other viruses include CDV, AF014953; DMV, X75961; HPIV-1, D01070; HPW-2, M55320; HMV-3, D10025; Mapuera, X85128; Mumps, D86172; MV, K01711; NDV, AF064091; PDPR, X74443; PDV, X75717; RPV, X68311; SeV, X00087; SV5, M81442; and Tupaia, AF079780 for the NP gene (also referred to as the N gene); CDV, X51869; DMV, Z47758; HPIV-1, M74081; HP1V-3, X04721; HPIV-4a, M55975; HPIV-4b, M55976; Mumps, D86173; MV; M89920; NDV, M20302; PDV, X75960; RPV, X68311; SeV, M30202; SV5, AF052755; and Tupaia, AF079780 for the P gene; CDV; AF014953; DMV, 147758; HPIV-1 M74081; HPIV-3, D00047; MV, ABO16162; RPV; X68311; SeV; AB005796; and Tupaia, AF079780 for the C gene; CDV, M12669; DMV 230087; HPIV-1, S38067; HPIV-2, M62734; HPIV-3, D00130; HMV-4a, D10241; HPIV-4b, D10242; Mumps, D86171; MV. AB012948; NDV, AF089819; PDPR, 247977; PDV, X75717; RPV, M34018; SeV, U31956; and SV5, M32248 for the M gene; CDV, M21849; DMV, AJ224704; HPN-1, M22347; HP1V-2, M60182; HPIV-3. X05303, HPIV-4a, D49821; HPIV-4b, D49822; Mumps, D86169; MV, AB003178; NDV, AF048763; PDPR, 237017; PDV, AJ224706; RPV, M21514; SeV, D17334; and SV5, AB021962 for the F gene; and CDV, AF112189; DMV, A1224705; HPIV-1, U709498; HPIV-2, D000865; HPIV-3, AB012132; HMV-4A, M34033; HPIV-4B, AB006954; Mumps, X99040; MV, K01711; NDV; AE204872; PDPR, 181358; PDV; 236979; RPV; AF132934; sey, U06433; and SV-5, S76876 for the HN (H or G) gene. However, multiple strains are known for each of the viruses, and genes consisting of a sequence other than those exemplified above may exist due to strain differences. Sendai virus vectors carrying viral genes derived from any of these genes are useful as vectors of the present invention. For example, Sendai virus vectors of the present invention comprise a nucleotide sequence having 90% or higher, preferably 95% or higher, 96% or higher, 97% or higher, 98% or higher, or 99% or higher identity to the coding sequence of any of the above-mentioned viral genes. Furthermore, the Sendai virus vectors of the present invention comprise, for example, a nucleotide sequence encoding an amino acid sequence having 90% or higher, preferably 95% or higher, 96% or higher, 97% or higher, 98% or higher, or 99% or higher identity to an amino acid sequence encoded by the coding sequence of any one of the above-mentioned viral genes. Furthermore, Sendai virus vectors of the present invention comprise, for example, a nucleotide sequence encoding an amino acid sequence with ten or less, preferably nine or less, eight or less, seven or less, six or less, five or less, four or less, three or less, two or less, or one amino acid substitutions, insertions, deletions, andlor additions in an amino acid sequence encoded by the coding sequence of any one of the above-mentioned viral genes.

The sequences referenced by the database accession numbers such as the nucleotide sequences and amino acid sequences described herein refer to sequences on, for example, the filing date and priority date of this application, and can be identified as sequences at the time of either the filing date or priority date of the present application, and are preferably identified as sequences on the filing date of this application. The sequences at the respective time points can be identified by referring to the revision history of the database.

The Sendai virus vectors used in the present invention may be derivatives, and the derivatives comprise viruses with modified viral genes, and chemically modified viruses, and such, so that the ability of the virus to introduce genes is not impaired.

Furthermore, Sendai viruses may be derived from natural strains, wild-type strains, mutant strains, laboratory-passaged strains, and artificially constructed strains and such. An example is the Z strain (Medical Journal of Osaka University Vol. 6, No. 1, March 1955 p 1-15), That is, these viruses may be virus vectors having similar structures as viruses isolated from nature, or viruses artificially modified by genetic recombination, as long as the desired reprogramming can be induced. For example, they may have mutations or deletions in any of the genes of the wild-type virus. Furthermore, incomplete viruses such as DI particles (J. Virol. 68: 8413-8417, 1994) may also be used. For example, viruses having a mutation or deletion in at least one gene encoding a viral envelope protein or a coat protein can be preferably used. Such virus vectors are, for example, virus vectors that can replicate the genome in infected cells but cannot form infectious virus particles. Since there is no worry of spreading the infection to the surroundings, such transmission-defective virus vectors are highly safe. For example, virus vectors that do not contain at least one gene encoding an envelope protein such as F and/or HN or a spike protein, or a combination thereof may be used (WO 00/70055 and WO 00/70070; Li, H.-O. et al., J. Virol. 74(14): 6564-6569 (2000)). If proteins necessary for genome replication (for example, NP, P, and L proteins) are encoded in the genomic RNA, the genome can be amplified in infected cells. To produce defective type of viruses, for example, the defective gene product or a protein that can complement it is supplied in trans in the virus-producing cell (WO 00/70055 and WO 00/70070; Li, H.-O. et al., J. Virol. 74(14): 6564-6569 (2000)). Furthermore, a method of collecting virus vectors as noninfective virus particles (VLP) without completely complementing the defective viral protein is also known (WO 00/70070). Furthermore, when virus vectors are collected as RNPs (for example, RNPs containing the N, L, and P proteins and genomic RNA), vectors can be produced without complementing the envelope proteins.

Furthermore, the use of virus vectors carrying a mutant viral protein gene is also preferred. The present invention particularly provides methods of gene delivery in reprogramming and methods for producing reprogrammed cells using Sendai virus vectors having mutations and/or deletions in the viral gene, and compositions and kits therefor. For example, in the envelope protein and coat proteins, many mutations including attenuation mutations and temperature-sensitive mutations are known. Sendai viruses having these mutant protein genes can be used favorably in the present invention. In the present invention, vectors with lowered cytotoxicity are desirably used. Cytotoxicity can be measured, for example by quantifying the release of lactic acid dehydrogenase (LDH) from cells. For example, vectors with significantly lowered cytotoxicity compared to the wild type can be used. Regarding the degree of lowering of cytotoxicity, for example, vectors showing a significant decrease of, for example 20% or more, 25% or more, 30% or more, 35% or more, 40% or more, or 50% or more in the LDH release level compared to the wild-type in a culture medium of human-derived HeLa cell (ATCC CCL-2) or simian-derived CV-1 cell (ATCC CCL 70) infected MOI (multiplicity of infection) 3 and cultured for three days can be used. Furthermore, mutations that decrease cytotoxicity also include temperature-sensitive mutations. Temperature-sensitive mutations refer to mutations which significantly decrease the activity at the viral host's ordinary temperature (for example, 37° C. to 38° C.) When compared to that at a low temperature (30° C. to 36° C., for example, 30° C. to 32° C.). Such proteins with temperature-sensitive mutations are useful since the viruses can be produced under permissive temperatures (low temperatures). When infected at 37° C., the virus vectors having useful temperature-sensitive mutations in the present invention show, a growth rate or gene expression level of, for example, ½ or less, preferably ⅓ or less, more preferably ⅕ or less, more preferably 1/10 or less, and more preferably 1/20 or less compared to when cultured cells are infected at 32° C.

A Sendai virus vector used in the present invention may be a wild type as long as it does not inhibit reprogramming, can make reprogramming factors be expressed, and can induce or support induction of reprogramming by the reprogramming factors, and it has deletions or mutations in preferably at least one, more preferably at least 2, 3, 4, 5, or more viral genes. Deletions and mutations may be arbitrarily combined and introduced to each of the genes. Herein, a mutation may be a function-impairing mutation or a temperature-sensitive mutation, and is preferably a mutation that decreases the virus particle forming ability (or the nontransmissible virus-like particle (NTVLP) formation ability in the case of nontransmissible viruses (Inoue et al., J. Virol. 77:3238-3246, 2003)), the proliferation rate, and/or the expression level of any of the carried gene to preferably 1/2 or less, more preferably 1/3 or less, more preferably 1/5 or less, more preferably 1/10 or less, and more preferably 1/20 or less at least at 37° C. as compared to the wild type or to a virus not having the mutation. The use of such modified virus vectors can be useful particularly for the induction of pluripotent stem cells. For example, Sendai virus vectors used favorably in the present invention have at least two deleted or mutated viral genes. Such viruses include those with deletions of at least two viral genes, those with mutations in at least two viral genes, and those with a mutation in at least one viral gene and a deletion of at least one viral gene. The at least two mutated or deleted viral genes are preferably genes encoding envelope-constituting proteins. For example, vectors with deletion of the F gene with further deletion of the M and/or the HN gene or further mutation (for example, NTVLP formation-suppressing mutation and/or temperature-sensitive mutation) in the M and/or the HN gene are used favorably in the present invention. Furthermore, for example, vectors with deletion of the F gene with further deletion of the M or the HN gene and further mutation in the remaining M or HN gene (for example, NTVLP formation-suppressing mutation and/or temperature-sensitive mutation) are also used favorably in the present invention. Vectors used in the present invention more preferably have at least three deleted or mutated viral genes (preferably at least three genes encoding envelope-constituting proteins; F, HN, and M). Such virus vectors include those with deletion of at least three genes, those with mutations in at least three genes, those with mutations in at least one gene and deletion of at least two genes, and those with mutations in at least two genes and deletion of at least one gene. As examples of more preferred embodiments, vectors with deletion of the F gene with further deletion of the M and the HN gene or further mutations (for example, NTVLP formation-suppressing mutation and/or temperature-sensitive mutations) in the M and the HN gene are used favorably in the present invention. Furthermore, for example, vectors with deletion of the F gene with further deletion of the M or the HN gene and further mutation in the remaining M or HN gene (for example, NTVLP formation-suppressing mutation and/or temperature-sensitive mutation) are used favorably in the present invention. Such mutated-form viruses can be produced according to known methods.

For example, a preferred mutation of the M gene of Sendai virus includes amino acid substitution of a site arbitrarily selected from the group consisting of position 69 (G69), position 116 (T116), and position 183 (A183) of the M protein (Inoue, M. et al., J. Virol. 2003, 77: 3238-3246). Viruses having a genome encoding a mutant M protein, in which the amino acids of any one site preferably a combination of any two sites, or more preferably all three sites of the three sites mentioned above are substituted in the Sendai virus M proteins to other amino acids, are used preferably in the present invention.

Preferred amino acid mutations are substitution to other amino acids with a side chain having different chemical properties, and examples are substitution to an amino acid with a BLOSUM62 matrix (Henikaff, S. and Henikoff, J. G. (1992) Proc. Natl. Acad. Sci. USA 89: 10915-10919) score of three or less, preferably two or less, more preferably one or less, and even more preferably 0. Specifically, G69, T116, and A183 of the Sendai virus M protein can be substituted to Glu (E), Ala (A), and Ser (S), respectively. Alternatively, mutations homologous to mutations in the M protein of the temperature-sensitive P253-505 measles virus strain (Morikawa, Y et al., Kitasato Arch. Exp. Med. 1991, 64: 15-30) can also be used. Mutations can be introduced according to known mutation methods, for example, using oligonucleotides and such.

Furthermore, examples of preferred mutations in the HN gene include amino acid substitution of a site arbitrarily selected from the group consisting of position 262 (A262), position 264 (G264), and position 461 (K461) of the HN protein of a Sendai virus (Inoue, M. et al., J Virol. 2003, 77: 3238-3246). Viruses having a genome encoding a mutant HN protein in which the amino acids of any one of the three sites, preferably a combination of any two sites, or more preferably all three sites are substituted to other amino acids are used preferably in the present invention. As mentioned above, preferred amino acid substitutions are substitutions to other amino acids with a side chain having different chemical properties. As a preferred example, A262, G264, and K461 of the Sendai virus HN protein are substituted to Thr (T), Arg (R), and Gly (G), respectively. Furthermore, for example, using the temperature-sensitive vaccine strain Urabe AM9 of the mumps virus as a reference, amino acids at positions 464 and 468 of the protein can be mutated (Wright, K. E. et al., Virus Res. 2000, 67: 49-57).

Furthermore, Sendai viruses may have imitations in the P gene and/or the L gene. Examples of such mutations are specifically, mutation of GM at position 86 (E86) in the SeV P protein, and substitution of Leu at position 511 (L511) in the SeV P protein to other amino acids. As mentioned above, preferred amino acid substitutions are substitutions to other amino acids with a side chain having different chemical properties: Specific examples include substitution of the amino acid at position 86 to Lys, and substitution of the amino acid at position 511 to Phe. Furthermore, examples in the protein include substitution of Asn at position 1197 (N1197) and/or Lys at position 1795 (K1795) in the SeV L protein to other amino acids, and similarly as above, preferred amino acid substitutions are substitutions to other amino acids with a side chain having different chemical properties. Specific examples are substitution of the amino acid at position 1197 to Ser, and substitution of the amino acid at position 1795 to Glu. Mutations of the P gene and L gene can significantly increase the effects of sustained infectivity, suppression of release of secondary particles, or suppression of cytotoxicity. Further combination with mutations and/or deletions of envelope protein genes can dramatically increase these effects. Furthermore, examples for the L gene include substitution of Tyr at position 1214 (Y1214) and/or substitution of Met at position 1602 (M1602) of the SeV L protein to other amino acids, and similarly as above, preferred amino acid substitutions are substitutions to other amino acids with a side chain having different chemical properties. Specific examples are substitution of the amino acid at position 1214 to Phe, and substitution of the amino acid at position 1602 to Leu. The above-mentioned mutations can be arbitrarily combined.

For example, Sendai virus vectors in which at least G at position 69, at position 116, and A at position 183 of the SeV M protein, at least A of position 262, G of position 264, and K of position 461 of the SeV HN protein, at least L of position 511 of the SeV P protein, and at least N of position 1197 and K of position 1795 of the SeV L protein are each substituted to other amino acids, and in which the F gene is also deficient or deleted; and F-gene-deleted or -deficient Sendai virus vectors whose cytotoxicity is similar to or lower than those mentioned above and/or whose suppression of NTVLP formation at 37° C. is similar to or higher than those mentioned above are particularly preferred for the expression of nuclear reprogramming factors in the present invention. Specific examples of the substitutions include G69E, T116A, and A183S substitutions for the M protein, A262T, G264R, and K461G substitutions for the HN protein, L511F substitution for the P protein, and N1197S and K1795E substitutions for the L protein.

Examples of mutations of the L protein also include substitutions of an amino acids at sites arbitrarily selected from position 942 (Y942), position 1361 (L1361), and position 1558 (L1558) of the SeV L protein to other amino acids. Similarly as above, preferred amino acid substitutions are substitutions to other amino acids with a side chain having different chemical properties. Specific examples include substitution of the amino acid at position 942 to His, substitution of the amino acid at position 1361 to Cys, and substitution of the amino acid at position 1558 to Ile. In particular, the L protein with substitutions at least at positions 942 or 1558 can be used preferably. For example, mutant L proteins in which, in addition to position 1558, position 1361 is also substituted to another amino acid are preferred as well. Furthermore, mutant L proteins in which, in addition to position 942, position 1558 and/or position 1361 are also substituted to other amino acids are favorable as well. These mutations can increase the temperature sensitivity of the L protein.

Examples of mutations of the P protein include substitutions of amino acids at sites arbitrarily selected from position 433 (D433), position 434 (R434), and position 437 (K437) of the SeV P protein to other amino acids. Similarly as above, preferred amino acid substitutions are substitutions to other amino acids with a side chain having a different chemical properties. Specific examples include substitution of the amino acid at position 433 to Ala (A), substitution of the amino acid at position 434 to Ala (A), and substitution of the amino acid at position 437 to Ala (A). In particular, P proteins in which all three of these sites are substituted can be used preferably. These mutations can increase the temperature sensitivity of the P protein.

F-gene-deleted or -deficient Sendai virus vectors encoding a mutant P protein in which at least at the three positions of D at position 433, R at position 434, and K at position 437 of the SeV P protein are substituted to other amino acids, and a mutant L protein in which at least the L at position 1558 of the SeV L protein is substituted (preferably a mutant L protein in which at least the L at position 1361 is also substituted to another amino acid); and F-gene-deleted or -deficient Sendai virus vectors whose cytotoxicity is similar to or lower than those mentioned above and/or whose temperature sensitivity is similar to or higher than those mentioned above are used preferably in the present invention. In addition to the above-mentioned mutations, each of the viral proteins may have mutations on other amino acids (for example, on ten or less, five or less, four or less, three or less, two or less, or one amino acid). Since vectors comprising the above-mentioned mutations show a high temperature sensitivity, after completion of reprogramming, the vectors can be removed easily by culturing the cells at a normal temperature (for example, about 37° C., specifically 36.5° C. to 37.5° C., preferably 36.6° C. to 37.4° C., and more preferably 36.7° C. to 37.3° C.). For vector removal, culturing may also be carried out at a slightly high temperature (for example, 37.5° C. to 39° C., preferably 38° C. to 39° C., or 38.5° C. to 39° C.).

More specifically, for example, Sendai virus vectors having mutations such as:
TS 7: L (Y942H/L1361C/L1558I);
TS 12: P (D433A/R434A/K437A);
TS 13: P (D433A/R434A/K437A), L (L1558I);
TS 14: P (D433A/R434A/K437A), L (L1361C); and
TS 15: P (D433A/R434A/K437A), L (L1361C/L1558I)
can be used favorably (International Publication No. WO 2010/008054).

Specific vectors may be, for example, an F acne-deleted Sendai virus vector (for example, Z strain) in which the M protein has G69E, T116A, and A183S mutations; the HN protein has A262T, G264R, and K461G mutations; the P protein has L511F mutation; and the L protein has N1197S and K1795E mutations; and vectors produced by further introducing a TS 7, TS 12, TS 13, TS 14, or TS 15 mutation into this vector are more preferred. Specifically, examples include SeV18+/TSΔF (WO 2010/008054 and WO 2003/025570) and SeV(PM)/TSΔF, and vectors produced by further introducing an aforementioned TS 7, TS 12, TS 13, TS 14, or TS 15 mutation into these vectors, but are not limited thereto.

"TSΔF" means carrying G69E, T116A, and A183S mutations in the M protein, A262T, G264R, and K461G mutations in the HN protein, L511F mutation in the P protein, and N1197S and K1795E mutations in the L protein, and deletion of the F gene.

The temperature-sensitive Sendai virus vector comprising in one vector the KLF gene, OCT gene and SOX gene in this order is an F gene-deleted Sendai virus vector that carries specifically G69E, T116A and A183S mutations in the M protein, A262T, G264R and K461G mutations in the HN protein, L511F mutation in the P protein, and N1197S and K1795E mutations in the L protein, and preferably it further has the TS 7, TS 12, TS 13, TS 14 or TS 15 mutations described above. More preferably, it is an F gene-deleted Sendai virus vector that carries G69E, T116A and A183S mutations in the M protein, A262T, G264R and K461G mutations in the HN protein, L511F mutation in the P protein, and N1197S and K1795E mutations in the L protein, and further carries the TS 12 mutations. In the Sendai virus containing the KLF gene, OCT gene and SOX gene, preferably the KLF gene, OCT gene and SOX gene are incorporated in this order immediately after the P gene of Sendai virus, i.e., immediately downstream of the P gene (right to the 5' side of the minus-strand RNA genome).

Without limitations thereto, in particular, SeV(PM)KOS/TS7ΔF, SeV(PM)KOS/TS12ΔF or such is a preferable vector, and SeV(PM)KOS/TS12ΔF is more preferable.

At this time, it is preferable to combine it with a Sendai virus vector expressing the KLF gene (a vector carrying the KLF gene but not the OCT gene and the SOX gene). The Sendai virus vector encoding the KLF gene (i.e. carrying the KLF gene but not the OCT gene and the SOX gene) can be either temperature sensitive or not, and preferably the vector has a mutation that would suppress NTVLP formation at 37° C. NTVLP formation can be measured according to the reference of Inoue et al., J. Virol. 77:3238-3246, 2003. A preferable vector is, for example, F gene-deleted Sendai virus vector that carries G69E, T116A and A183S mutations in the M protein, A262T, G264R and K461G mutations in the HN protein, L511F mutation in the P protein, and N1197S and K1795E mutations in the L protein. The Sendai virus vector carrying the KLF gene but not the OCT gene and the SOX gene can express the loaded gene (KU gene) at 37° C. For the vector, a vector that has a higher efficiency in expressing the loaded gene at 37° C. than the Sendai virus vector containing the KLF gene, OCT gene and SOX gene in this order in one vector is used. Specifically, it is preferably a vector that has lower temperature sensitivity (high resistance and relatively high expression level of the loaded gene at 37° C.) than the temperature sensitive Sendai virus vector containing the KLF gene, OCT gene and SOX gene in this order in one vector. The KLF gene can be inserted, for example, upstream of the N gene of the Sendai virus vector (3' side of the N gene in the genome), and in particular, SeV18+KLF4/TSΔF is a preferable vector.

At this time, it is preferable to combine it with a temperature-sensitive virus vector encoding the MYC gene. A temperature-sensitive virus vector encoding the MYC gene is, for example, a temperature-sensitive Sendai virus vector that encodes the MYC gene. More specifically, it is an F gene-deleted Sendai virus vector that carries G69E, T116A and A183S mutations in the M protein, A262T, G264R and K461G mutations in the HN protein, L511F mutation in the P protein, and N1197S and K1795E mutations in the L protein, and preferably it is a vector that further has the TS 7, TS 12, TS 13, TS 14 or TS 15 mutations described above. More preferably, it is an F gene-deleted Sendai virus vector that carries G69E, T116A and A183S mutations in the M protein, A262T, G264R and K461G mutations in the HN protein, L511F mutation in the P protein, and N1197S and K1795E mutations in the L protein, and further carries the TS 15 mutations. The MYC gene is incorporated, for example, immediately after the HN gene, i.e., immediately downstream of the HN gene (right to the 5' side of the minus-strand RNA genome), for example, between the HN gene and the L gene. More specifically, it can be SeV(HNL) c-rMYC/TS12ΔF, SeV(HNL)c-rMYC/TS13ΔF, or SeV (HNL)c-rMYC/TS15ΔF, and in particular SeV(HNL)c-rMYC/TS15ΔF is preferred. Favorable results can be obtained by combining, in particular, SeV(PM)KOS/ TS12ΔF, SeV(HNL)c-rMYC/TS15ΔF, and SeV18+KLF4/ TSΔF.

The cytotoxicity of vectors can be measured, for example, by quantifying the release of lactate dehydrogenase (LDH) from cells. Specifically, for example, HeLa (Arcc CCL-2) or simian CV-1 (MCC CCL70) is infected at MOI 3, and the amount of LDH released into the culture solution after three days of culture is measured. The lower the amount of LDH released, the lower the cytotoxicity. Furthermore, temperature sensitivity can be determined by measuring the speed of viral proliferation or the expression level of the loaded gene at the viral host's ordinary temperature (for example, 37° C. to 38° C.). If the speed of viral proliferation and/or expression level of the loaded gene are decreased as compared to those without mutations, the mutation is judged to be a temperature-sensitive mutation, and the lower the proliferation speed and/or expression level, the higher the temperature sensitivity is judged to be.

Furthermore, when using an envelope virus, a virus containing a protein in the envelope that is different from the envelope protein originally carried by the virus may be used. For example, by expressing a desired exogenous envelope protein in a virus-producing cell when producing the virus, a virus containing this protein can be produced. Such proteins are not particularly limited and desired proteins, such as adhesion factors, ligands, and receptors that confer an ability to infect to mammalian cells can be used. Specific examples include the G protein of vesicular stomatitis virus (VSV) (VSV-G) The VSV-G protein may be derived from any VSV strain, and for example, VSV-G protein derived from the Indiana serotype strain (J. Virology 39: 519-528 (1981)) may be used, but it is not limited thereto. Sendai virus vector used in the present invention can include arbitrary combinations of other virus-derived envelope proteins.

Reconstitution of recombinant Sendai viruses carrying nuclear reprogramming factors can be carried out using known methods. As specific procedures, typically, Sendai virus can be produced by the steps of (a) transcribing a cDNA encoding the Sendai virus genomic RNA (minus strand) or a complementary strand thereof (plus strand) in a cell that expresses viral proteins (NP, P, and L) necessary for virus particle formation, and (b) collecting a culture supernatant containing the produced viruses. Viral proteins necessary for particle formation may be expressed from the transcribed viral genomic RNA, or they may be provided in trans from sources other than genomic RNA. For example, they can be provided by introducing expression plasmids encoding the NP, P, and L proteins into cells. When viral genes necessary for particle formation are lacking in the genomic RNA, those viral genes may be separately expressed in virus-producing cells to complement particle formation. To express the viral proteins or the RNA genome in cells, vectors having a DNA encoding such proteins or genomic RNA linked downstream of a suitable promoter that functions in a host cell is introduced into the host cell. The transcribed genomic RNA is replicated in the presence of viral proteins, and infectious virus particles are formed. When producing a defective type of virus lacking genes such as those of the envelope proteins, the missing protein, other viral proteins that can complement the function of those proteins, or such may be expressed in the virus-producing cells.

For example, production of Sendai virus can be carried out by using the following known methods (WO 97/16539; WO 97/16538; WO 00/70055; WO 00/70070; WO 01/18223; WO 03/025570; WO 2005/071092; WO 2006/ 137517; WO 2007/083644; WO 2008/007581; Hasan, M. K. et al., J. Gen. Virol. 78: 2813-2820, 1997; Kato, A. et al., 1997, EMBO J. 1, 16: 578-587; and Yu, D. et al., 1997, Genes Cells 2: 457-466; Durbin, A. P. et al., 1997, Virology 235: 323-332; Whelan, S. P. et al., 1995, Proc. Natl. Acad. Sci. USA 92: 8388-8392; Schnell. M. J. et al., 1994, EMBO J. 13: 4195-4203; Radecke, F. et a 1995, EMBO J. 14: 5773-5784; Lawson, N. D. et al., Proc. Natl. Acad. Sci. USA 92: 4477-4481; Garcin, D. et al., 1995, EMBO J. 14: 6087-6094; Kato, A. et al., 1996, Genes Cells 1: 569-579; Baron, M. D. and Barrett, T., 1997, J. Virol, 71: 1265-1271; Bridgen, A. and Elliott, R. M., 1996, Proc. Natl. Acad. Sci, USA 93: 15400-15404; Tokusumi, T. et al., Virus Res. 2002, 86: 33-338; Li, H.-O, et al., J. Virol. 2000, 74: 6564-6569). Regarding methods for proliferation of viruses and methods for producing recombinant viruses, see also "Uirusu-gaku Jikken-gaku Kakuron (Detailed Virology Experiments)", second revised edition (National Institute of Infectious Diseases Students Institute edition, Maruzen, 1982).

Into the above-mentioned Sendai virus, the KLF gene, OCT gene, and SOX gene are incorporated in this order. Into another Sendai virus, the KLF gene is incorporated (the OCT gene and SOX gene are not incorporated into this vector). Generally, these foreign genes can be inserted immediately before (3' side on the genome) or immediately after (5' side on the genome of) any of the viral genes (NP, P, M, F, HN, or L).

Regarding the Sendai virus containing the KLF gene, OCT gene, and SOX gene, preferably, the KLF gene, OCT gene, and SOX gene are incorporated in this order immediately after the Sendai virus P gene, i.e., immediately downstream of the P gene (immediately 5' side on the minus-strand RNA genome). For example, a transcription initiation signal (S sequence), a transcription termination signal (E sequence), and a spacer sequence (intervening sequence (I sequence) and such) may be included between the P gene and the KLF gene; however other transcription units (for example, transcription units encoding protein-coding genes) are not included. Since the Sendai virus carries a minus-strand RNA as the genome, opposite to the usual, the 3' side corresponds to the upstream and the 5' side corresponds to the downstream of the genome. When the KLF gene, OCT gene, and SOX gene are positioned in this order in the Sendai virus genome, among the three genes the KLF gene is positioned closest to the 3' side, and the SOX gene is positioned closest to the 5' side. Since the minus-strand RNA encodes genes in the antisense orientation, the KLF gene, OCT gene, and SOX gene are encoded as an antisense strand on the genome and not as a protein-coding strand (sense strand). When the Sendai virus genome enters a cell, it produces an antigenomic RNA using this genome as template. Antigenome is a plus strand, and the KLF gene, OCT gene and SOX gene are loaded as a protein-coding strand (sense strand). In antigenomic RNA, the KLF gene, OCT gene, and SOX gene are positioned so that among the three genes, the KLF gene is positioned closest to the 5' side and the SOX gene is positioned closest to the 3' side.

The three genes are preferably adjacent to each other (i.e., with no other genes interposed among the three genes). Each of the genes may be appropriately sandwiched between the Sendai virus S (Start) sequence and the E (End) sequence. The S sequence is a signal sequence that initiates transcription, and the E sequence terminates the transcription. The region between the S sequence and the E sequence becomes a single transcription unit. Where appropriate, a sequence that serves as a spacer (intervening sequence) can be inserted between the E sequence of a certain gene and the S sequence of the next gene. For example, a Sendai virus vector that contains a nucleic acid having the constitution of S-KLF gene-E-I-S-OCT gene-E-I-S-SOX gene-E (S, I, and E refer to the S sequence, the I (intervening) sequence, and the E sequence, respectively) in its genome can be used favorably. The P gene and KLF gene on the Sendai virus genome will be linked in the following manner: P gene-E-I-S-KLF gene-, and such.

When the OCT gene, SOX gene, and KLF gene are positioned in this order, for example, a Sendai virus vector that contains a nucleic acid having the constitution of S-OCT gene-E-I-S-SOX gene-E-I-S-KLF gene-E (S, I, and E refer to the S sequence, the I (intervening) sequence, and the E sequence, respectively) in its genome can be used favorably. The P gene and SOX gene on the Sendai virus genome will be linked in the following manner: P gene-E-I-S-SOX gene-, and so on.

While a desired S sequence of Sendai virus may be used as the S sequence, for example, the 3'-UCCCWVUUWC-5' (W=A or U; V=A, C, or G) sequence (SEQ ID NO: 1) may be used favorably. In particular, 3'-UCCCAGUUUC-5' (SEQ ID NO: 2), 3'-UCCCACUUAC-5' (SEQ ID NO: 3), and 3'-UCCCACUUUC-5' (SEQ ID NO: 4) are preferred. When these sequences are presented as DNA sequences encoding the plus strand, they are 5'-AGGGTCAAAG-3' (SEQ ID NO: 5), 5'-AGGGTGAATG-3' (SEQ ID NO: 6), and 5'-AGGGTGAAAG-3' (SEQ ID NO: 7), respectively. An E sequence of the Sendai virus vector is preferably, for example, 3'-ALTUCUUUUU-5' (the plus strand-encoding DNA is 5'-TAAGAAAAA-3'). The I sequence may be, for example, any three bases, and specifically, 3'-GAA-5' (5'-CTT-3' in the plus strand DNA) may be used.

The genome of wild-type Sendai virus includes a short 3' leader region followed by a nucleocapsid (NP) gene, a phospho (P) gene, a matrix (M) gene, a fusion (F) gene, a hemagglutinin-neuraminidase (HN) gene, and a large (L) gene, and then a short 5' trailer region, in this order. Viral genes can be positioned in this order in Sendai virus vectors as well. Production of recombinant vectors comparable to wild-type viruses, and various mutant vectors are already known. Furthermore, it has been shown that gene delivery is possible using the RNP alone without its envelope (WO 00/70055). Therefore, reprogramming can be carried out using Sendai virus RNP as a virus vector.

Sendai viruses are sufficiently functional as vectors if they carry the NP gene, P gene and L gene; and they can replicate genome in cells and express the loaded foreign genes (KLF, OCT, SOX, and such). In a Sendai virus carrying the three genes, NP gene, P gene and L gene as viral genes, the set of KLF, OCT, and SOX genes is inserted, for example, between the P gene and the L gene. In a vector containing the M gene, the set of KLF, OCT, and SOX genes is inserted, for example, between the P gene and the M gene (WO 97/16539). When the F gene is included in an M gene-deleted Sendai virus vector, the set of KLF, OCT, and SOX genes is inserted between the P gene and the F gene (WO 00/70070). For the M and F gene-deleted Sendai virus vector, the position of insertion is between the P gene and the HN gene; and for the F, M, and HN gene-deleted Sendai virus vector, the position of insertion is between the P gene and the L gene (WO 2003/025570, WO 2006/137517), Viral gene-deleted vectors are preferable since they are very safe. In the present invention, a vector having at least the F gene deletion can be preferably used.

Moreover, for a vector containing the KLF gene but not containing the OCT gene and the SOX gene, the KLF gene is inserted for example upstream of the NP gene (between the 3' leader sequence and the NP gene).

The above-mentioned Sendai virus vector containing the KLF, OCT, and SOX genes and the Sendai virus vector containing the KLF gene but not containing the OCT gene and the SOX gene can be appropriately used by the two of them for gene delivery in reprogramming, but they are more preferably used in reprogramming that further involves introduction of the MYC gene. A vector expressing the Glis1 gene (Maekawa et al., Nature, 474:225-229, 2011) instead of the MYC gene may also be combined. The MYC gene or Glis1 gene can be inserted into the above-mentioned Sendai virus vector containing the KLF, OCT and SOX genes or the Sendai virus vector containing the KLF gene but not the OCT gene and the SOX gene, but it may also be used after insertion into a different vector. When inserting the MYC gene or Glis1 gene into a different vector, desired vectors such as plasmids, virus vectors, and non-virus vectors (for example, liposomes) can be used. Examples of virus vectors include Adenovirus vectors and retrovirus vectors, but are not limited thereto. More preferably, the MYC gene or Glis1 gene is inserted into a Sendai virus vector. In the present invention, the above-mentioned Sendai virus vector containing the KLF, OCT, and SOX genes and the Sendai virus vector containing the KLF gene but not the OCT gene and the SOX gene are preferably used in combination with a different Sendai virus vector inserted with the MYC gene or Glis1 gene. The above-mentioned Sendai virus vector can be used as the starting Sendai virus vector for insertion of the MYC gene or Glis1 gene.

When inserting the MYC gene or Glis1 gene into a Sendai virus genome, a desirable site can be selected for the position of gene insertion in the vector. For example, the MYC gene or Glis1 gene is preferably positioned toward the rear of the minus-strand RNA genome (5' side), for example, more towards the 5' end than to the center of the minus-strand RNA virus genome (the position is further on the 5' end than that of the gene in the middle). That is, among the multiple protein-coding sequences positioned on the genome, it is preferably positioned at a site closer to the 5' end than the 3' end (see the Examples). The MYC gene or (Hist gene can be positioned, for example, at the very end of the 5' side (i.e., first position from the 5' end), or at the second or third position from the 5' end. The MYC gene or Glis1 gene may be positioned at the second position from the 5' end of the genome, specifically, between the HN gene and the L gene (between HN-L) when the L gene is at the very end of the 5' side of the genome with the HN gene next to it. In particular, the MYC gene or Glis1 gene is preferably inserted immediately upstream (3' side, for example, between the HN gene and the L gene), or immediately downstream (5' side, for example, between the HN gene and the 5' trailer sequence) of the L gene in the Sendai virus genome. A Sendai virus vector in which the MYC gene has been inserted between the HN gene and L gene is most preferred. The Sendai virus vector may be, for example, an F gene-deleted Sendai virus vector (for example, the Z strain in which the M protein has G69E, T116A and A183S mutations; the HN protein has A262T, G264R, and K461G mutations; the P protein has L511F mutation; and the L protein has N1197S and K1795E mutations; and vectors produced by further introducing a TS 7, TS 12, TS 13, TS 14, or TS 15 mutation into this vector are more preferable.

MYC genes including not only wild type c-MYC but also the T58A mutant, N-MYC, and L-MYC can induce pluripotent stem cells (WO 2007/69666; Blelloch R. et al., Cell Stem Cell, 1: 245-247, 2007). As such, since the family genes can be selected in various ways and used, reprogramming can be induced by appropriately selecting the MYC family genes. Furthermore, a continuous A or T nucleotide sequence of the MYC gene can be substituted by appropriately introducing silent mutations such that the encoded amino acid sequence is not changed.

For example, the amount of wild-type c-MYC expressed by an RNA virus vector such as a Sendai virus vector was found to be small. However, by introducing one or more, preferably two or more, three or more, or four or more mutations selected from a378g, t1122c, t1125c, a1191g, and a1194g, or all five of these mutations into the wild-type c-MYC, the gene can be highly expressed in astable manner from a vector. In the present invention, for example, the modified c-MYC gene shown in SEQ ID NO: 8 (SEQ ID NO: 9 for the amino acid sequence) (referred to as "c-rMYC") can be used suitably. Specifically, examples include SeV(HNL)c-rMYC/TSΔF, SeV(L)c-rMYC/TSΔF, SeV(HNL)c-rMYC/TS15ΔF (WO 2010/008054; Fusaki et al., Proc. Jpn. Acad. Ser. B. Phys. Biol. Sci. Vol. 85, p 348-362 (2009)), and preferably SeV(HNL)c-rMYC/TS15ΔF in particular, but are not limited thereto.

When appropriate, genes for cellular reprogramming and such can be loaded additionally into the above-mentioned Sendai virus vector carrying the KLF, OCT, and SOX genes, the Sendai virus vector containing the KLF gene but not the OCT gene and the SOX gene, and/or the Sendai virus vector containing the MYC gene. Furthermore, other vectors loaded with genes for cellular reprogramming and such may also be combined with the above-mentioned Sendai virus vectors. The genes to be loaded may be desired genes involved in the induction and such of various stem cells such as pluripotent stem cells from differentiated cells. For example, such genes that increase the efficiency of reprogramming can be loaded.

The present invention provides uses of the Sendai virus vectors of the present invention for introducing genes in cellular reprogramming, and uses of these vectors for expressing reprogramming factors in cells to induce reprogramming of those cells. Furthermore, the present invention provides agents containing the Sendai virus vectors of the present invention for introducing genes in cellular reprogramming (transfer agents, gene transfer agents) and agents containing these vectors for expressing reprogramming factors in cells. Furthermore, the present invention relates to agents containing the Sendai virus vectors of the present invention for expressing reprogramming factors in cells to induce reprogramming of the cells. Furthermore, when carrying out nuclear reprogramming of cells, the vectors of the present invention are also useful for expressing desired genes in these cells. Sendai virus vectors of the present invention can be utilized for cellular reprogramming according to the present invention. The induction of reprogramming may be specifically an induction of pluripotent stem cells. The present invention can be used for medical uses and for non-medical uses, and is useful in medical and non-medical embodiments. For example, the present invention can be used for therapeutic, surgical, and/or diagnostic, or non-therapeutic, non-surgical, and/or non-diagnostic purposes.

In the present invention, a nuclear reprogramming factor refers to a gene used, by itself or together with a number of factors, for inducing a differentiated state of a certain cell to change to a more undifferentiated state, or a product thereof, and includes for example, a gene used for inducing dedifferentiation of differentiated cells, or a product thereof. The nuclear reprogramming factors in the present invention include factors essential for nuclear reprogramming and accessorial factors (auxiliary factors) which increase the efficiency of nuclear reprogramming. In the present invention, desired genes to be used for nuclear reprogramming can be loaded into a vector. For example, genes to be used for the production of pluripotent stem cells can further be loaded. Specifically, as the nuclear reprogramming factors for induction of pluripotent stem cells, for example, genes that are expressed in ES cells or early embryo but are not expressed or whose expression is decreased in many differentiated somatic cells (ES cell-specific genes and such) can be used. Such genes are preferably genes that encode transcription factors, nucleoproteins, or such. Methods for identifying nuclear reprogramming factors are already known (WO 2005/80598), and in fact, genes identified using this method have been shown to be useful in reprogramming into pluripotent stem cells (WO 2007/69666)

Examples of such genes include DPPA5 (developmental pluripotency associated 5, ES cell specific gene 1 (ESG1); accession numbers NM_001025290, NM_925274, XM_236761), F-box protein 15 (Fbx15, NM_152676, NM_015798), Nanog (NM_024865, AB093574), ECAT1 (ES cell associated transcript 1; AB211062, AB2I1060), ERAS (ES cell expressed Ras; NM_181532, NM_181548), DNMT3L, (DNA (cytosine-5-)-methyltransferase 3-like; NM_013369, NM_019448), ECAT8 (AB211063, AB211060), GDF3 (growth differentiation factor 3; NM_020634, NM_008108), SOX15 (SRY (sex determining region Y)-box 15; NM_06942, NM_009235), DPPA4 (developmental pluripotency associated 4; NM_018189, NM_028610), DPPA2 (NM_138815, NM_028615), FTHL17 (ferritin, heavy polypeptide-like 17; NM_031894, NM_031261), SALL4 (sal-like 4; NM_020436, NM_175303), OCT3/4 (also called POU5F1; NM_002701, NM_203289, NM_013633, NM_001009178), SOX2 (NM_003106, NM_011443, XM_574919), Rex-1 (ZFP42 (zinc finger protein 42 homolog); NM_174900, NM_009556), Utf1 (undifferentiated embryonic cell transcription factor 1; NM_003577, NM_009482), TCL1A (T-cell leukemia/lymphoma NM_021966, NM_009337), DPPA3 (also called Stella, NM_199286, NM_139218, XM_216263), KLF4 (Kruppel-like factor 4; NM_004235, NM_010637), cateninβ1 (cadherin-associated protein beta 1; NM_001904, NM_007614; including, the S33Y mutant), c-MYC (NM_002467, NM_010849; including the T58A mutant), STAT3 (signal transducer and activator of transcription 3; NM_139276, NM_213659), GRB2 (growth factor receptor-bound protein 2; NM_002086, NM_008163), Glis1 gene (Maekawa et al., Nature, 474: 225-229, 2011; NM_147193, NM_147221), and other genes which are members of the families to which these genes belong. These genes induce pluripotent stem cells upon introduction into cells (WO 2007/69666). Therefore, from among the above-mentioned genes, a gene that is not yet loaded into the vector can be loaded additionally into a Sendai virus vector containing the KLF, OCT, and SOX genes, a Sendai virus vector containing the KLF gene but not containing the OCT gene and SOX gene, and/or a Sendai virus vector containing the MYC gene; alternatively, other vectors equipped with these genes can be used in combination with these Sendai virus vectors. These genes may be incorporated individually into separate vectors, or multiple genes can be incorporated into a single vector together. Furthermore, the individual genes can be incorporated into a single type of vector, or different types of vectors (including chromosome-integrating viral vector and/or non-viral vector) can be used in combination with the above-mentioned Sendai virus vector of the present invention containing the KLF gene, OCT gene, and SOX gene, or the Sendai virus vector containing the KLF gene but not containing the OCT gene and SOX gene. In addition, individual virus vectors are packaged separately, and can be used by combining them at the time of use. Alternatively, multiple virus vectors carrying different genes can be combined in advance as a kit, or they may be mixed to produce a composition. Furthermore, one or more non-integrating virus vectors containing any combination (or all) of these genes, and kits or compositions further containing these vectors can be used favorably for cellular reprogramming, particularly in the production of pluripotent stem cells. In the case of compositions, the vectors may be appropriately combined with a pharmaceutically acceptable carrier and/or a medium, and for example, sterilized water, pH buffers, physiological saline solutions, culture solutions, and such may be mixed in. In these systems, some or most of the nuclear reprogramming genes can be substituted with their expression products that are proteins. More specifically, the compositions and kits of the present invention may include other vectors (chromosome-integrating virus vectors and/or non-viral vectors) that express reprogramming factors and/or compounds, proteins, or such that induce reprogramming as long as they include the above-mentioned Sendai virus vector containing at least the KLF gene, OCT gene, and SOX gene and the Sendai virus vector containing the KLF gene but not containing the OCT gene and SOX gene. All of the factors necessary for reprogramming are preferably expressed from Sendai virus vectors; however, some of them may be expressed from Sendai virus vectors, and the remaining factors may be provided from other vectors and/or compounds (for example, proteins or low-molecular-weight compounds). Furthermore, the methods of the present invention for producing reprogrammed cells are not limited to methods that carry out all gene deliveries using Sendai virus vectors. More specifically, the methods of the present invention only need to use the above-mentioned Sendai virus vector containing at least the KLF gene, OCT gene, and SOX gene and the Sendai virus vector containing the KLF gene but not containing the OCT gene and SOX gene, and include combined use of other vectors (chromosome-integrating virus vectors and/or non-virus vectors) expressing reprogramming factors and/or compounds and such that induce reprogramming. Preferably, they are used by further combining with the above-mentioned Sendai virus vector containing the MYC gene or Glis1 gene.

The present invention also provides the following:

[1] a method of improving the efficiency of inducing (including improving the efficiency of producing) pluripotent stem cells in a method of inducing (including a method of producing) pluripotent stem cells by introducing a vector that comprises in one vector the KLF gene, OCT gene and SOX gene in this order, wherein the method comprises the step of further introducing a vector that comprises the KLF gene but not the OCT gene and the SOX gene;

[2] the method of [1], wherein the vector comprising the KLF gene, OCT gene and SOX gene in this order is a temperature-sensitive virus vector;

[3] the method of [2], wherein the temperature-sensitive virus vector is a temperature-sensitive Sendai virus vector;

[4] the method of [3], wherein the temperature-sensitive Sendai virus vector is an F gene-deleted Sendai virus vector that comprises mutations selected from the group consisting of TS 7 (Y942H L1361C and L1558I mutations in the L protein), TS 12 (D433A, R434A and K437A mutations in the P protein), TS 13 (D433A, R434A and K437A mutations in the P protein, and L1558I mutation in the L protein), TS 14 (D433A, R434A and K437A mutations in the P protein, and L1361C mutation in the L protein) and TS 15 (D433A, R434A and K437A mutations in the P protein, and L1361C and L1558I mutations in the L protein);

[5] the method of [4], wherein the temperature-sensitive Sendai virus vector is an F gene-deleted Sendai virus vector that comprises G69E, T116A and A183S mutations in the M protein, A262T, G264R and K461G mutations in the HN protein, L511F mutation in the P protein, and N1197S and K1795E mutations in the L protein, and further comprises the TS 12 mutations (D433A. R434A and K437A mutations in the P protein);

[6] the method of any of [3] to [5], wherein the KLF gene, OCT gene and SOX gene are incorporated in this order immediately after the P gene of Sendai virus at the 5' side of the P gene in the minus-strand RNA genome);

[7] the method of [3], wherein the temperature-sensitive Sendai virus vector is selected from the group consisting of SeV(PM)KOS/TS7ΔF and SeV(PM)KOS/TS12ΔF;

[8] the method of any of [1] to [7], wherein the vector that comprises the KLF gene but not the OCT gene and the SOX gene is a Sendai virus vector;

[9] the method of [8], wherein the Sendai virus vector that comprises the KLF gene but not the OCT gene and the SOX gene is a Sendai virus vector that has a mutation that suppresses NTVLP formation at 37° C.;

[10] the method of [8], wherein the Sendai virus vector comprising the Ku gene but not the OCT gene and the SOX gene is an F gene-deleted Sendai virus vector that comprises G69E, T116A and A183S mutations in the M protein, A262T, G264R and K461G mutations in the HN protein, L511F mutation in the P protein, and N1197S and K1795E mutations in the L protein;

[11] the method of any of [8] to [10], wherein the KLF gene is incorporated upstream of the N gene (at the 3' side of the N gene in the minus-strand RNA genome);

[12] the method of [8], wherein the Sendai virus vector comprising the KLF gene but not the OCT gene and the SOX gene is SeV/18+KLF4/TSΔF;

[13] the method of any of [11] to [12], which further comprises the step of introducing a vector inserted with a MYC gene;

[14] the method of [13], wherein the MYC gene-inserted vector is a Sendai virus vector;

[15] the method of [14], wherein the MYC gene-inserted Sendai virus vector is a temperature-sensitive Sendai virus vector;

[16] the method of [15], wherein the MYC gene-inserted temperature-sensitive Sendai virus vector is an F gene-deleted Sendai virus vector that comprises mutations selected from the group consisting of TS 7, TS 12, TS 13, TS 14 and TS 15;

[17] the method of [16], wherein the MYC gene-inserted temperature-sensitive Sendai virus vector is an F gene-deleted Sendai virus vector that comprises G69E, T116A and A183S mutations in the M protein, A262T, G264R and K461G mutations in the HN protein, L511F mutation in the P protein, and N1197S and K1795E mutations in the L protein, and further comprises the TS 15 mutations (D433A, R434A and K437A mutations in the P protein, and L1361C and L1558I mutations in the L protein);

[18] the method of any of [14] to [17], wherein the MYC gene is incorporated immediately before the L gene (at the 3' side of the minus-strand RNA genome);

[19] the method of [14], wherein the MYC gene-inserted temperature-sensitive Sendai virus vector is SeV(HNL)c-rMYC/TS1.5ΔF;

[20] the method of any of [13] to [19], wherein the MYC gene is c-rMyc;

[21] the method of any of [11] to [20], which does not involve culturing at a low temperature; and

[22] the method of [21], wherein culturing is carried out at about 37° C.

The present invention also provides the following:

[1] use of a vector that comprises the KLF gene but not the OCT gene and the SOX gene in the manufacture of a pharmaceutical for improving the efficiency of inducing (including improving the efficiency of producing) pluripotent stem cells in a method of inducing (including a method of producing) pluripotent stem cells by introducing a vector that comprises in one vector the KLF gene, OCT gene and SOX gene in this order;

[2] the use of [1], wherein the vector comprising the KLF gene, OCT gene and SOX gene in this order is a temperature-sensitive virus vector;

[3] the use of [2], wherein the temperature-sensitive virus vector is a temperature-sensitive Sendai virus vector;

[4] the use of [3], wherein the temperature-sensitive Sendai virus vector is an F gene-deleted Sendai virus vector that comprises mutations selected from the group consisting of TS 7, TS 12, TS 13 TS 14, and TS 15;

[5] the use of [4], wherein the temperature-sensitive Sendai virus vector is an F gene-deleted Sendai virus vector that comprises G69E, T116A and A183S mutations in the M protein, A262T, G264R and K461G mutations in the HN protein, L511F mutation in the P protein, and N1197S and K1795E mutations in the L protein, and further comprises the TS 12 mutations (D433A, R434A and K437A mutations in the P protein);

[6] the use of any of [3] to [5], wherein the KLF gene, OCT gene and SOX gene are incorporated in this order immediately after the P gene of Sendai virus (at the 5' side of the P gene in the minus-strand RNA genome);

[7] the use of [3], wherein the temperature-sensitive Sendai virus vector is selected from the group consisting of SeV(PM)KOS/TS7ΔF and SeV(PM)KOS/TS12ΔF;

[8] the use of any of [1] to [7], wherein the vector that comprises the KLF gene hut not the OCT gene and the SOX gene is a Sendai virus vector;

[9] the use of [8], wherein the Sendai virus vector that comprises the KLF gene but not the OCT gene and the SOX gene is a Sendai virus vector that has a mutation that suppresses NTVLP formation at 37° C.;

[10] the use of [8], wherein the Sendai virus vector comprising the KLF gene but not the OCT gene and the SOX gene is an F gene-deleted Sendai virus vector that comprises G69E, T116A and A183S mutations in the M protein, A262T, G264R and K461G mutations in the RN protein, L511F mutation in the P protein, and N1197S and K1795E mutations in the L protein;

[11] the use of any of [8] to [10], wherein the KLF gene is incorporated upstream of the N gene (at the 3' side of the N gene in the minus-strand RNA genome);

[12] the use of [8], wherein the Sendai virus vector comprising the KLF gene but not the OCT gene and the SOX gene is SeV18+KLF4/TSΔF;

[13] the use of any of [1] to [12], which further comprises the step of introducing a vector inserted with a MYC gene;

[14] the use of [13], wherein the MYC gene-inserted vector is a Sendai virus vector;

[15] the use of [14], wherein the MYC gene-inserted Sendai virus vector is a temperature-sensitive Sendai virus vector;

[16] the use of [15], wherein the MYC gene-inserted temperature-sensitive Sendai virus vector is an F gene-deloted Sendai virus vector that comprises mutations selected from the group consisting of TS 7, TS 12, TS 13, TS 14 and TS 15;

[17] the use of [16], wherein the MYC gene-inserted temperature-sensitive Sendai virus vector is an F gene-deleted Sendai virus vector that comprises G69E, T116A and A183S mutations in the M protein, A262T, G264R and K461G mutations in the HN protein, L511F mutation in the P protein, and N1197S and K1795E mutations in the L protein, and further comprises the TS 15 mutations (D433A, R434A and K437A mutations in the P protein, and L1361C and L1558I mutations in the L protein);

[18] the use of any of [14] to [17], wherein the MYC gene is incorporated immediately before the L gene (at the 3' side of the minus-strand RNA genome);

[19] the use of [14], wherein the MYC gene-inserted temperature-sensitive Sendai virus vector is SeV(HNL)c-rMYC/TS15ΔF;

[20] the use of any of [13] to [19], wherein the MYC gene is c-rMyc;

[21] the use of any of [1] to [20], which does not involve culturing at a low temperature during induction and/or production; and

[22] the use of [21], wherein culturing is carried out at about 37° C.

The present invention also provides the following:

[1] a composition and a kit for inducing (including producing) pluripotent stem cells, comprising (a) a vector that comprises in one vector the KLF gene, OCT gene and SOX gene in this order and (b) a vector that comprises the Ku gene but not the OCT gene and the SOX gene;

[2] the composition and kit of [1], wherein the vector comprising the KLF gene, OCT gene and SOX gene in this order is a temperature-sensitive virus vector;

[3] the composition and kit of [1], wherein the temperature-sensitive virus vector is a temperature-sensitive Sendai virus vector;

[4] the composition and kit of [3], wherein the temperature-sensitive Sendai virus vector is an F gene-deleted Sendai virus vector that comprises mutations selected from the group consisting of TS 7, TS 12, TS 13, TS 14, and TS 15;

[5] the composition and kit of [4], wherein the temperature-sensitive Sendai virus vector is an F gene-deleted Sendai virus vector that comprises G69E, T116A and A183S mutations in the M protein, A262T, G264R and K461G mutations in the HN protein, L511F mutation in the P protein, and N1197S and K1795E mutations in the L protein, and further comprises the TS 12 mutations (D433A, R4344 and K4374 mutations in the P protein);

[6] the composition and kit of any of [3] to [5], wherein the KLF gene, OCT gene and SOX gene are incorporated in this order immediately after the P gene of Sendai virus (at the 5' side of the P gene in the minus-strand RNA genome);

[7] the composition and kit of [3], wherein the temperature-sensitive Sendai virus vector is selected from the group consisting of SeV(PM)KOS/TS7ΔF and SeV(PM)KOS/TS12ΔF;

[8] the composition and kit of any of [1] to [7], wherein the vector that comprises the KLF gene but not the OCT gene and the SOX gene is a Sendai virus vector;

[9] the composition and kit of [8], wherein the Sendai virus vector that comprises the KLF gene but not the OCT gene and the SOX gene is a Sendai virus vector that has a mutation that suppresses NlTLP formation at 37° C.;

[10] the composition and kit of [8], wherein the Sendai virus vector comprising the KLF gene but not the OCT gene and the SOX gene is an F gene-deleted Sendai virus vector that comprises G69E, T116A and A183S mutations in the M protein, A262T, G264R and K461G mutations in the HN protein, L511F mutation in the P protein, and N1197S and K1795E mutations in the L protein;

[11] the composition and kit of any of [8] to [10], wherein the KLF gene is incorporated upstream of the N gene (at the 3' side of the N gene in the minus-strand RNA genome);

[12] the composition and kit of [8], wherein the Sendai virus vector comprising the KU; gene but not the OCT gene and the SOX gene is SeV18+KLF4/TSΔF;

[13] the composition and kit of any of [1] to [12], which further comprise a vector inserted with a MYC gene;

[14] the composition and kit of [13], wherein the MYC gene-inserted vector is a Sendai virus vector;

[15] the composition and kit of [14], wherein the MYC gene-inserted Sendai virus vector is a temperature-sensitive Sendai virus vector;

[16] the composition and kit of [15], wherein the MYC gene-inserted temperature-sensitive Sendai virus vector is an F gene-deleted Sendai virus vector that comprises mutations selected from the group consisting of TS 7, TS 12, TS 13, TS 14 and TS 15;

[17] the composition and kit of [16], wherein the MYC gene-inserted temperature-sensitive Sendai virus vector is an F gene-deleted Sendai virus vector that comprises G69E, T116A and A183S mutations in the M protein A262T, G264R and K461G mutations in the HN protein, L511F mutation in the P protein, and N1197S and K1795E mutations in the L protein, and further comprises the TS 15 mutations (D433A, R4344 and K437A mutations in the P protein, and L1361C and L1558I mutations in the L protein);

[18] the composition and kit of any of [14] to [17], wherein the MYC gene is incorporated immediately before the L gene (at the 3' side of the minus-strand RNA genome);

[19] the composition and kit of [14], wherein the MYC gene-inserted temperature-sensitive Sendai virus vector is SeV(HNL)c-rMYC/TS15ΔF;

[20] the composition and kit of any of [13] to [19], wherein the MYC gene is c-rMyc;

[21] the composition and kit of any of [1] to [20], which do not involve culturing at a low temperature during induction and/or production; and

[22] the composition and kit of [21], wherein culturing is carried out at about 37° C.

The present invention also provides the following:

[1] a composition and a kit for improving the efficiency of inducing (including improving the efficiency of producing) pluripotent stem cells, comprising (a) a vector that comprises in one vector the KLF gene, OCT gene and SOX gene in this order and (b) a vector that comprises the KLF gene but not the OCT gene and the SOX gene;

[2] the composition and kit of [1], wherein the vector comprising the KLF gene, OCT gene and SOX gene in this order is a temperature-sensitive virus vector;

[3] the composition and kit of [1], wherein the temperature-sensitive virus vector is a temperature-sensitive Sendai virus vector;

[4] the composition and kit of [3], wherein the temperature-sensitive Sendai virus vector is an F gene-deleted Sendai virus vector that comprises mutations selected from the group consisting of TS 7, TS 12, TS 13, TS 14, and TS 15;

[5] the composition and kit of [4], wherein the temperature-sensitive Sendai virus vector is an F gene-deleted Sendai virus vector that comprises G69E, T116A and A183S mutations in the M protein, A262T, G264R and K461G mutations in the HN protein, L511F mutation in the P protein, and N1197S and K1795E mutations in the L protein, and further comprises the TS 12 mutations (D433A, R434A and K437A mutations in the P protein);

[6] the composition and kit of any of [3] to [5], wherein the KLF gene, OCT gene and SOX gene are incorporated in this order immediately after the P gene of Sendai virus (at the 5' side of the P gene in the minus-strand RNA genome);

[7] the composition and kit of [3], wherein the temperature-sensitive Sendai virus vector is selected from the group consisting of SeV(PM)KOS/TS7ΔF and SeV(PM)KOS/TS12ΔF;

[8] the composition and kit of any of [1] to [7], wherein the vector that comprises the KLF gene but not the OCT gene and the SOX gene is a Sendai virus vector;

[9] the composition and kit of [8], wherein the Sendai virus vector that comprises the KLF gene but not the OCT gene and the SOX gene is a Sendai virus vector that has a mutation that suppresses NTVLP formation at 37° C.;

[10] the composition and kit of [8], wherein the Sendai virus vector comprising the KLF gene but not the OCT gene and the SOX gene is an F gene-deleted Sendai virus vector that comprises G69E, T116A and A183S mutations in the M protein, A262T, G264R and K461G mutations in the HN protein, L511F mutation in the P protein, and N1197S and K1795E mutations in the L protein;

[11] the composition and kit of any of [8] to [10], wherein the KLF gene is incorporated upstream of the N gene (at the 3' side of the N gene in the minus-strand RNA genome);

[12] the composition and kit of [8], wherein the Sendai virus vector comprising the KLF gene but not the OCT gene and the SOX gene is SeV18+KLF4/TSΔF;

[13] the composition and kit of any of [1] to [12], which further comprise a vector inserted with a MYC gene;

[14] the composition and kit of [13], wherein the MYC gene-inserted vector is a Sendai virus vector;

[15] the composition and kit of [14], wherein the MYC gene-inserted Sendai virus vector is a temperature-sensitive Sendai virus vector;

[16] the composition and kit of [15], wherein the MYC gene-inserted temperature-sensitive Sendai virus vector is an F gene-deleted Sendai virus vector that comprises mutations selected from the group consisting of TS 7, TS 12, TS 13, TS 14 and TS 15;

[17] the composition and kit of [16], wherein the MYC gene-inserted temperature-sensitive Sendai virus vector is an F gene-deleted Sendai virus vector that comprises G69E, T116A and A183S mutations in the M protein, A262T, G264R and K461G mutations in the HN protein, L511F mutation in the P protein, and N1197S and K1795E mutations in the L protein, and further comprises the TS 15 mutations (D433A, R434A and K437A mutations in the P protein, and L361C and L1558I mutations in the L protein):

[18] the composition and kit of any of [14] to [17], wherein the MYC gene is incorporated immediately before the L gene (at the 3' side of the minus-strand RNA genome);

[19] the composition and kit of [14], wherein the MYC gene-inserted temperature-sensitive Sendai virus vector is SeV(HNL)c-rMYC/TS15ΔF;

[20] the composition and kit of any of [13] to [19], wherein the MYC gene is c-rMyc;

[21] the composition and kit of any of [1] to [20], which do not involve culturing at a low temperature during induction and/or production; and

[22] the composition and kit of [21], wherein culturing is carried out at about 37° C.

In the invention described in the present specification, it is preferable to combine a vector in which specifically the KLF gene, OCT gene, and SOX gene are inserted in this order into one Sendai virus vector (preferably SeV(PM) KOS/TS12ΔF) with a Sendai virus vector that contains the KLF4 gene but not the OCT gene and the SOX gene (preferably SeV18+KLF4/TSΔF). At this time, it is more preferable to combine it further with a Sendai virus vector expressing the MYC gene (preferably SeV(HNL)c-rMYC/TS15ΔF).

The factors that are introduced (the KLF gene, OCT gene, SOX gene, MY C gene, and the like) may be selected appropriately according to the origin of the cells to be reprogrammed, and they may be derived from humans or other mammals such as mice, rats, rabbits, pigs, or primates such as monkeys. Furthermore, the genetic and protein sequences do not necessarily have to be wild-type sequences, and as long as they can induce reprogramming, they may have mutations. Examples of producing pluripotent stem cells using mutant genes are known (WO 2007/69666). For example, a gene encoding an amino acid sequence with one or a small number of (for example, a few, not more than three, not more than five, not more than ten, not more than 15, not more than 20, or not more than 25) amino acid additions, deletions, substitutions, and/or insertions, and which can induce reprogramming may be used in the present invention. Furthermore, as long as biological activity (ability to induce reprogramming) is maintained, for example, polypeptides with deletions or additions of one to several residues (for example, 2, 3, 4, 5, 6, 10, 15, or 20 residues) of amino acids of the N terminus and/or the C terminus, polypeptides with substitution of one to several residues (for example, 2, 3, 4, 5, 6, 10, 15, or 20 residues) of amino acids, and such may be used. Variants which may be used include for example, fragments, analogs, and derivatives of natural proteins, and fusion proteins of natural proteins with other polypeptides (for example, those with addition of heterologous signal peptides or antibody fragments). Specifically, polypeptides comprising a sequence with one or more amino acid substitutions, deletions, and/or additions in the wild-type amino acid sequence, and having a biological activity (for example, activity to induce reprogramming) equivalent to that of wild-type proteins are included. When using a fragment of a wild-type protein, normally, the fragment contains a continuous region of 70% or more, preferably 80% or more, 85% or more, more preferably 90% or more, 95% or more, or 98% or more of the wild-type polypeptide (a mature form in the case of a secretory protein).

Variants of amino acid sequences can be prepared, for example, by introducing mutations to the DNAs encoding the natural polypeptide (Walker and Gaastra, eds. Techniques in Molecular Biology (MacMillan Publishing Company, New York, 1983); Kunkel, Proc. Natl. Acad. Sci. USA 82: 488-492, 1985; Kunkel et al., Methods Enzymol. 154: 367-382, 1987; Sambrook et al., Molecular Cloning: A Laboratory Manual (Cold Spring Harbor Laboratory Press, Plainview, N.Y.), 1989; U.S. Pat. No. 4,873,192). An example of guidance for substituting amino acids without affecting biological activity includes the report by Dayhoff et al. (Dayhoff et al., in Atlas of Protein Sequence and Structure (Natl. Biomed. Res. Found., Washington, D.C.), 1978).

The number of amino acids that are modified is not particularly limited, but for example, it is 30% or less, preferably 25% or less, more preferably 20% or less, more preferably 15% or less, more preferably 10% or less, 5% or less, or 3% or less of all amino acids of the natural mature polypeptide, and is, for example, 15 amino acids or less, preferably ten amino acids or less, more preferably eight amino acids or less, more preferably five amino acids or less, or more preferably three amino acids or less. When substituting amino acids, activities of the protein can be expected to be maintained by substitution to an amino acid with similar side chain properties. Such substitutions are called conservative substitutions in the present invention. Examples of conservative substitutions include substitution and such among amino acids within each of the groups such as basic amino acids (such as lysine, arginine, and histidine), acidic amino acids (for example, aspartic acid and glutamic acid), uncharged polar amino acids (for example, glycine, asparagine, glutamine, serine, threonine, tyrosine, and cysteine), nonpolar amino acids (for example, alanine, valine, leucine, isoleucine, proline, phenylalanine, methionine, and tryptophan), β-branched amino acids (for example, threonine, valine, isoleucine), and aromatic amino acids (for example, tyrosine, phenylalanine, tryptophan, and histidine). Furthermore, examples include substitution among amino acids whose relationship in the BLOSUM62 substitution matrix E. S. Henikoff and J. G. Henikoff, Proc. Acad. Natl. Sci. USA 89: 10915-10919, 1992) is positive.

The modified proteins exhibit a high homology to the amino acid sequence of the wild-type protein. High homology refers to amino acid sequences having, for example, 70% or higher, 75% or higher, 80% or higher, 85% or higher, 90% or higher, 93% or higher, 95% or higher, or 96% or higher identity. Amino acid sequence identity can be determined using, for example, the BLASTP program (Altschul, S. F. et al., J. Mol. Biol. 215: 403-410, 1990). A search can be carried out using default parameters in the Web page of BLAST at NCBI (National Center for Biotechnology Information) (Altschul S. F. et al., Nature Genet. 3: 266-272, 1993; Madden, T. L. et al., Meth. Enzymol. 266: 131-141, 1996; Altschul S. F. et al., Nucleic Acids Res. 25: 3389-3402, 1997; Zhang J. & Madden T. L., Genome Res. 7: 649-656, 1997). Alignment of two sequences can be produced, for example, by the Blast 2 sequences program which compares two sequences (Tatiana A et al, FEMS Microbiol Lett. 174: 247-250, 1999) and the identity of the sequences can be determined. Gaps and mismatches are treated similarly, and for example, a value of identity with respect to the entire amino acid sequence of a naturally-derived cytokine (mature form after secretion) is calculated. Specifically, the proportion of the number of matching amino acids in the total number of amino acids of the wild-type protein (mature form in the case of a secreted protein) is calculated.

Furthermore, genes can be introduced with a silent mutation such that the encoded amino acid sequence is not changed. Particularly, in AT rich genes, by substituting five or more consecutive A or T nucleotides with G or C such that the encoded amino acid sequence is not changed, high expression of genes can be stably obtained.

Examples of modified proteins or proteins used for reprogramming are proteins encoded by nucleic acids that hybridize under stringent conditions with a part or all of the coding region of a gene encoding the wild-type protein and having an activity (activity to induce reprogramming) equivalent to that of the wild-type protein. In hybridization, for example, a probe is prepared either from a nucleic acid comprising a sequence of the coding region of the wild-type protein gene or a complementary sequence thereof or from a nucleic acid which is the object of hybridization, and identification can be carried out by detecting whether or not the probe hybridizes to the other nucleic acid. Stringent hybridization conditions are, for example, conditions of performing hybridization in a solution containing 5×SSC, 7% (NNW) SDS, 100 μg/mL denatured salmon sperm DNA, 5×Denhardt's solution (1×Denhardt's solution includes 0.2% polyvinyl pyrrolidone, 0.2% bovine serum albumin, and 0.2% Ficoll) at 60° C., preferably 65° C., and more preferably 68° C., and then washing by shaking for two hours in 2×SSC, preferably in 1×SSC, more preferably in 0.5×SSC, and more preferably in 0.1×SSC at the same temperature as hybridization.

Examples of genes particularly preferable for inducing cellular reprogramming typically include F-box protein 15 (Fbx15, NM_152676, NM_015798), Nanog (NM_024865, AB093574), ERAS (ES cell expressed Ras; NM_181532, NM_181548), DPPA2 (NM_138815, NM_028615), OCT3/4 (also called POU5F1; NM_002701, NM_203289, NM_013633, NM_001009178), SOX2 (NM_003106, NM_011443, XM_574919), TCL1A (T-cell leukemia/lymphoma 1A; NM_021966, NM_009337), KLF4 (Kruppel-like factor 4; NM_004235, NM_010637), catenin β1 (cadherin-associated protein beta 1; NM_901904, NM_007614; including the S33Y mutant), c-MYC (NM_002467, NM_010849; including the T58A mutant), and Glis1 gene (Makekawa et al., Nature, 474: 225-229, 2011; NM_147193, NM_147221), as well as other genes which are members of the families to which these genes belong. When these genes are introduced, the proportion of colonies showing the morphology of pluripotent stem cells has been reported to be higher than when the four types of genes (OCT3/4, SOX2, KLF4, and c-MYC) are introduced (WO 2007/69666). Therefore, further use of Sendai virus vectors further carrying any one of the above-mentioned genes or a combination thereof in addition to the KLF gene, OCT gene, and SOX gene, Sendai virus vectors carrying a gene other than the OCT gene and SOX gene in addition to the KLF gene, or Sendai virus vectors carrying any one of the above-mentioned genes or a combination thereof in addition to the Sendai virus vector of the present invention carrying the KLF gene, OCT gene, and SOX gene and the vector containing the KLF gene but not the OCT gene and SOX gene, or a combination of these vectors, is useful for use in the induction of cellular reprogramming in the present invention, and in particular, they can be used favorably for the induction of pluripotent stem cells. Individual virus vectors can be used by combining them at the time of use. Furthermore, they can be combined in advance as a kit, or they may be mixed to form a composition. Furthermore, methods for further introducing one or more Sendai virus vectors containing any combination of any (or all) of the above-mentioned genes in addition to the vector containing in one vector the KLF gene, OCT gene, and SOX gene in this order and the vector containing the KLF gene but not containing the OCT gene and the SOX gene, and kits or compositions containing these vectors are also included in the present invention.

It is preferable to combine the vectors of the present invention for expressing the KLF gene, OCT gene, and SOX gene and the vectors containing the KLF gene but not containing the OCT gene and SOX gene particularly with vectors for expressing the MYC gene and/or the Glis1 gene (Takahashi, K. and Yamanaka S., Cell 126: 663-676, 2006; Lowry W E et al., Proc Natl Acad Sci USA, 105(8): 2883-8, 2008; Masaki., H. et al., Stem Cell Res. 1: 105-115, 2008; Maekawa et al., Nature, 474: 225-229, 2011; WO 2007/69666). Herein, the SOX protein, the KLF protein, the MYC protein, and the OCT protein, and their genes refer to proteins and genes which are members belonging to the SOX family, the KLF family, the MYC family, and the OCT family, respectively. There are reports that by making adjustments on that one or more members from each of these four families are expressed, pluripotent stem cells can be induced from various differentiated cells. For example, regarding the SOX family genes, the use of any of the SOX1, SOX2, SOX3, SOX15, and SOX17 genes has been reported to be able to induce pluripotent stem cells (WO 2007/69666). Regarding the KLF family as well, pluripotent stem cells could be induced with KLF4 or KLF2 (WO 2007/69666). Regarding the MYC family as well, not only the wild-type c-MYC but the T58. A mutant, N-MYC, and L-MYC could also induce pluripotent stem cells (WO 2007/69666; Blelloch R, et al., Cell Stem Cell, 1: 245-247, 2007). This way, since genes of the families can be selected in various ways and then used, reprogramming can be induced by appropriately selecting genes from the four families mentioned above.

Specifically, the KLF family includes KLF1 (NM_006563, NM_010635), KLF2 (NM_016270, NM_008452), KLF4 (NM_004235, NM_010637), and KLF5 (NM_001730, NM_09769); the MYC family includes c-MYC (NM_002467, NM_010849, including the T58A mutant), N-MYC (NM_005378, NM_008709), and L-MYC (NM_005376, NM_005806); the OCT family includes OCT1A (NM_002697, NM_198934), OCT3/4 (NM_002701, NM_203289, NM_013633, NM_001009178), and OCT6 (NM_002699, NM_011141); and the SOX family includes SOX1 (NM_005986, NM_009233), SOX2 (NM_003106, NM_011443, XM_574919), SOX3 (NM_05634, NM_009237), SOX7 (NM_31439, NM_011446), SOX15 (NM_006942, NM_009235), SOX17 (NM_022454, NM_011441), and SOX18 (NM_018419, NM_009236). Sendai virus vectors carrying any one of these genes according to the order of the present invention are useful for use in inducing dedifferentiation of cells in the present invention, and can be used favorably for induction of pluripotent stem cells in particular. The most preferred KLF gene, OCT gene, and SOX gene are the OCT3/4 gene, SOX2 gene, and KLF4 gene, respectively.

MYC family genes are not essential for induction of pluripotent stem cells, and pluripotent stem cells can be induced using only the genes of the three families excluding the MYC family genes (Nakagawa M, et al., Nat Biotechnol. 26(1): 101-6, 2008; Wering M. et al., Cell Stem Cell 2(1): 10-2, 2008). When the MYC gene is not expressed, for example, p53 siRNA and UTF I can be used to significantly increase the induction efficiency of pluripotent stem cells (Y. Zhao et al., Cell Stem Cell, 3 (5): 475-479, 2008; N. Maherali, and K. Hochedlinger, Cell Stem Cell, 3 (6): 595-605, 2008). Furthermore, induction of pluripotent stem cells has been also reported to be possible using only the genes of the three families excluding the KLF family genes (Park I H et al., Nature, 451(7175): 141-6, 2008) In addition, by combined use of the G9a histone methyltransferase inhibitor (BIX-01294; Kubicek, S. et al., Mol. Cell 25: 473-481, 2007), induction of pluripotent stem cells has been reported to be possible from fetal NPC using only three genes, i.e., the KLF gene, SOX gene, and MYC gene (Shi Y et Cell Stein Cell, 2(6): 525-8, 2008). Virus vectors that encode the respective genes can be separately prepared individually. They can be used by combining them at the time of use. Any combination or all of them may be combined to form a kit or mixed to form a composition. In addition to the Sendai virus vector of the present invention carrying the KLF gene, OCT gene, and SOX gene and the Sendai virus vector containing the KLF gene but not containing the OCT gene and SOX gene, the present invention also relates to kits or compositions containing any combination (or all) of genes other than these three genes and compounds. The genes may be suitably loaded onto recombinant vectors. Furthermore, a portion of the recombinant vectors included in this kit can be substituted with proteins, synthetic compounds, or such having corresponding functions.

Other genes can be further combined to the above-described combination of genes to increase the efficiency of induction of reprogramming. Examples of such genes include TERT (NM_198253, NM_009354) and/or SV40 large T antigen (NC_001669.1, Fiers, W. (May 11, 1978) Nature 273(5658): 113-120) (Park I H et al., Nature, 451 (7175) 141-6.2008). One or more genes selected from the group consisting of HPV16 E6, HPV16 E7, and Bmil (NM_005180, NM_007552) may also be further combined. Furthermore, one or any combination of genes selected from the group consisting of Fbx15 (Mol Cell Biol. 23(8): 2699-708, 2003), Nanog (Cell 113: 631-642, 2003), ERas (Nature 423: 541-545, 2003), DPPA2 (Development 130: 1673-1680, 2003), TCL1A (Development 130: 1673-1680, 2003), and β-Catenin (Nat Med 10(1): 55-63, 2004) may be expressed. In addition, one or more genes selected from the group consisting of ECAT1 (AB211062, AB211060), DPPA5 (NM_001025290, NM_025274, XM_236761). DNMT3L (NM_013369, NM_019448), ECAT8 (AB211063, AB211061), GDF3 (NM_020634, NM_008108), SOX15 (NM_006942, NM_009235), DPPA4 (NM_018189, NM_028610), FTHL17 (NM_031894, NM_031261), SALL4 (NM_020436, NM_175303), Rex-1 (NM_174900, NM_009556), Utf1. (NM_003577, NM_009482), DPPA3 (NM_199286, NM_139218, XM_216263), STATS (NM_139276, NM_213659), and GRB2 (NM_002086, NM_008163) may be combined. Combinations comprising each NANOG gene (NM_024865, AB093574) and LIN28 gene (NM_024674) in addition to the KLF gene, the OCT gene, and the SOX gene are useful for inducing pluripotent stem cells (Yu J. et al., Science, 318(5858): 1917-20, 2007). In addition, further combining with MYC gene is preferred (Liao J et al., Cell Res. 18(5): 600-3, 2008). By additionally expressing these genes, induction of pluripotent stem cells may be promoted (WO 2007/69666). When mature B cells are the subjects, for example, the myelocytic transcription factor C/EBPα (CCAAT/enhancer-binding-protein α) (NM_004364) can be ectopically expressed, or expression of the B cell transcription factor PaxS (paired box 5; NM_016734) can be suppressed to promote reprogramming (Hanna J, Cell. 133(2): 250-64, 2008). These factors can also be expressed using the Sendai virus vectors of the present invention. Furthermore, a portion of the recombinant vectors included in this kit can be substituted with proteins, synthetic compounds, and such which have corresponding functions.

Furthermore, besides expressing the above-mentioned factors, for example, by combining the addition of compounds, the efficiency of reprogramming can be increased. For example, bFGF (basic fibroblast growth factor) and/or SCF (stem cell factor) can promote the induction of pluripotent stem cells, and moreover can replace the function of c-MYC in the induction of pluripotent stem cells (WO 2007/69666). Furthermore, MAP kinase inhibitor (PD98056) is also useful for establishing pluripotent stem cells that are closer to ES cells, and such (WO 2007/69666). Furthermore, DNA methylase (Dnmt) inhibitors and/or histone deacetylase (HDAC) inhibitors are reported to improve the efficiency of induction of pluripotent stem cells (Huangfu D et al., Nat Biotechnol. (Published online: 22 Jun. 2008, doi:10.1038/nbt1418); Nat. Biotechnol. 26: 795-797 (2008)). For example, combined use of an HDAC inhibitor (VPA) enables induction of pluripotent stem cells by introduction of only two genes, OCT4 and SOX2 (Huangfu, D. et al., Nat Biotechnol. 2008 26(11): 1269-75). Vectors of the present invention are useful as agents used in combination with administration of these compounds. As Dnmt inhibitors, for example, 5-azacytidine and such are useful, and as HDAC inhibitors, for example, suberoylanilide hydroxamic acid (SAHA), trichostatin A (TSA), valproic acid (VPA) and such are useful. Furthermore, when using 5-azacytidine, combined use of glucocorticoid (dexamethasone) can increase the efficiency.

To reprogram cells, for example, (1) a Sendai virus vector of e present invention containing the KLF gene, OCT gene, and SOX gene in this order and a Sendai virus vector containing the KLF gene but not containing the OCT gene and SOX gene, (2) a combination of the vectors of (1) with a Sendai virus vector for expressing the MYC gene or Glis1 gene, (3) a combination produced by further adding to (1) and/or (2) a Sendai virus vector for expressing the NANOG gene and a Sendai virus vector for expressing LIN28, or (4) a combination of the vector of any one of (1) to (4) with vectors carrying other desired reprogramming factors mentioned above, and/or desired reprogramming-inducing compounds, and such may be introduced into cells. When a number of vectors and/or compounds are combined and introduced, the introduction is preferably carried out simultaneously, and specifically, it is preferable to complete the addition of all vectors encoding the reprogramming factors and/or compounds within 48 hours or less, preferably 36 hours or less, more preferably 24 hours or less, 18 hours or less, twelve hours or less, ten hours or less, eight hours or less, six hours or less, three hours or less, two hours or less, or one hour or less of the addition of the first vector, compound, or such. The dose of the vectors can be prepared appropriately and the MOI is, for example, 0.1 or more, preferably 0.3 or more, 0.5 or more, 1 or more, 2 or more, 3 or more. 4 or more, or 5 or more, and 100 or less, preferably 90 or less, 80 or less, 70 or less, 60 or less, 50 or less, 40 or less, 30 or less, 20 or less, 10 or less, or 5 or less. Preferably, infection is carried out, for example, at MOI of 0.3 to 100, more preferably at MOI of 0.5 to 50, more preferably at MOI of 1 to 40, more preferably at MOI of 1 to 30, more preferably at MOI of 2 to 30, and for example at MOI of 3 to 30. The induced pluripotent stem cells form flat colonies very similar to those of ES cells, and express alkaline phosphatase. Furthermore, the induced pluripotent stem cells may express the undifferentiated-cell markers Nanog, OCT4, and/or SOX2, and the like. The induced pluripotent stem cells preferably express TERT and/or show telomerase activity. The present invention also relates to methods for producing cells that express alkaline phosphatase and preferably further express Nanog and/or TERT which are undifferentiated-cell markers, and to a use of the above-mentioned Sendai virus vectors in the production of these cells and in the production of pharmaceutical agents for inducing these cells.

According to the present invention, pluripotent stem cells can be produced from desired cells including adult skin cells and neonatal foreskin cells. According to the present invention, colonies of pluripotent stem cells can be induced from at least certain types of cells (for example adult skin cells and/or neonatal foreskin cells) for example at an incidence rate of $0.03 \times 10^{-5}$ or more, $0.1 \times 10^{-5}$ or more, $0.3 \times 10^{-5}$ or more, $0.5 \times 10^{-5}$ or more, $0.8 \times 10^{-5}$ or more, or $1 \times 10^{-5}$ or more (for example, $1 \times 10^{-5}$ to $1 \times 10^{-3}$), and preferably at an incidence rate of $1.5 \times 10^{-5}$ or more, $1.7 \times 10^{-5}$ or more, $2.0 \times 10^{-5}$ or more, $2.5 \times 10^{-5}$ or more, $3 \times 10^{-5}$ or more, $4 \times 10^{-5}$ or more, $5 \times 10^{-5}$ or more, $8 \times 10^{-5}$ or more, $1 \times 10^{-4}$ or more, $2 \times 10^{-4}$ or more, $3 \times 10^{-4}$ or more, $5 \times 10^{-4}$ or more, $8 \times 10$ or more, $1 \times 10^{-3}$ or more, $1.5 \times 10^{-3}$ or more, $2 \times 10^{-3}$ or more, $5 \times 10^{-3}$, $1 \times 10^{-2}$ or more, $1.5 \times 10^{-2}$ or more, $2 \times 10^{-2}$ or more, $2.5 \times 10^{-2}$ or more, $3 \times 10^{-2}$ or more, $4 \times 10^{-2}$ or more, or $5 \times 10^{-2}$ or more. For example, by the present invention, pluripotent stem cells can be induced from human peripheral blood mononuclear cells with an efficiency of at least $1 \times 10^{-2}$ (0.01%), preferably at least $3 \times 10^{-2}$, $5 \times 10^{-2}$, $8 \times 10^{-2}$, $1 \times 10^{-1}$, $2 \times 10^{-1}$, $3 \times 10^{-1}$, $4 \times 10^{-1}$, or $5 \times 10^{-1}$; and pluripotent stem cells can be induced from human peripheral blood monocytes with an efficiency of at least $1 \times 10^{-3}$ (0.001%), preferably at least $3 \times 10^{-3}$, $5 \times 10^{-3}$, $8 \times 10^{-3}$, $1 \times 10^{-2}$, $2 \times 10^{-2}$, $3 \times 10^{-2}$, $4 \times 10^{-2}$, or $5 \times 10^{-2}$. The MOI may be appropriately established as described above, and for example, it can be performed at 5, 10, or 30. The efficiency of appearance of pluripotent stem cell colonies by the vector of the present invention containing the KLF gene, OCT gene, and SOX gene in this order and a Sendai virus vector that contains the KLF gene but not the OCT gene and the SOX gene is, for example, 1.2 times or more, preferably 1.3 times or more, 1.5 times or more, 1.7 times or more, twice or more, 2.5 times or more, three times or more, 3.5 times or more, four times or more, 4.5 times or more, or five times or more for at least given cells compared to the situation in which the Sendai virus vector of the present invention expressing the KLF gene, OCT gene, and SOX gene is used, but the Sendai virus vector that contains the KLF gene but not the OCT gene and the SOX gene is not used. The methods of the present invention exert remarkable effects compared to conventional methods in that the introduction efficiency of pluripotent stem cells when cultured at 37° C. after vector introduction is significantly high and the vector is rapidly removed after induction of pluripotent stem cells.

Differentiated cells which become the object of induction of reprogramming are not par limited, and desired somatic cells and such may be used. Production of pluripotent stem cells from somatic cells has been shown to be possible not only from cells derived from fetal mice but also from differentiated cells collected from the tail portion of adult mice, and from liver cells, and gastric mucosal cells, and this suggests that the production is not dependent on the cell type or the state of differentiation (WO 2007/069666; Aoi T. et al., Science [Published Online Feb. 14, 2008]; Science. 2008; 321(5889): 699-702). Induction of pluripotent stem cells has been confirmed to be possible in humans as well, from various cells such as adult facial skin-derived fibroblasts, adult synoviocytes, neonatal foreskin-derived fibroblasts, adult mesenchymal stem cells, skin cells from the palm of an adult, and embryonic cells (Takahashi K, et al. (2007) Cell 131: 861-872; Park tH et al., Nature, 451(7175): 141-6, 2008). Furthermore, induction of pluripotent stem cells has been reported similarly from terminally differentiated cells such as pancreatic β cells and B lymphocytes as well (Stadtfeld M et al., Curr Biol. 2008 May 21. [PubMed, PMID: 18501604]; Curr Biol. 2008, 18(12): 890-4; Hanna J. et al., Cell, 133(2): 250-64, 2008). These findings suggest that induction of pluripotent stem cells do not depend on the cells serving as the origin. Methods of the present invention can be applied in the induction of pluripotent stem cells from these desired somatic cells. Specifically, differentiated cells which are the object of reprogramming include fibroblasts, synoviocytes, mucosal cells of the oral cavity, stomach, or such, liver cells, bone marrow cells, tooth germ cells, blood cells (for example, lymphocytes and leukocytes), and other desired cells. Blood cells may be peripheral blood cells. Fibroblasts, monocytes, mononuclear cells, and the like are also preferred. Furthermore, cells may be derived, for example, from cells of embryos, fetuses, newborns, children, adults, or the aged. The origin of the animals is not particularly limited, and includes mammals such as humans and non-human primates (monkeys and such), rodents such as mice and rats, and non-rodents such as bovine, pigs, and goats.

From the colonies of cells which have completed reprogramming, cells from which the vectors have been removed can be selected appropriately. For example, cells from which the vectors have been naturally removed may be selected. To this end, for example, negative selection can be carried out using antibodies specific to the virus vectors (for example, anti-HN antibodies). Furthermore, when using temperature-sensitive vectors, the vectors can be removed easily by culturing at normal temperatures (for example, about 37° C., specifically 36.5° C. to 37.5° C., preferably 36.6° C. to 37.4° C., and more preferably 36.7° C. to 37.3° C.), or by culturing at slightly high temperatures (for example, 37.5° C. to 39° C., preferably 38° C. to 39° C., or 38.5° C. to 39° C.). When SeV(PM)/TSΔF, or vectors with further introduction of mutations such as TS 7, TS 12, TS 13, TS 14, or TS 15 into SeV(PM)/TSΔF are used, passaging leads to natural loss of the vector. Examples of preferred vectors include the combination of SeV(PM)KOS/TS12ΔF and SeV18+KLF4/TSΔF, but are not limited thereto. Furthermore, in this case, the MYC gene can be introduced using SeV(HNL)c-rMYC/TS1.2ΔF, SeV(HNL)c-rMYC/TS13ΔF, SeV(HNL)c-rMYC/TS15ΔF, or such. The combination of SeV(PM)KOS/TS12ΔF, SeV18+KLF4/TSΔF, and SeV(HNL)c-rMYC/TS15ΔF is particularly preferable. Furthermore, not loading the MYC gene into the Sendai virus vectors carrying the KLF gene, OCT gene, and SOX gene has the advantage that reprogramming can be done without use of the carcinogenesis-related MYC gene. This is also advantageous because it is possible to freely select the fourth factor for use from c-MYC, L-MYC, Glis1, or such in addition to the KLF gene, OCT gene, and SOX gene.

Cells produced by the methods of the present invention are useful for causing differentiation into a variety of tissues and cells, and can be used in desired examinations, research, diagnosis, tests, treatments, and such. For example, induced stem cells are expected to be utilized in stem cell therapy. For example, reprogramming is induced by using somatic cells collected from patients, and then somatic stem cells and other somatic cells that are obtained by induction of differentiation can be transplanted into patients. Methods for inducing cellular differentiation are not particularly limited, and for example, differentiation can be induced by retinoic acid treatment, treatment with a variety of growth factors/cytokines, and treatment with hormones. Furthermore, the obtained cells can be used for detecting effects of the desired pharmaceutical agents and compounds, and this enables screening of pharmaceutical agents and compounds to be carried out.

EXAMPLES

Hereinbelow, the present invention is specifically described with reference to the Examples; however, it is not to be construed as being limited thereto. All documents and other references cited herein are incorporated as part of this description.

Example 1

Construction of pSeV(PM)/TSΔF

The method for producing the Sendai virus vector pSeV (PM)/TSΔF used in the present Example is shown below. In the present invention, "(PM)" refers to inserting a reprogramming gene between the P gene and the M gene, and "(HNL)" refers to inserting a reprogramming gene between the HN gene and the L gene. Furthermore, in the present invention, "TS" refers to having G69E, T116A, and A183S mutations in the M protein, A262T, G264R, and K461G mutations in the HN protein, L511F mutation in the P protein, and N1197S and K1795E mutations in the L protein; and "ΔF" shows that the F gene is deleted. Hereinbelow, "SeV(PM)/TSΔF" refers to an F gene-deleted Sendai virus vector (Z strain) having G69E, T116A, and A183S mutations in the M protein; A262T, G264R, and K461G mutations in the HN protein; L511F mutation in the P protein; and N1197S and K1795E mutations in the L protein. This vector has an insertion site (NotI site) for gene introduction immediately downstream of the P gene (between the P gene and M gene). However, these are exemplary, and the present invention is not limited to these examples.

pSeV(PM)/TSΔF was constructed as follows. PCR was carried out (94° C. for three minutes, and 25 cycles of [98° C. for ten seconds, 55° C. for 15 seconds, and 72° C. for 12 minutes], followed by 72° C. for seven minutes) using Litmus SalINheIfrg PmutMtstHNts ΔF-GFP delGFP (International Publication No. WO 2010/008054) as template, together with PMNOTI-F (5'-GAAATTT-CACCTAAGCGGCCGCAATGGCAGATATCTATAG-3') (SEQ ID NO: 10) and PMNOTI-R (5'-CTATAGA-TATCTGCCAATGCGGCCGCTTAGATGAAATTTC-3') (SEQ ID NO: 11). The approximately 11-kb PCR product obtained was treated with DpnI, and then Escherichia coli DH5α, (ToYoBo Code No. DNA-903) was transformed with 20 μL of this reaction solution, A plasmid having the NotI sequence was selected by NotI digestion. Then, a clone that has the correct sequence was selected by sequencing. Thus, Litmus SalINheIfrg PmutMtsHNts(PM)-dF was obtained. Then, Litmus SalINheIfrg PmutMtsHNts(PM)-dF was digested with SalI and NheI, and the collected fragment (approximately 8 kbp) was ligated to a fragment (approximately kbp) collected upon SalI/NheI digestion of the pSeV/ΔSalINheIfrg Lmut plasmid (International Publication No. WO 2003/025570) having two mutations in the L gene. Thus, pSeV (PM)/TSΔF was obtained. This vector has an insertion site (NoI site) for gene introduction between the P and M genes. The Sendai virus generated from a transcription product of this vector is referred to as SeV(PM)/TSΔF.

Example 2

Construction of pSeV18+KLF4/TSΔF

From a Jurkat cDNA library, the KLF gene was amplified by carrying out PCR using the PrimeStar HS DNA polymerase (Takara Bio Inc., Catalogue No. R010A), and this was inserted at the NotI site of a BlueScript plasmid vector to obtain the plasmid pBS-KS-KLF4 (WO2010/008054). pBS-KS-KLF4 was digested with NotI (37° C., 3 hours) and separated by electrophoresis on a 1% agarose gel. A band of approximately 1.5 kbp was excised and purified with the Qiaquick Gel Extraction Kit (Quiagen, Catalogue No. 28706). The NotI fragment containing this KLF4 gene was cloned into the pSeV18+/TSΔF vector at the NotI site, and clones with the correct sequence were selected by sequencing to obtain pSeV18+KLF4/TSΔF. The Sendai virus generated from a transcription product of the pSeV18+/TSΔF vector is referred to as SeV18+/TSΔF, and the Sendai virus generated from a transcription product of the pSeV18+ KLF4/TSΔF vector is referred to as SeV18+KLF4/TSΔF.

Example 3

Construction of pSeV(PM)/TS12ΔF

PCR (94° C. for three minutes, and 30 cycles of [98° C. for 10 seconds, 55° C. for 15 seconds, and 72° C. for 1.5 minutes], followed by 72° C. for five minutes, and ∞ at 4° C.) was carried out using PrimeStar, with pSeV(PM)/TSΔF as template, and primers F3208 (5'-AGAGAACAA-GACTAAGGCTACC-3' (SEQ ID NO: 12)) and R3787 (5'-ACCTTGACAATCCTGATGTGG-3' (SEQ ID NO: 13)). The amplified band of about 600 bp was purified using the QIAquick PCR Purification Kit. PCR (94° C. for three minutes, and 30 cycles of [98° C. for 10 seconds, 55° C. for 15 seconds, and 72° C. for 1.5 minutes], followed by 72° C. for five minutes, and ∞ at 4° C.) was carried out using PrimeStar, with pSeV18+Oct3/4/TS12ΔF (WO 2010/008054; WO 2012/029770) as template, and primers F2001 (5'-CCATCAACACTCCCCAAGGACC-3' (SEQ ID NO:

14)) and R3390 (5'-AGACGTGATGCGTTTGAGGCCC-3' (SEQ ID NO: 15)) The amplified band of about 1.4 kbp was purified using the QIAquick PCR Purification Kit. These PCR products were mixed, and PCR (94° C. for three minutes, and 30 cycles of [98° C. for 10 seconds, 55° C. for 15 seconds, and 72° C. for two minutes], followed by 72° C. for five minutes, and ∞ at 4° C.) was carried out using PrimeStar, and the F2001 and R3787 primers. The PCR products were purified using the QIAquick PCR Purification Kit, digested with SalI and NotI, and then separated by agarose gel electrophoresis. Then, a band of about 1.6 kbp was excised, and purified using the QIAquick Gel Extraction Kit. pSeV(PM)/TSΔF was digested with SalI and NotI, and then separated by agarose gel electrophoresis. Then, a band of about 14.8 kbp was excised, and purified using the QIAquick Gel Extraction Kit. These two SalI and NatI-digested and purified products were used for ligation, and a clone that has the correct sequence was selected by sequencing to obtain pSeV(PM)/TS12ΔF. This vector has an insertion site (Non site) for gene introduction between the P gene and M gene. The Sendai virus generated from a transcription product of this vector is referred to as SeV(PM)/TS12ΔF.

Example 4

Construction of SeV(PM)KOS/TS12ΔF

Plasmids for production of SeV/TS12ΔF vectors carrying the KLF4-OCT3/4-SOX2 genes were produced as shown below. pSeV(PM)/TSΔF was digested with NotI, then purified using the QIA quick PCR Purification Kit (QIAGEN catalogue No. 28106), and then subjected to BAP treatment. Then, this was purified using the QIAquick PCR Purification Kit. pSeV(PM)KOS/TSΔF was digested with NodI, separated by 1% agarose gel electrophoresis, a band of about 3.6 kbp was excised, and purification was carried out using the Qiaquick Gel Extraction Kit (QIAGEN, catalog No. 28706). 100 μl of an elution solution attached to the kit was used for elution. The NotI fragment containing the KLF4 gene, the OCT3/4 gene, and the SOX2 gene was cloned into the NotI site of the pSeV(PM)/TS12ΔF vector, and a clone that has the correct sequence was selected by sequencing. Thus, pSeV(PM)KOS/TS12ΔF was obtained. The Sendai virus generated from a transcription product of this vector is referred to as SeV(PM)KOS/TS12ΔF.

Example 5

Generation of pSeV(HNL)c-rMyc/TS15ΔF

Litmus38TSΔF-P2(HNL)ΔGFP and pSeV/TSΔF-Linker L1361CL15581 (WO2010/008054; WO2012/029770) were individually digested with SalI-NheI, separated by agarose gel electrophoresis, and bands of 8.0 kbp and 8.3 kbp were excised individually and purified. These purified fragments were ligated to obtain pSeV(HNL)/TS15ΔF (a plasmid encoding the antigenome of SeV(HNL)/TS15ΔF). To the NotI site of this pSeV(HNL)/TS15ΔF was introduced a NotI fragment containing the c-rMyc gene which was excised and purified from pBS-KS-c-rMyc by NotI digestion, to obtain pSeV(HNL)c-rMyc/TS15ΔF. The nucleotide sequence and amino acid sequence of c-rMyc are shown in SEQ NOs: 8 and 9. c-rMyc has a378g, t1122c, t1125c, a1191g, and a1194g mutations. The Sendai virus generated from a transcription product of this vector is referred to as SeV(HNL) c-rMyc/TS15ΔF.

Example 6

Production of Induced Pluripotent Stem Cells (iPs Cells) by the Sendai Virus Vector that Retains Genes for Cellular Reprogramming −1

Human neonatal foreskin-derived fibroblasts (BJ) from ATCC (CRL-2522; www.atcc.org) were cultured at 5×10$^5$ overnight in DMEM (GIBCO-BRL, 11995) containing 10% FBS (Cell Culture Bioscience, Cat. No. 171012), penicillin (100 u/ml) and streptomycin (100 μg/ml; Nacalai Tesque, Code 26253 84) (herein below referred to as 10% FBS/PS/DMEM) in a 5% CO2 incubator at 37° C. Then, the cells were infected with the vectors under the conditions below.
Condition 1: SeV(PM)KOS/TS12ΔF+SeV(HNL)c-rMYC/TS15ΔF+SeV18+KLF4/TSΔF
SeV(PM)KOS/TS12ΔF MOI=30
SeV(HNL)c-rMYC/TS15ΔF MOI=30
SeV18+KLF4/TSΔF MOI=3
Condition 2: SeV(PM)KOS/TS12ΔF+SeV(HNL)c-rMYC/TS15ΔF+SeV18+KLF4/TSΔF
SeV(PM)KOS/TS1.2ΔF MOI=30
SeV(HNL)c-rMYC/TS15ΔF MOI=30
SeV18+KLF4/TSΔF MOI=10
Condition 3: SeV(PM)KOS/TS12ΔF+SeV(HNL)c-rMYC/TS15ΔF+SeV18+/TSΔF
SeV(PM)KOS/TS12ΔF MOI=30
SeV(HNL)c-rMYC/TS15 ΔF MOI=30
SeV18+/TS ΔF MOI=3
Condition 4: SeV(PM)KOS/TS12ΔF+SeV(HNL)c-rMYC/TS15ΔF+SeV18+/TSΔF
SeV(PM)KOS/TS12ΔF MOI=30
SeV(HNL)c-rMYC/TS 15ΔF MOI=30
SeV18+/TSΔF
Condition 5: SeV(PM)KOS/TS12ΔF+SeV(HNL)c-rMYC/TS15ΔF
SeV(PM)KOS/TS12ΔF MOI=30
SeV(HNL)c-rMYC/TS15ΔF MOI=30
Condition 6: Vector Non-Administration Group (Control Group)

After the above vectors were administered to cells, they were cultured in a 5% CO$_2$ incubator at 37° C. Assessment was performed at n=2. The medium was exchanged with 10% FBS/PS/DMEM almost everyday. On day 6 of the infection, 1.0×10$^4$ (cells) of the above vector-introduced cells detached using a 0.25% trypsin-EDTA solution were added to 1.25×10$^5$ (cells) of mitomycin-treated feeder cells (for example, MDT) prepared in gelatin-coated 6-well plates, and they were cultured in a CO$_2$ incubator. Next day, the medium was changed from 10% FBS/PS/DMEM to a primate ES cell medium (ReproCell, RCHEMD001) with an addition of bFGF at 4 ng/ml, and the cells were cultured in a 5% CO$_2$ incubator at 37° C. The medium exchange was carried out everyday or once every two days. The medium could be the conditioned medium of the feeder cells.

Figure 2:
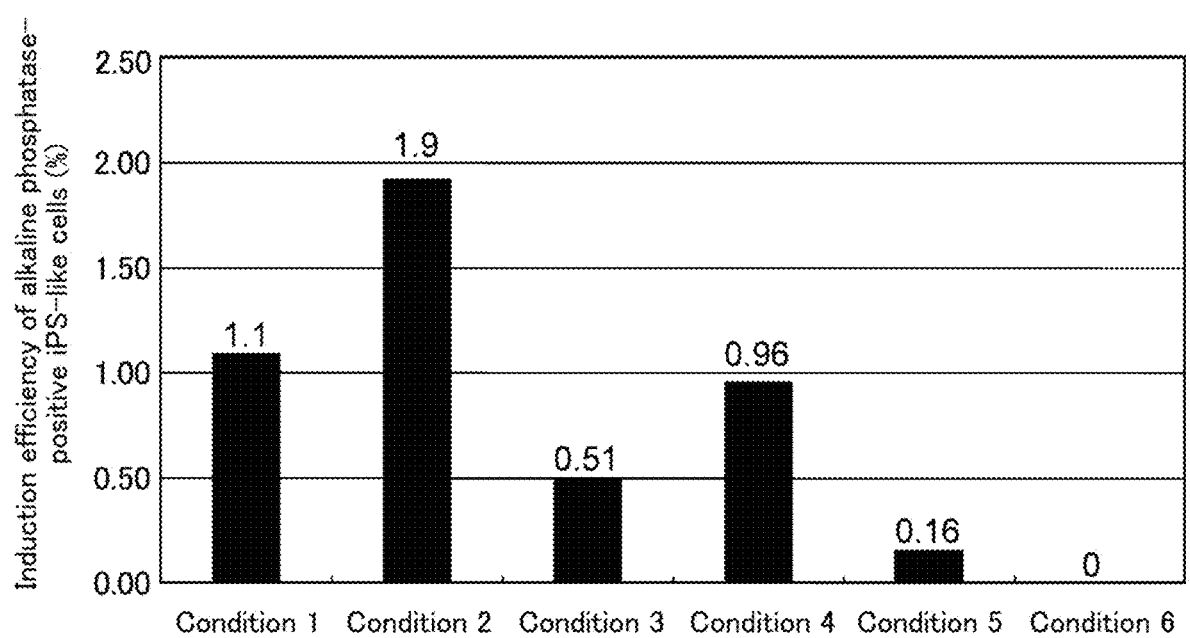
FIG. 2 shows the induction efficiency of alkaline phosphatase-positive iPS-like cells. All the conditions are the same as those in FIG. 3.

On day 28 of the infection, the efficiency of iPS cell induction was observed by staining the activity of alkaline phosphatase which is an ES cell undifferentiation marker with NBCT/BCIP (PIERCE; NBT/BCIP, 1-Step, #34042) (FIG. 1). Compared with the test group that has no addition of the SeV18+KLF4/TSΔF vector (Condition 5 above), the test groups with addition of the SeV18+KLF4/TSΔF vector (Conditions 1 and 2 above) showed improvement of the efficiency of iPS cell induction in a manner dependent on the amount of the SeV18+KLF4/TSΔF vector added. FIG. 2 shows a graph of the average induction efficiency at n=2. The efficiency of iPS cell induction was improved about 6.9 times when the SeV18+KLF4/TSΔF vector was added at MOI=3, and about 12 times when it was added at MOI=10. The efficiency of iPS cell induction was improved about 3.2 times when the SeV18+/TSΔF vector was added at MOI=3, and about 6 times when it was added at MOI=10.

Example 7

Production of Induced Pluripotent Stem Cells (iPS Cells) by the Sendai Virus Vector that Retains Genes for Cellular Reprogramming-2

Human neonatal foreskin-derived fibroblasts (BJ) from ATCC (CRL-2522; www.atcc.org) were cultured in 6-well plates at $5 \times 10^5$ (cells) overnight in DMEM (GIBCO-BRL, 11995) containing 10% FBS (Cell Culture Bioscience, Cat. No. 171012), penicillin (100 u/ml) and streptomycin (100 µg/ml; Nacalai Tesque, Code 26253 84) (herein below referred to as 10% FBS/PS/DMEM) in a 5% CO2 incubator at 37° C. Then, the cells were infected with the vectors under the conditions below. Assessment was performed at n=2.
Condition 1: SeV(PM)KOS/TS12ΔF+SeV(HNL)c-MYC/TS15ΔF+SeV18+KLF4/TSΔF
SeV(PM)KOS/TS12ΔF MOI=5
SeV(HNL)c-rMYC/TS15ΔF MOI=5
SeV18KLF4/TSΔF MOI=5
Condition 2: SeV(PM)KOS/TS12ΔF+SeV(HNL)c-rMYC/TS15ΔF+SeV18+KLF4/TSΔF
SeV(PM)KOS/TS12ΔF MOI=30
SeV(HNL)c-rMYC/TS 15ΔF MOI=30
SeV18+KLF4/TSΔF MOI=10
Condition 3: SeV(PM)KOS/TS12ΔF+SeV(HNL)c-rMYC/TS15ΔF
SeV(PM)KOS/TS12ΔF MOI=5
SeV(HNL)c-rMYC/TS 15 ΔF MOI=5
Condition 4: SeV(PM)KOS/TS12ΔF+SeV(HNL)c-rMYC/TS15ΔF
SeV(PM)KOS/TS12ΔF MOI=30
SeV(HNL)c-rMYC/TS15ΔF MOI=30
Condition 5: Vector Non-Administration Group 1 (Control Group 1)
Condition 6: Vector Non-Administration Group (Control Group 2)

After the above vectors were administered to cells, Conditions 1, 2 and 5 were cultured in a 5% $CO_2$ incubator at 37° C., and Conditions 3, 4 and 6 were cultured in a 5% $CO_2$ incubator at 35° C. The medium was exchanged with 10% FBS/PS/DMEM almost everyday. On day 6 of the infection, $1.0 \times 10^4$ (cells) of the above vector-introduced cells detached using a 0.25% trypsin-EDTA solution were added to $1.25 \times 10^5$ (cells) of mitomycin-treated feeder cells (for example, MEF) prepared in gelatin-coated 6-well plates, and they were cultured in n5% $CO_2$ incubator at 37° C. Next day, the medium was changed from 10% FBS/PS/DMEM to a primate ES cell medium (ReproCell, RCHEMD001) with an addition of bFGF at 4 ng/ml, and the cells were cultured in a 5% $CO_2$ incubator at 37° C. The medium exchange was carried out everyday or once every two days. The medium could be the conditioned medium of the feeder cells.

Figure 3:
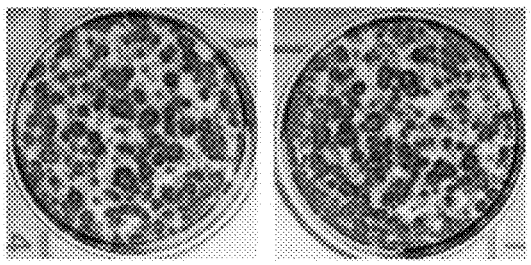
FIG. 3 shows alkaline phosphatase-stained colonies. The number of alkaline phosphatase-positive colonies that appeared under Conditions 1 and 2 was significantly high.
Figure 3:
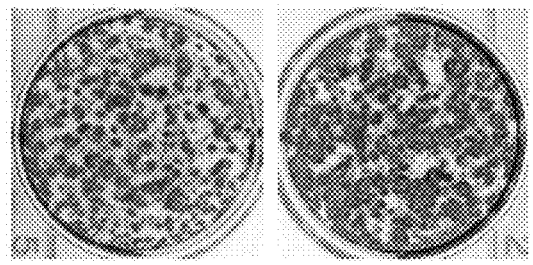
Figure 3:
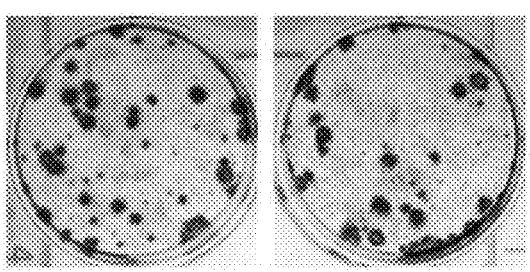
Figure 3:
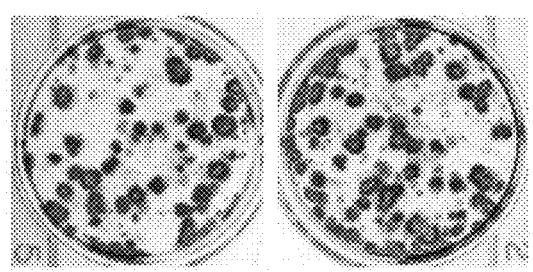
Figure 3:
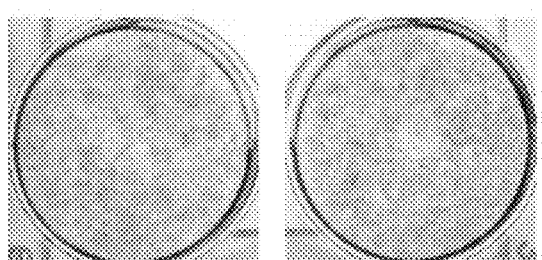
Figure 3:
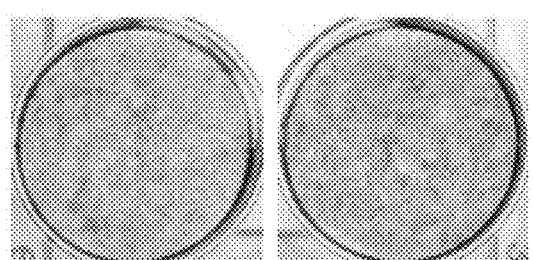
Figure 4:
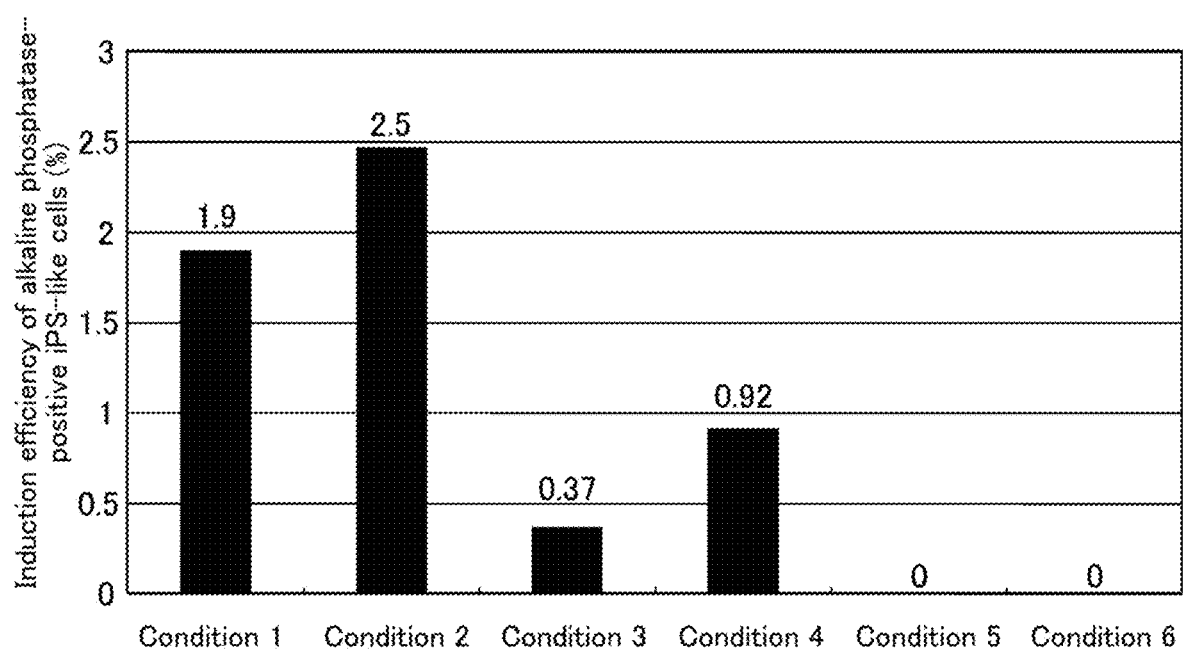
FIG. 4 shows the induction efficiency of alkaline phosphatase-positive iPS-like cells. The efficiency of inducing pluripotent stem cells from BJ cells is shown. All the conditions are the same as those in FIG. 3.

On day 28 of the infection, the efficiency of iPS cell induction was observed by staining the activity of alkaline phosphatase which is an ES cell undifferentiation marker with NBCT/BCIP (PIERCE; NBT/BCIP, 1-Step, #34042) (FIG. 3). Compared with the test groups that have no addition of the SeV18+KLF4/TSΔF vector (Conditions 3 and 4 above), the test groups with addition of the SeV18+KLF4/TSΔF vector (Conditions 1 and 2 above) showed a high efficiency in the induction of iPS cells. In the vector non-administration groups (Conditions 5 and 6 above), the induction of iPS cells was not observed. HQ 4 shows a graph of the average values from results obtained at n=2.

Example 8

Production of Induced Pluripotent Stem Cells (iPS Cells) by the Sendai Virus Vector that Retains Genes for Cellular Reprogramming-3

Human adult skin-derived fibroblasts HDF (Applications, Inc. 106-05A-1388) were 10 cultured in 6-well plates at $5 \times 10^5$ (cells) overnight in DMEM (GIBCO-BRL, 11995) containing 10% FBS (Cell Culture Bioscience, Cat. No. 171012), penicillin (100 u/ml) and streptomycin (100 µg/ml; Nacalai Tesque, Code 26253 84) (herein below referred to as 10% FBS/PS/DMEM) in a 5% CO2 incubator at 37° C. Then, the cells were infected with the vectors under the conditions below. Assessment was performed at n=2.
Condition 1: SeV(PM)KOS/TS12ΔF+SeV(HNL)c-rMYC/TS15ΔF+SeV18+KLF4/TSΔF
SeV(PM)KOS/TS12ΔF MOI=5
SeV(HNL)c-rMYC/TS 15ΔF MOI=5
SeV18+KLF4/TSΔF MOI=5
Condition 2: SeV(PM)KOS/TS12ΔF+SeV(HNL)c-rMYC/TS15ΔF+SeV18+KLF4/TSΔF
SeV(PM)KOS/TS 12ΔF MOI=30
SeV(HNL)c-rMYC/TS15ΔF MOI=30
SeV18+KLF4/TSΔF MOI=10
Condition 3: SeV(PM)KOS/TS12ΔF+SeV(HNL)c-rMYC/TS15ΔF
SeV(PM)KOS/TS12ΔF MO=30
SeV(HNL)c-rMYC/TS15ΔF MOI=30
Condition 4: SeV(PM)KOS/TS12ΔF+SeV(HNL)c-rMYC/TS15ΔF
SeV(PM)KOS/TS12ΔF MOI=5
SeV(HNL)c-rMYC/TS15 ΔF MOI=5
Condition 5: Vector Non-Administration Group 1 (Control Group 1)
Condition 6: Vector Non-Administration Group 2 (Control Group 2)

After the above vectors were administered to cells, Conditions 1, 2 and 5 were cultured in a 5% $CO_2$ incubator at 37° C., and Conditions 3, 4 and 6 were cultured in a 5% $CO_2$ incubator at 35° C. The medium was exchanged with 10% FBS/PS/DMEM almost everyday. On day 6 of the infection, $1.0 \times 10^5$ (cells) of the above vector-introduced cells detached using a 0.25% trypsin-EDTA solution were added to $1.25 \times 1.0^5$ (cells) of mitomycin-treated feeder cells (for example, MU) prepared in gelatin-coated 6-well plates, and they were cultured in a 5% $CO_2$ incubator at 37° C. Next day, the medium was changed from 10% FBS/PS/DMEM to a primate ES cell medium (ReproCell, RCHEMD001) with an addition of bFGF at 4 ng/ml, and the cells were cultured in a 5% $CO_2$ incubator at 37° C. The medium exchange was carried out everyday or once every two days. The medium could be the conditioned medium of the feeder cells.

Figure 5:
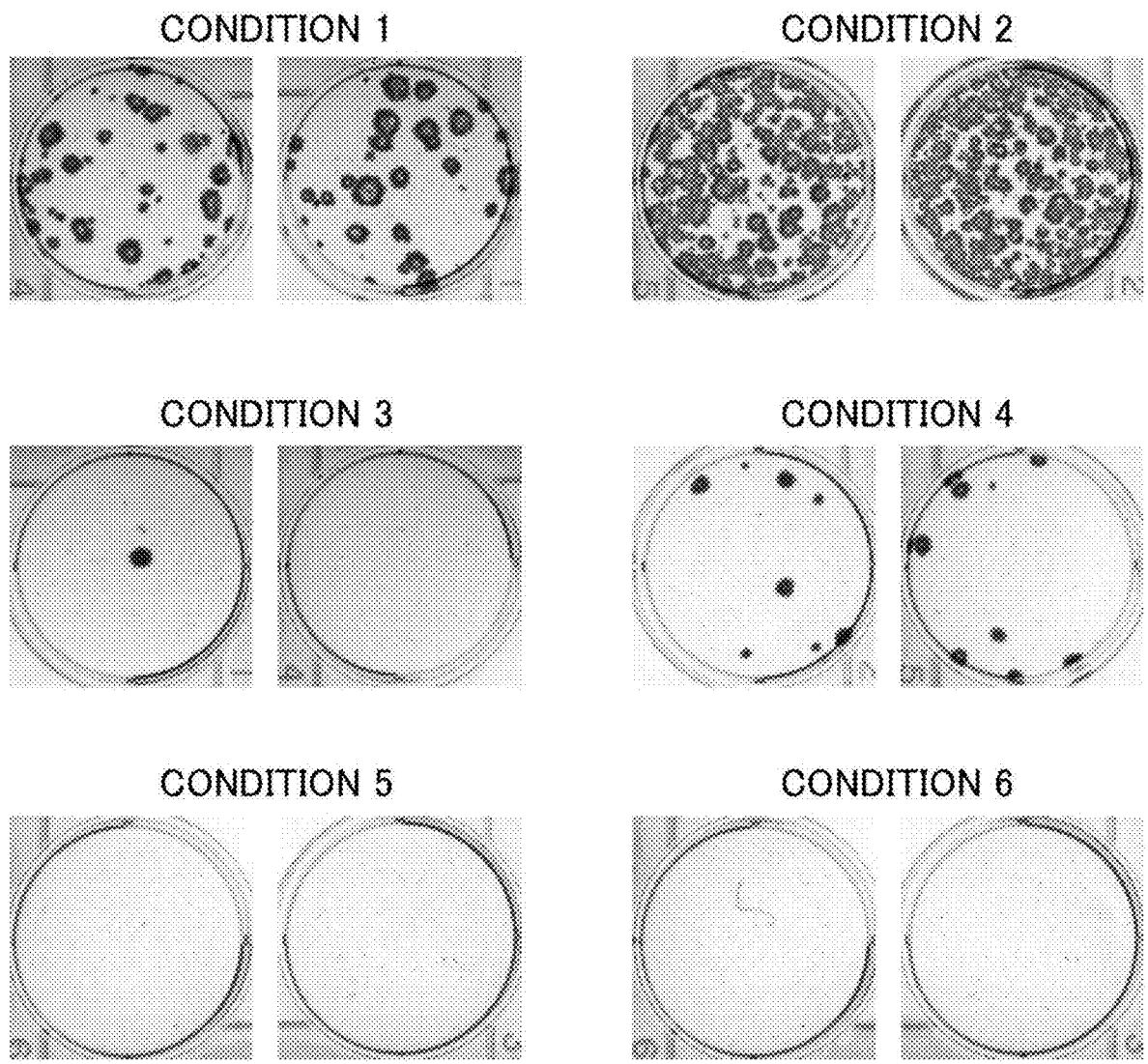
FIG. 5 shows the induction efficiency of alkaline phosphatase-positive iPS-like cells. It shows results of alkaline phosphatase-staining of the cells on day 28 after infection of human adult skin-derived fibroblasts (HDF) with the vector.
Figure 6:
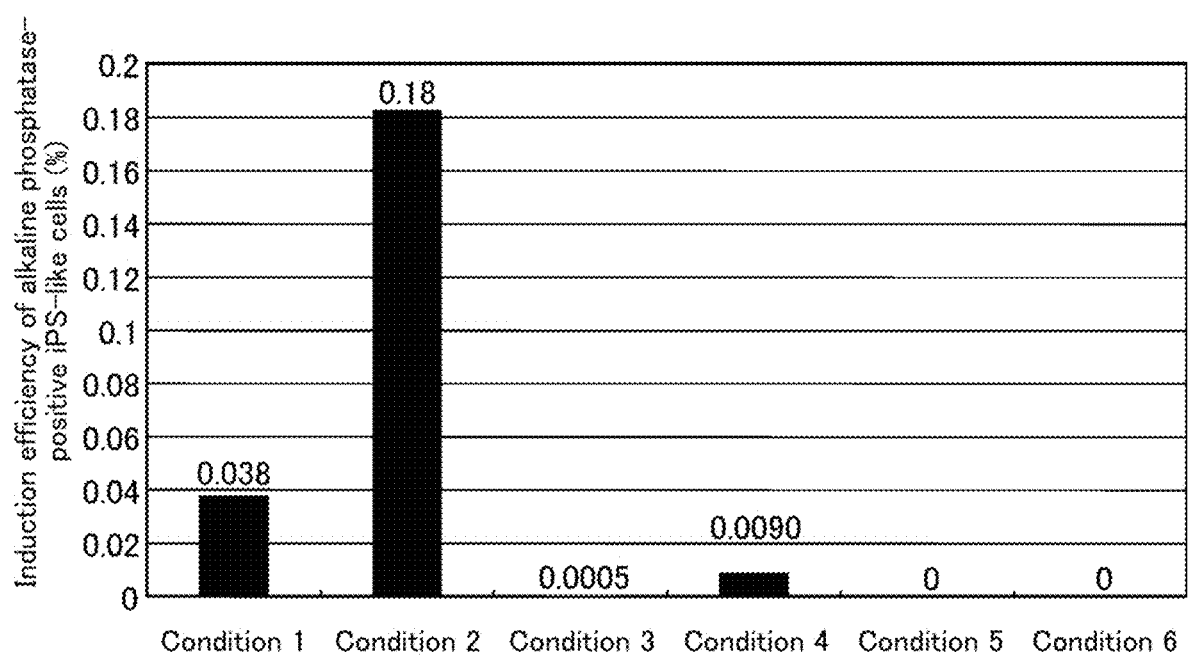
FIG. 6 shows the induction efficiency of alkaline phosphatase-positive iPS-like cells. The efficiency of inducing pluripotent stem cells from human adult skin-derived fibroblasts (IMF) is shown. All the conditions are the same as those in FIG. 5.

On day 28 of the infection, the efficiency of iPS cell induction was observed by staining the activity of alkaline phosphatase which is an ES cell undifferention marker with NBCT/BCIP (PIERCE; NBT/BCIP, 1-Step, #34042) (FIG. 5). Compared with the test groups that have no addition of the SeV18+KLF4/TSΔF vector (Conditions 3 and 4 above), the test groups with addition of the SeV18+KLF4/TSΔF vector (Conditions 1 and 2 above) showed a high efficiency in the induction of iPS cells. In the vector non-administration groups (Conditions 5 and 6 above), the induction of iPS cells was not observed. FIG. 6 shows a graph of the average values from results obtained at n=2.

Example 9

Production of Induced Pluripotent Stem Cells (iPS Cells) by the Sendai Virus Vector that Retains Genes for Cellular Reprogramming-4

Human fetal lung cell-derived fibroblasts (MRC-5; ATCC, CCL-171) were cultured in 6-well plates at $2\times10^5$ (cells) overnight in DMEM (GIBCO-BRL, 11995) containing 10% FBS (Cell Culture Bioscience, Cat. No. 171012), penicillin (100 u/ml) and streptomycin (100 µg/ml; Nacalai Tesque, Code 26253-84) (herein below referred to as 10% FBS/PS/DMEM) in a 5% CO2 incubator at 37° C. Then, the cells were infected with the vectors under the conditions below. Assessment was performed at n=2.
Condition 1: SeV(PM)KOS/TS12ΔF+SeV(HNL)c-rMYC/TS15ΔF+SeV18+KLF4/TSΔF
SeV(PM)KOS/TS12ΔF MOI=5
SeV(HNL)c-rMYC/TS 15ΔF MOI=5
SeV18+KLF4/TSΔF MOI=5
Condition 2: SeV(PM)KOS/TS12ΔF+SeV(HNL)c-MYC/TS15ΔF+SeV18+KLF4/TSΔF
SeV(PM)KOS/TS12ΔF MOI=30
SeV(HNL)c-rMYC/TS15ΔF MOI=30
SeV18+KLF4/TSΔF MOI=10
Condition 3: SeV(PM)KOS/TS12ΔF+SeV(HNL)c-rMYC/TS15ΔF
SeV(PM)KOS/TS 2ΔF MOI=5
SeV(HNL)c-rMYC/TS 15ΔF MOI=5
Condition 4: SeV(PM)KOS/TS12ΔF+SeV(HNL)c-rMYC/TS15ΔF
SeV(PM)KOS/TS12ΔF MOI=30
SeV(HNL)c-rMYC/TS15ΔF MOI=30
Condition 5: Vector Non-Administration Group 1 (Control Group 1)
Condition 6: Vector Non-Administration Group 2 (Control Group 2)

After the above vectors were administered to cells, Conditions 1, 2 and 5 were cultured in a 5% $CO_2$ incubator at 37° C., and Conditions 3, 4 and 6 were cultured in a 5% $CO_2$ incubator at 35° C. The medium was exchanged with 10% FBS/PS/DMEM almost everyday. On day 6 of the infection, $1.0\times10^5$ (cells) of the above vector-introduced cells detached using a 0.25% trypsin-EDTA solution were added to $1.25\times10^5$ (cells) of mitomycin-treated feeder cells (for example, MEF) prepared in gelatin-coated 6-well plates, and they were cultured in a 5% $CO_2$ incubator at 37° C. Next day, the medium was changed from 10% FBS/PS/DMEM to a primate ES cell medium (ReproCell, RCHEMD001) with an addition of bFGF at 4 ng/ml, and the cells were cultured in a 5% $CO_2$ incubator at 37° C. The medium exchange was carried out everyday or once every two days. The medium could be the conditioned medium of the feeder cells.

Figure 7:
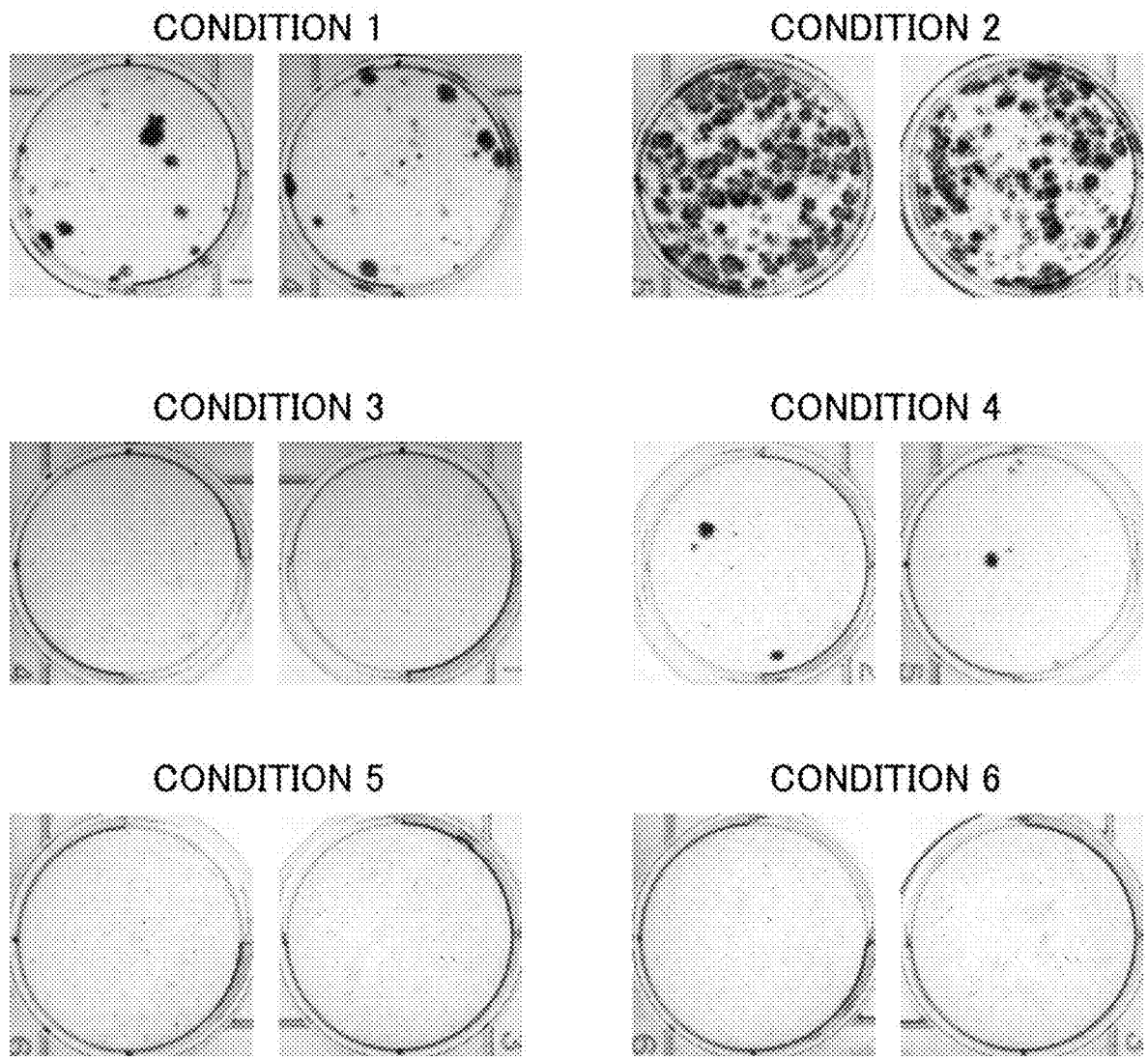
FIG. 7 shows the induction efficiency of alkaline phosphatase-positive iPS-like cells. It shows results of alkaline phosphatase-staining of the cells on day 28 after infection of human fetal lung cell-derived fibroblasts (MRC-5) with the vector.
Figure 8:
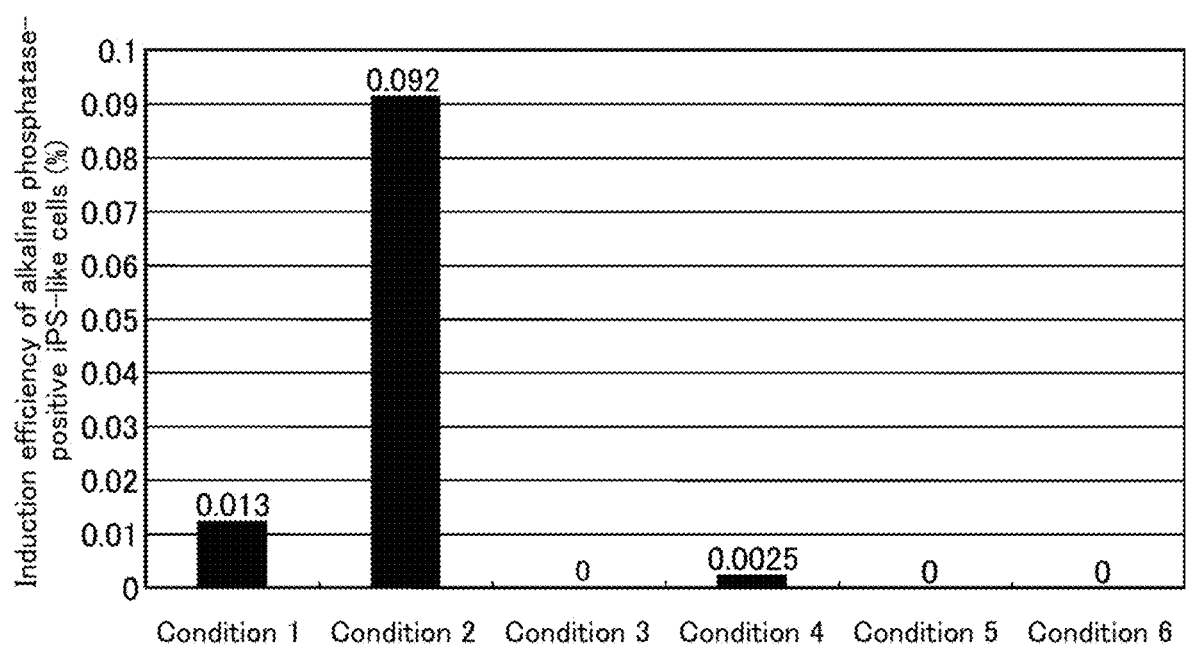
FIG. 8 shows the induction efficiency of alkaline phosphatase-positive iPS-like cells. It shows the induction efficiency of alkaline phosphatase-positive colonies. All the conditions are the same as those in FIG. 7.

On day 28 of the infection, the efficiency of iPS cell induction was observed by staining the activity of alkaline phosphatase which is an ES cell undifferentiation marker with NBCT/BCIP (PIERCE; NBT/BCIP, 1-Step, #34042) (FIG. 7). Compared with the test groups that have no addition of the SeV18+KLF4/TSΔF vector (Conditions 3 and 4 above), the test groups with addition of the SeV18+KLF4/TSΔF vector (Conditions 1 and 2 above) showed a high efficiency in the induction of iPS cells. In the vector non-administration groups (Conditions 5 and 6 above), the induction of iPS cells was not observed. FIG. 8 shows a graph of the average values from results obtained at n=2.

Example 10

Figure 9:
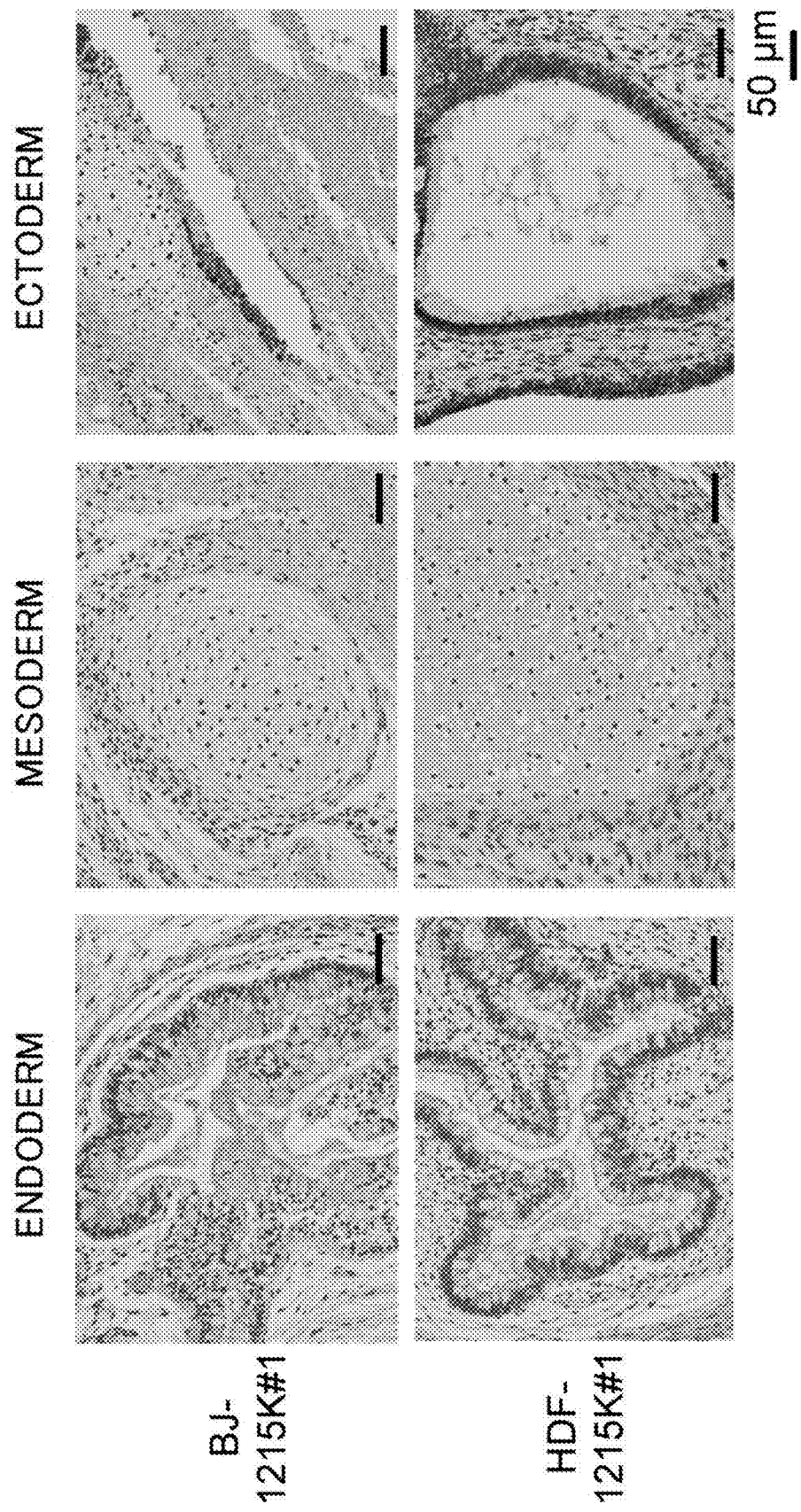
FIG. 9 shows the in vivo pluripotency of the induced artificial pluripotent stem cells.

Assessment of the In Vivo Pluripotency of the Induced Artificial Pluripotent Stem Cells The in vivo pluripotency was confirmed by teratoma formation in immunocompromised mice. The BJ cell-derived iPS cell clone BJ-1215K#1 or the HDF cell-derived iPS cell clone HDF-1215K#1 was inoculated subcutaneously to SCID mice, and tumor mass formation was confirmed about one month later. Approximately 2 months later, specimens were harvested, fixed in 10% formalin and embedded in paraffin. The tissue sections were stained with hematoxylin and eosin, and triploblastic differentiation was confirmed (FIG. 9).

Example 11

Karyotype Analysis

Figure 10:
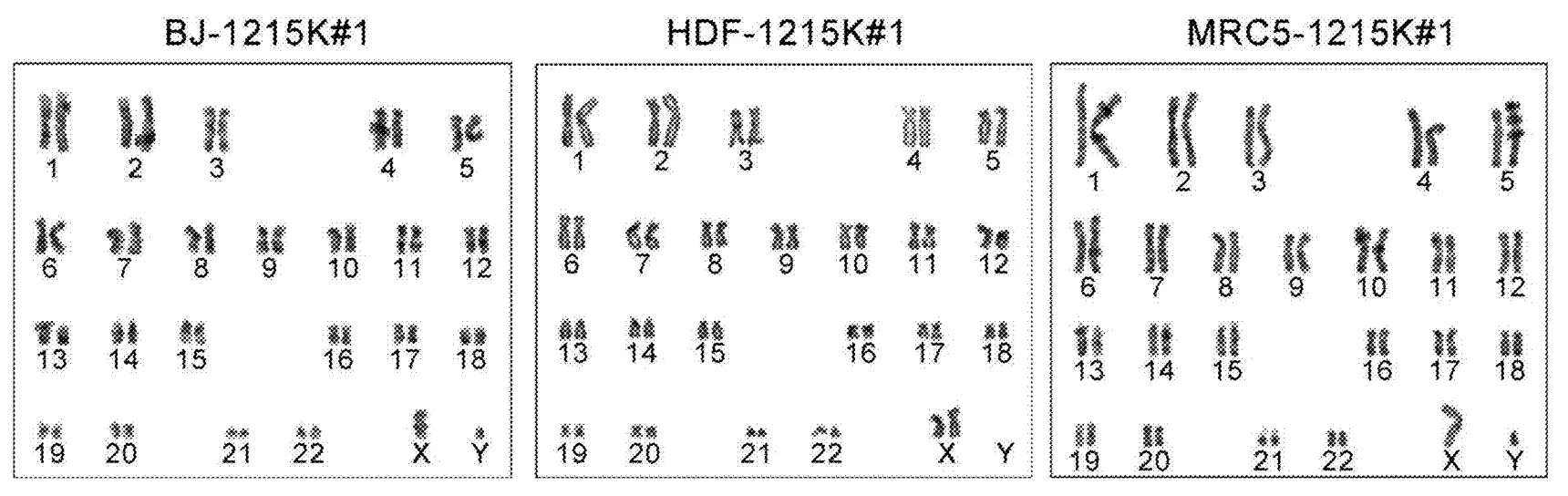

Karyotype analysis of the BJ cell-derived iPS cell clone BJ-1215K#1, the HDF cell-derived iPS cell clone HDF-12151K#1, and the MRC-5 cell-derived iPS cell clone MRC5-1215K#1 at the $9^{th}$ passage was performed in a request to Nihon Gene Research Laboratories Inc. The results showed that they have 46 chromosomes, and that the karyotype is normal (FIG. 10).

Example 12

Induction of iPS Cells from Mouse Fibroblasts

Figure 11:
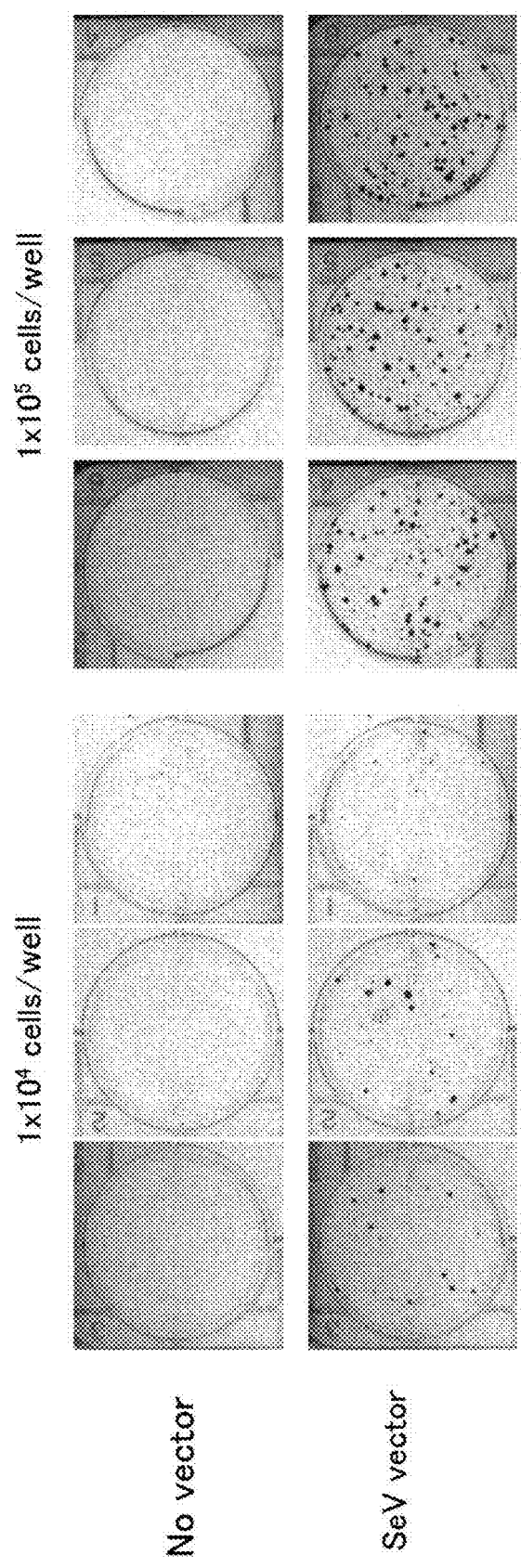
FIG. 11 shows induction of iPS cells from mouse fibroblasts (alkaline phosphatase-staining results).

Fibroblasts from 129+TER/SvJc1 mice were inoculated to a 6-well plate at $5\times10^5$ cells/well, and cultured overnight in a $CO_2$ incubator (37° C., 5% $CO_2$) Cells in the wells for cell count measurement were detached using a trypsin-EDTA solution, and the number of cells per well was measured. The amount of vector was calculated based on this cell count. Each of the SeV(PM)KOS/TS12ΔF vector, SeV(HNL)c-rMYC/TS15ΔF vector and SeV18+KLF4/TSΔF vector was added to the 10% FBS/PS/DMEM medium at MOI=5, and vector solutions were prepared to be 1 ml final solutions. The culture solution was removed from the 6-well plate, followed by addition of the prepared vector solutions, and culturing was carried out for about 24 hours in a $CO_2$ incubator (37° C., 5% $CO_2$). The cell culture solution was then removed, 1.0% FBS/PS/DMEM medium was added (2 mL/well), and culturing was carried out for about 24 hours in a $CO_2$ incubator (37° C., 5% $CO_2$). The cell culture solution was removed, the ES cell medium was added (the 2i medium was prepared by mixing 250 ml of an ES cell medium (Neurobasal medium; Life technologies, Cat. No. 21103-049), 250 ml of DMEM/F-12, GlutaMAX (Life technologies, Cat. No. 10565-018), 10 ml of B27 (Lite technologies, Cat. No. 17504044), 5 ml of N2 (Life technologies. Cat. No. 17502-048), 3.5 µl of 2-mercaptoethanol (Sigma, Cat. No. M3148-100ML), 2.5 ml of L-Glutamine (Life technologies, Cat. No. 25030-0841), 5 ml of penicillin-streptomycin (Nacalai Tesque, Cat. No. 26253-84), 100 µl of PD0325901 (prepared at 5 mM; Funakoshi, Cat. No. Axon1408), and 100 µl of CT 99021 (prepared at 15 mM; Funakoshi, Cat. No. Axon1.386) LIF (Millipore, Cat. No. ESG1106) was added to the 2i medium at a final concentration of 1000 U/ml, and this was used as a mouse ES cell medium (herein below referred to as 2i/LIF medium)), and culturing was carried out in a $CO_2$ incubator (37° C., 5% $CO_2$). Hereinafter until day 5 of the vector infection, the culturing was carried out while exchanging the medium with the 2i/LIF medium. On day 5 of the infection, feeder cells were inoculated into 6-well plates coated with a 0.1% gelatin solution at 1.4×10$^5$ cells/well/2 ml 10% FBS/PS/DMEM and 10 cm dishes at 7×10$^5$ cells/dish/10 ml 10% FBS/PS/DMEM, and they were cultured in a $CO_2$ incubator (37° C., 5% $CO_2$). On day 6 of the infection, vector-infected cells were detached using trypsin-EDTA, the 2i/LIF medium was added to prepared feeder cells, cells were plated into 6-well plates at a proportion of 1×10$^4$ cells/well and 1×10$^5$ cells/well or into 10 cm dishes at a proportion of 1×10$^4$ cells/dish and 1×10$^5$ cells/dish, and cultured in a $CO_2$ incubator (37° C., 5% $CO_2$). After this, induction of iPS cells was carried out with medium exchange with the 2i/LIF medium almost everyday. On day 21 of the infection, alkaline phosphatase staining was carried out (FIG. 11). iPS cell-like alkaline phosphatase-positive cells were measured, and the resulting induction efficiency was about 0.1%.

Example 13

Obtaining Clones of Mouse iPS Cells

Figure 12:
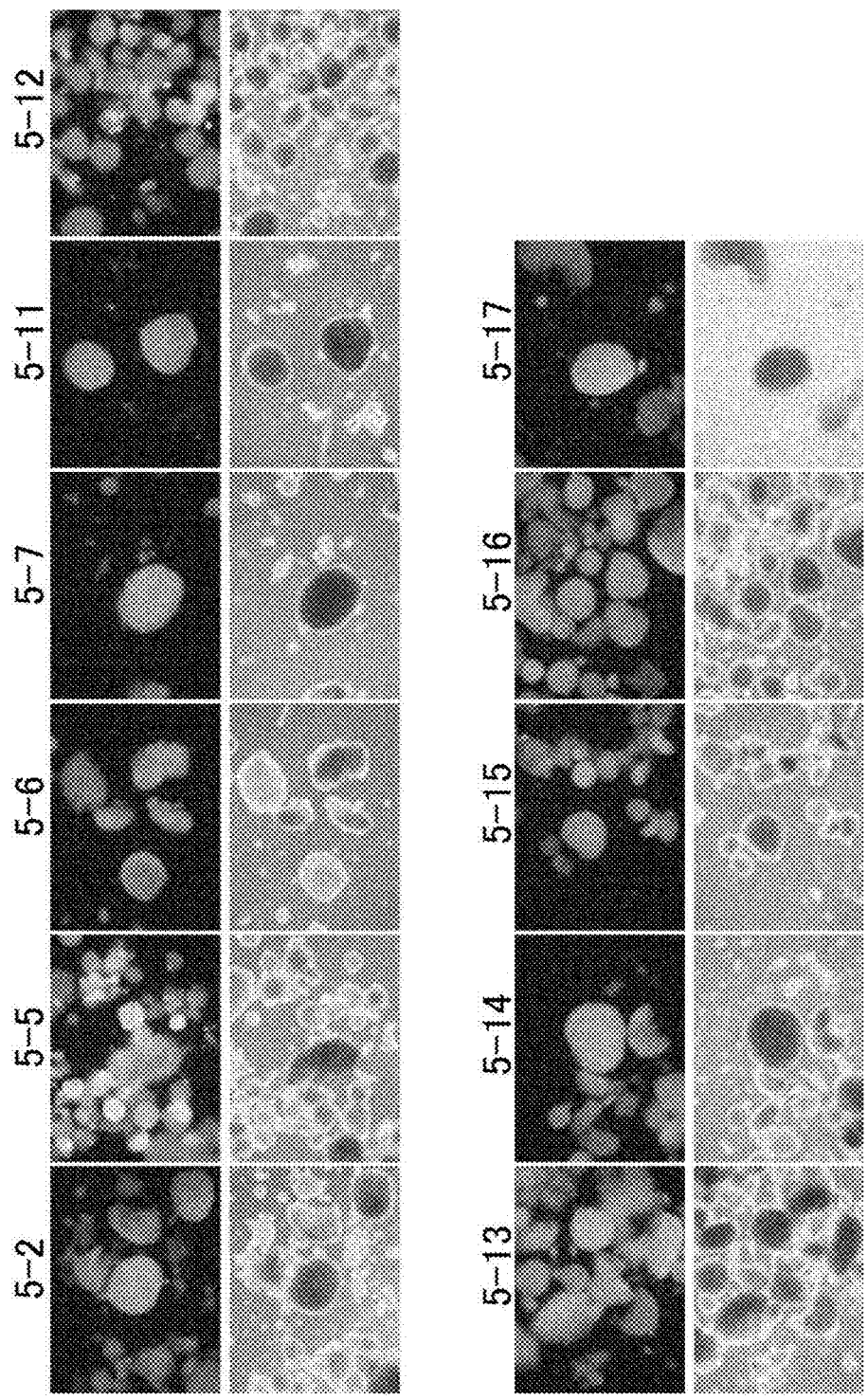
FIG. 12 shows confirmation of vector removal by anti-Sendai virus antibody staining.

From the 10 cm dishes with cells seeded at 1×10$^4$ cells/dish and 1×10$^5$ cells/dish in Example 12, 6 clones and 18 clones were picked up, respectively, on day 16 of the infection, and they were passaged and cultured. Removal of the Sendai virus vector was confirmed by staining with an anti-SeV antibody (FIG. 12). The results shows that nine Sendai virus vector-negative clones were obtained (clone numbers: 5-2, 5-6, 5-7, 5-11, 5-13, 5-14, 5-15, 5-16 and 5-17).

Example 14

Gene Expression Analysis by Immunostaining

Figure 13:
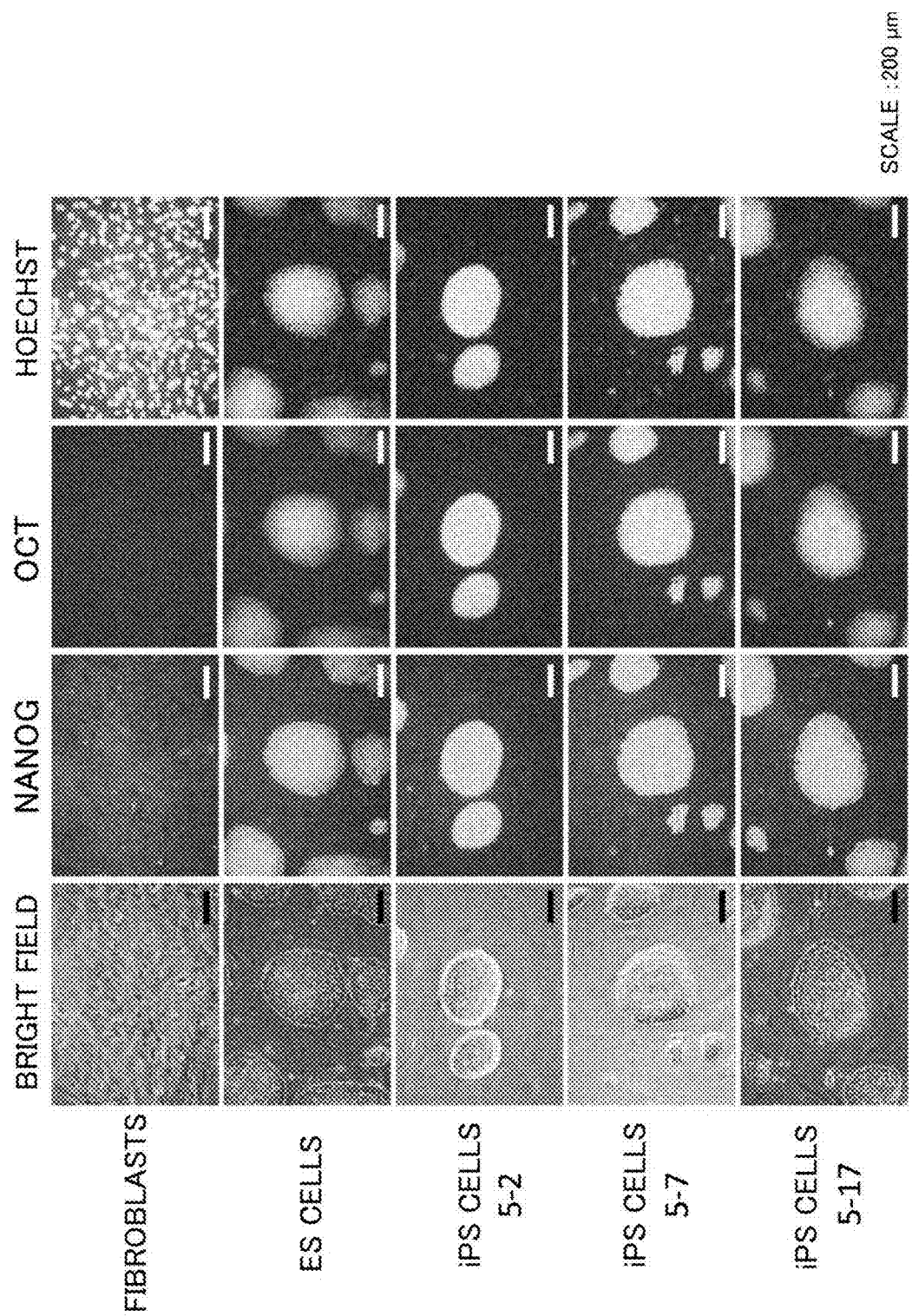
FIG. 13 shows confirmation of the marker gene expression by inimmunostaining.

The mouse iPS cells that were induced in Example 12 and confirmed to be negative of the Sendai virus vectors in Example 13 were assessed by immunostaining with an anti-NANOG antibody and an anti-OCT4 antibody (FIG. 13). The results show that NANOG and OCT4 of three iPS cell clones (5-2, 5-7 and 5-17) were stained similarly as mouse ES cells, which are the positive control. NANOG and OCT4 of mouse fibroblasts, which are the negative control, were not stained. Accordingly, the assessed iPS cells were shown to be expressing the NANOG and OCT4 genes at the protein level.

Example 15

Assessment of Pluripotency

Mouse iPS cells that were induced in Example 12 and confirmed to be negative of the Sendai virus vectors in Example 13 were assessed for their pluripotency.

Figure 14:
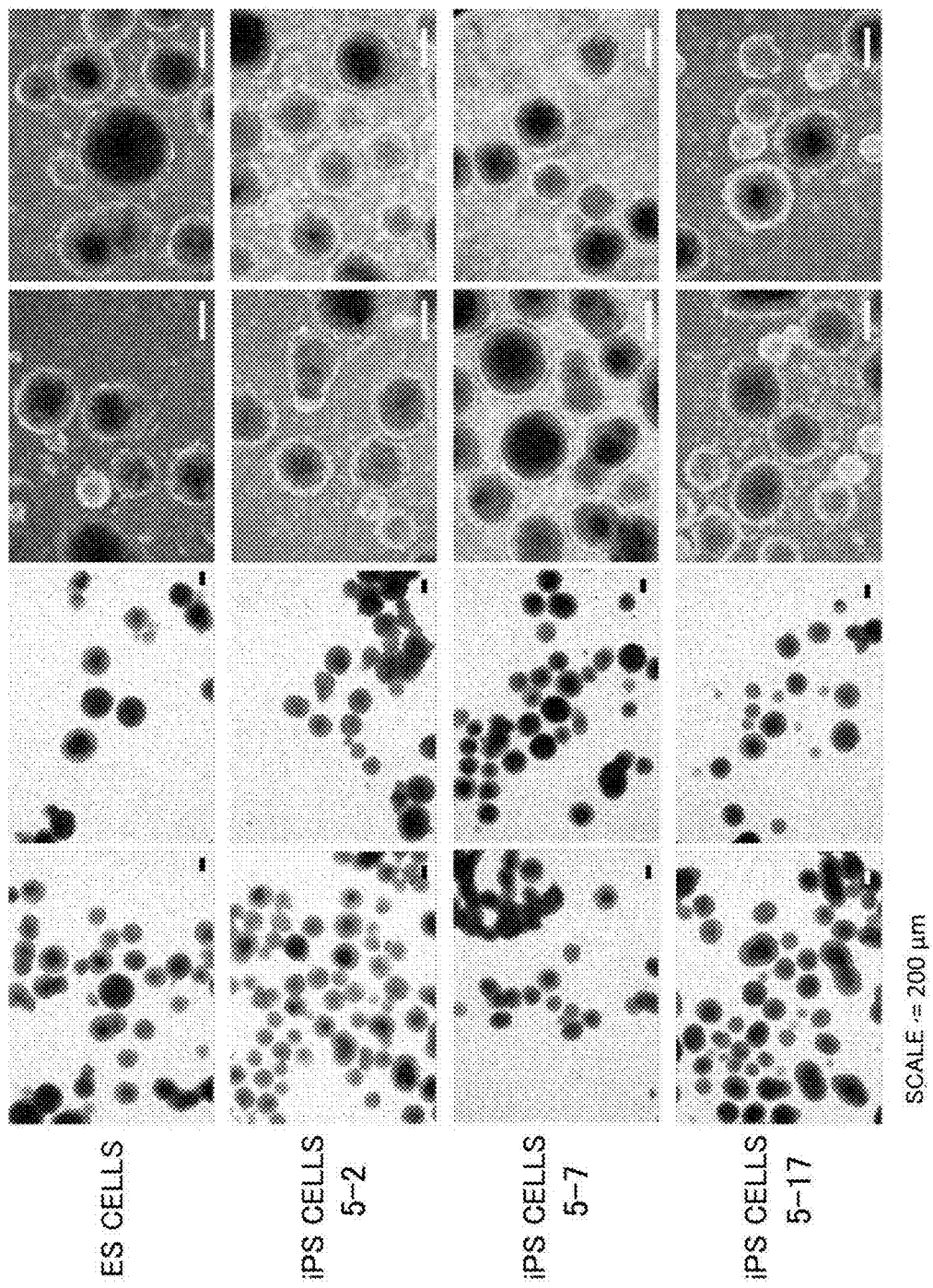
FIG. 14 shows results of the assessment of mouse iPS cells (embryoid body formation).

Embryoid bodies were formed by culturing in a serum medium that does not contain LIF (FIG. 14). The same was with mouse ES cells.

Figure 15:
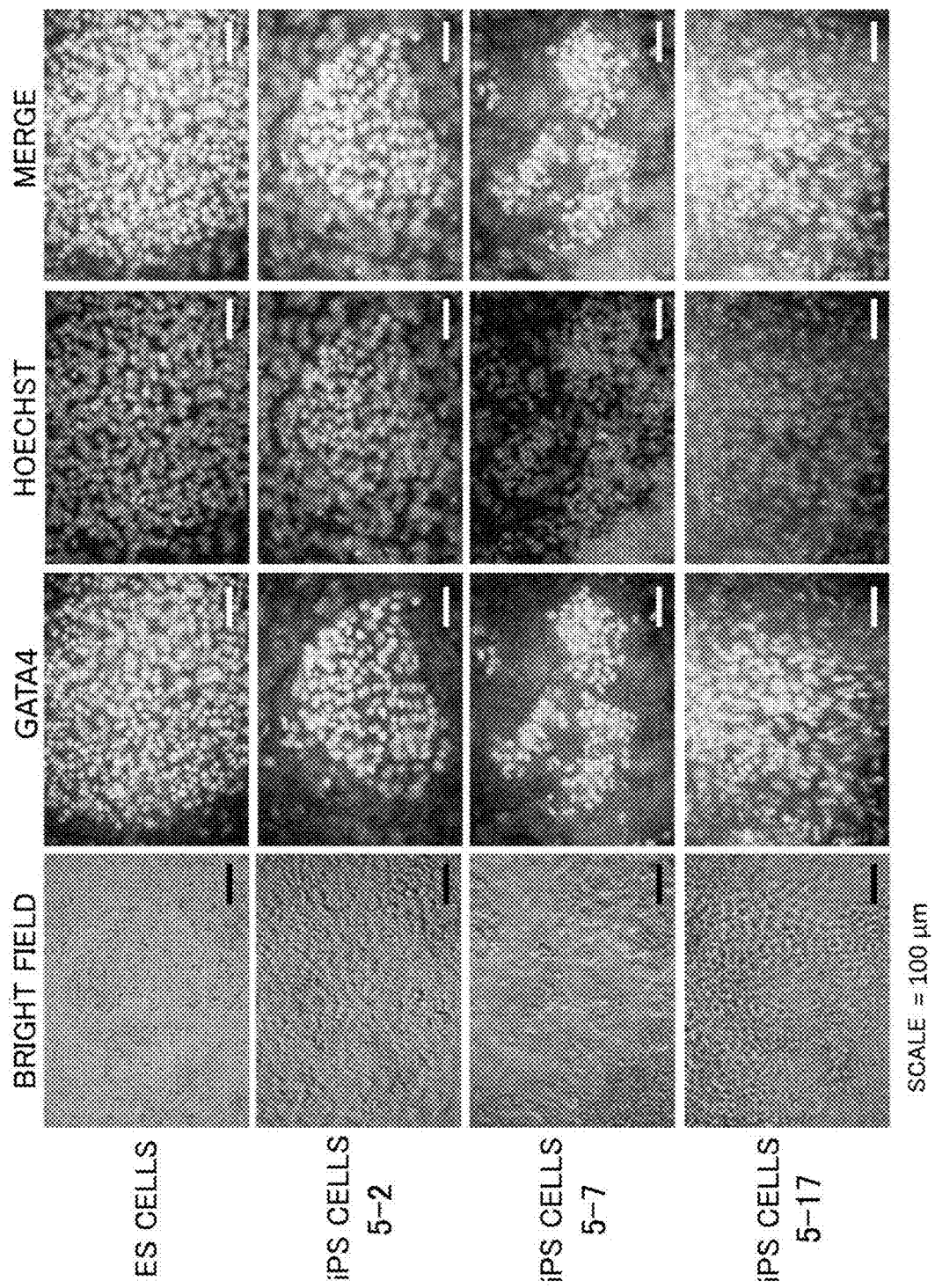
FIG. 15 shows results of the assessment of mouse iPS cells (in vitro differentiation into endoderm).

After embryoid body formation, the cells were passaged in gelatin-coated plates and cultured in a serum medium containing no LIF, and the cellular nucleus was stained by GATA4 (a transcription factor which is a marker of the endoderm) staining on day 4 (FIG. 15).

Figure 16:
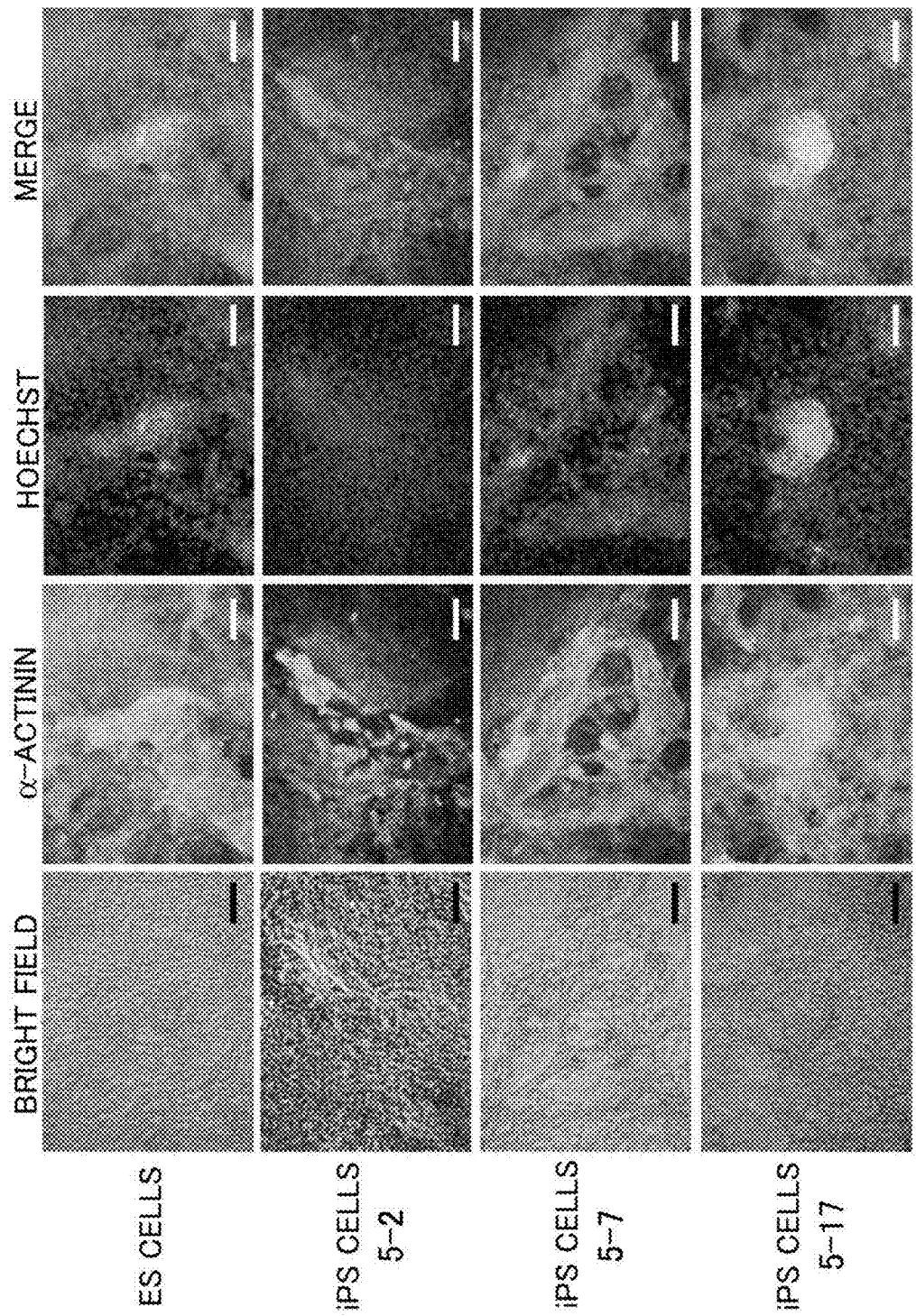
FIG. 16 shows results of the assessment of mouse iPS cells (in vitro differentiation into mesoderm).

Culturing was continued in a serum medium containing no LIF, and passaging was done in gelatin-coated plates. On day 10, tissues that are thought to be pulsating cardiac muscles were observed. On day 14, the cells were fixed and immunostained using an antibody against α-Actinin (FIG. 16). The cells were stained overall. Among them, cells strongly stained were observed in some regions.

Figure 17:
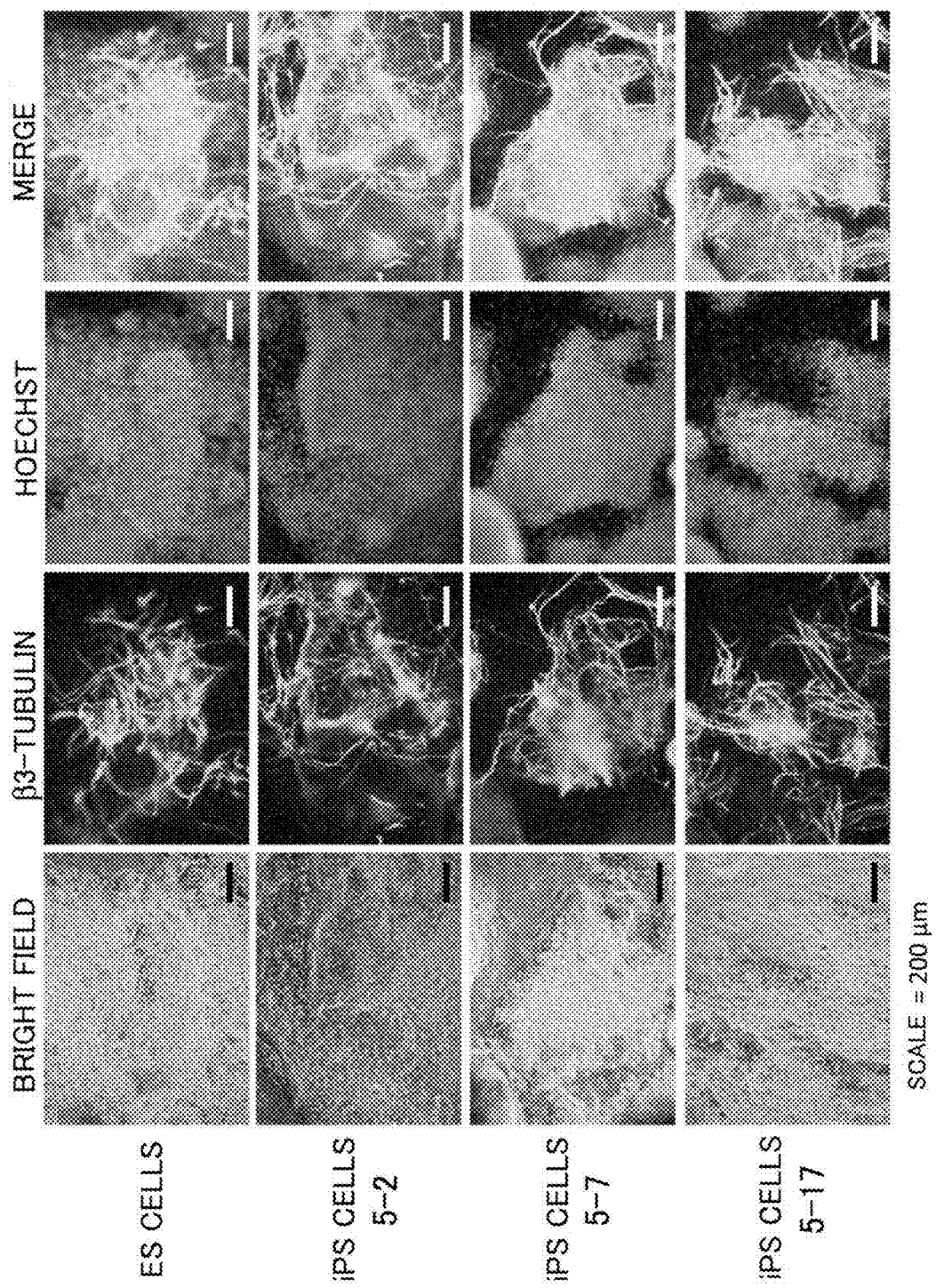
FIG. 17 shows results of the assessment of mouse iPS cells (in vitro differentiation into ectoderm).
Figure 18:
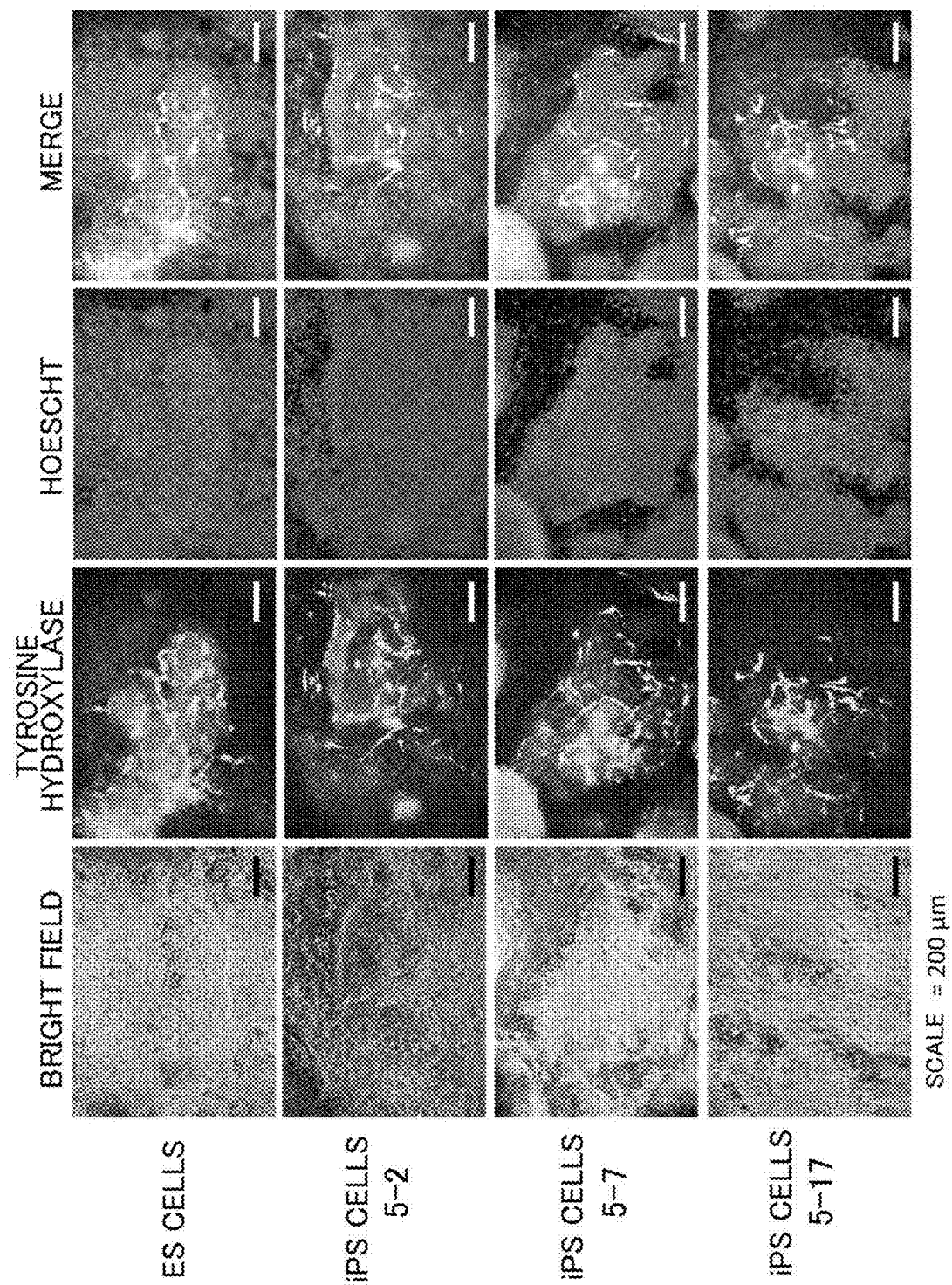
FIG. 18 shows results of the assessment of mouse iPS cells (in vitro differentiation into ectoderm).

On day 4 of culturing in a 2i medium containing no LIF and passaging in gelatin-coated plates, differentiation into nerve cells that are βIII tubulin-positive (FIG. 17) and tyrosine hydroxylase-positive (FIG. 18) was shown. These results showed that it is possible to induce from mouse cells, iPS cells that have triploblastic differentiation ability by using the Sendai virus vectors of the present invention.

Example 16

Induction of iPS Cells from Human Monocytes –1

Induction of iPS cells from human CD14+ monocytes was performed. The monocytes used were purchased from LONZA (Cat. No. 2W-400C). The monocytes were cultured in IMDM containing 10% Fetal Bovine Serum and penicillin-streptomycin (hereinafter referred to as 10% FBS/PS/IMDM). The frozen monocyte cells were thawed in a 37° C. water bath, transferred to 50 ml Falcon tubes containing 10 ml of 10% FBS/PS/IMDM, and mixed gently. After centrifugation at 100 g, 5 minutes, room temperature, the supernatant was removed, and 10 ml of 1.0% FBS/PS/EVIDM was added and mixed. The cell number was counted using a hemocytometer. The cells were inoculated into 6-well plates at 5×10$^5$ cells/well/2 ml 10% FBS/PS/IMDM, and cultured in a $CO_2$ incubator (37° C., 5% $CO_2$).

Figure 19:
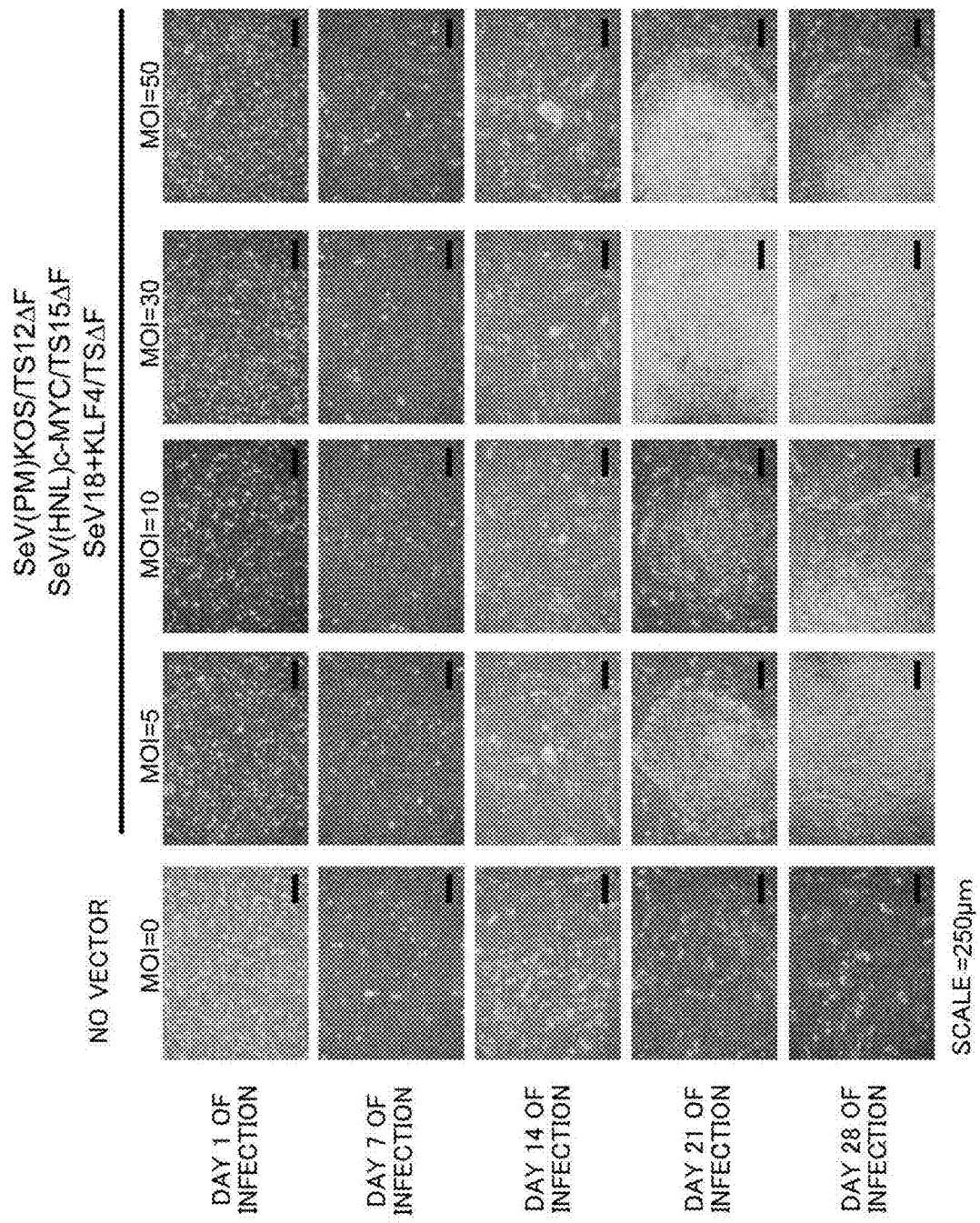
FIG. 19 shows induction of iPS cells from human monocytes.
Figure 20:
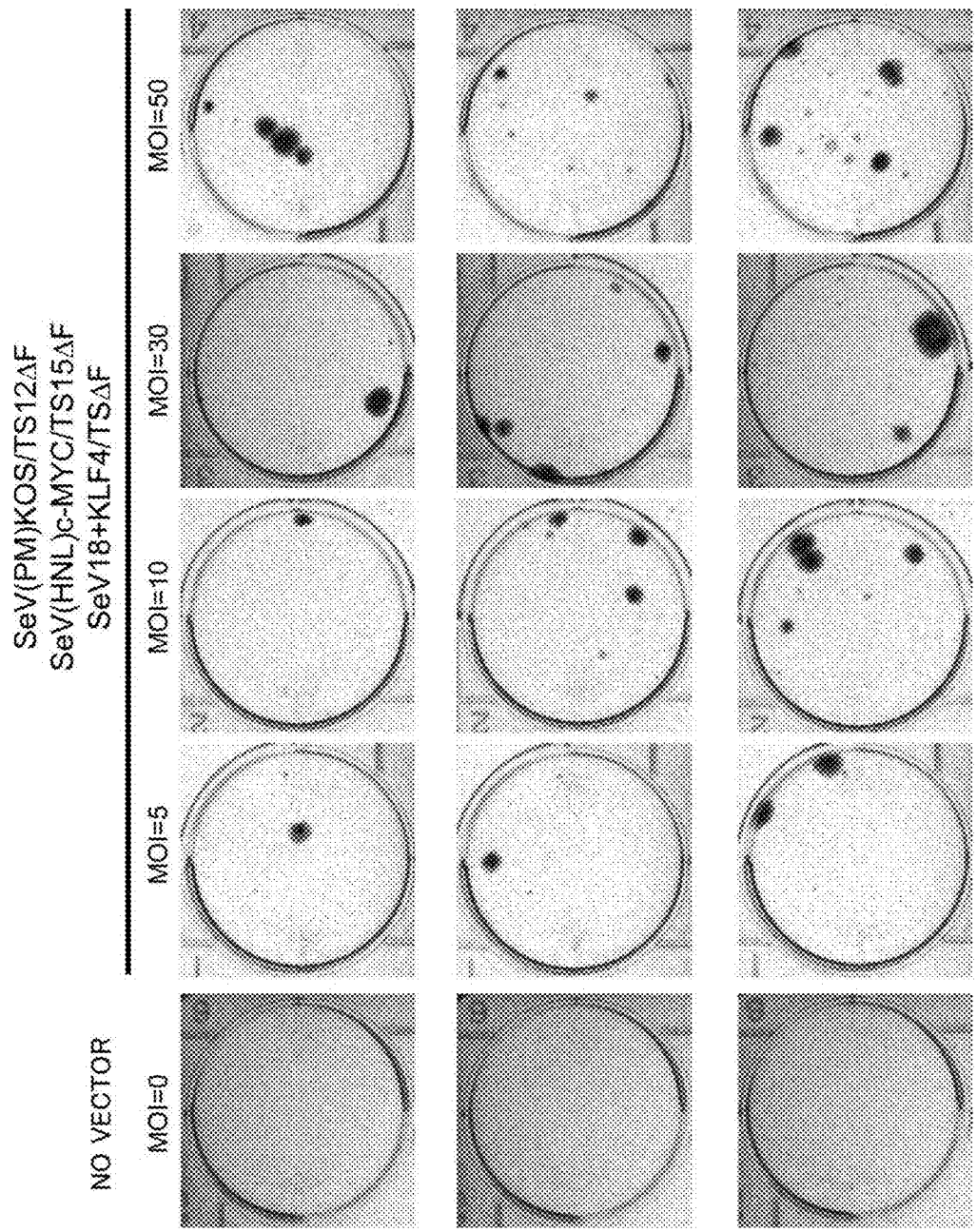
FIG. 20 shows induction of iPS cells from human monocytes (alkaline phosphatase-staining images).
Figure 21:
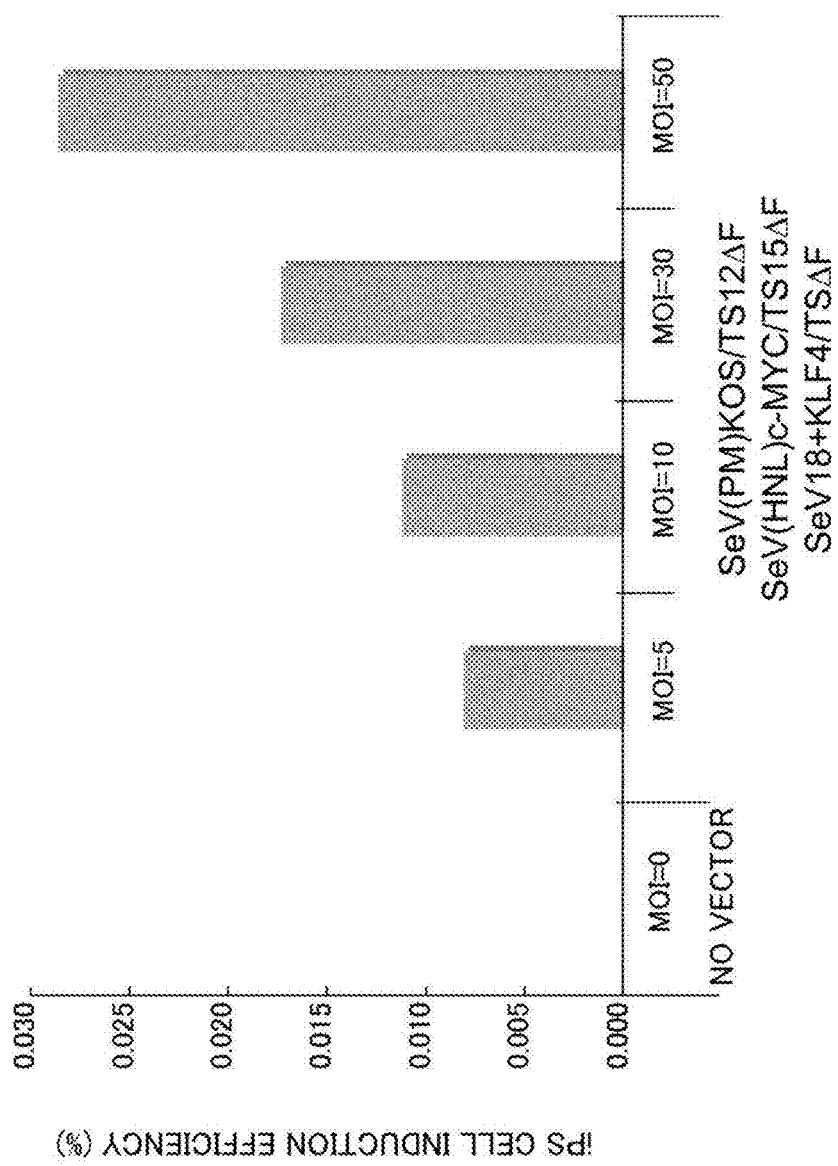
FIG. 21 shows induction of iPS cells from human monocytes (efficiency of iPS cell induction).

After collection of the cells in Eppendorf tubes and centrifugation, the supernatant was removed, 500 µl of 10% FBS/PS/IMDM was added and mixed, and the cell number was counted. The amount of vector required was calculated from the cell number, and vectors solutions were prepared as vector solutions with a final volume of 500 µl, by mixing 10% FBS/PS/IMDM with three types of vectors: SeV(PM) KOS/TS12ΔF vector, SeV(HNL)c-rMYC/TS15ΔF vector and SeV18+KLF4/TSΔF vector so that the MOI becomes 5, 10, 30 and 50. The cell solution and the vector solutions were mixed and added to 6-well plates, and cultured overnight in a CO2 incubator (37° C., 5% $CO_2$). Next day, 10% FBS/PS/IMDM was added at 1 ml/well, and the cells were cultured for two days in a CO2 incubator (37° C., 5% $CO_2$). The medium was exchanged with 10% FBS/PS/IMDM until day 3 and day 4 of the infection. The cells were detached using trypsin-EDTA on day 6 of the infection, suspended in 10% FBS/PS/IMDM, added onto the feeder cells, and cultured in a $CO_2$ incubator (27° C., 5% $CO_2$). Next day, the medium was exchanged with a primate ES cell medium (ReproCell, IRCHEMD001) with an addition of bFGF at 4 ng/ml. Then, culturing was continued until day 28 of the vector infection with medium exchange. The state of the cells during the induction process is shown in FIG. 19. On day 28, alkaline phosphatase staining was carried out, and induction of alkaline phosphatase-positive colonies was observed (FIG. 20). The efficiency of iPS cell induction became higher in a manner dependent on the vector quantity, and was about 0.01% to 0.03% (FIG. 21).

Example 17

Induction of iPS Cells from Human Peripheral Blood Mononuclear Cells

Figure 22:
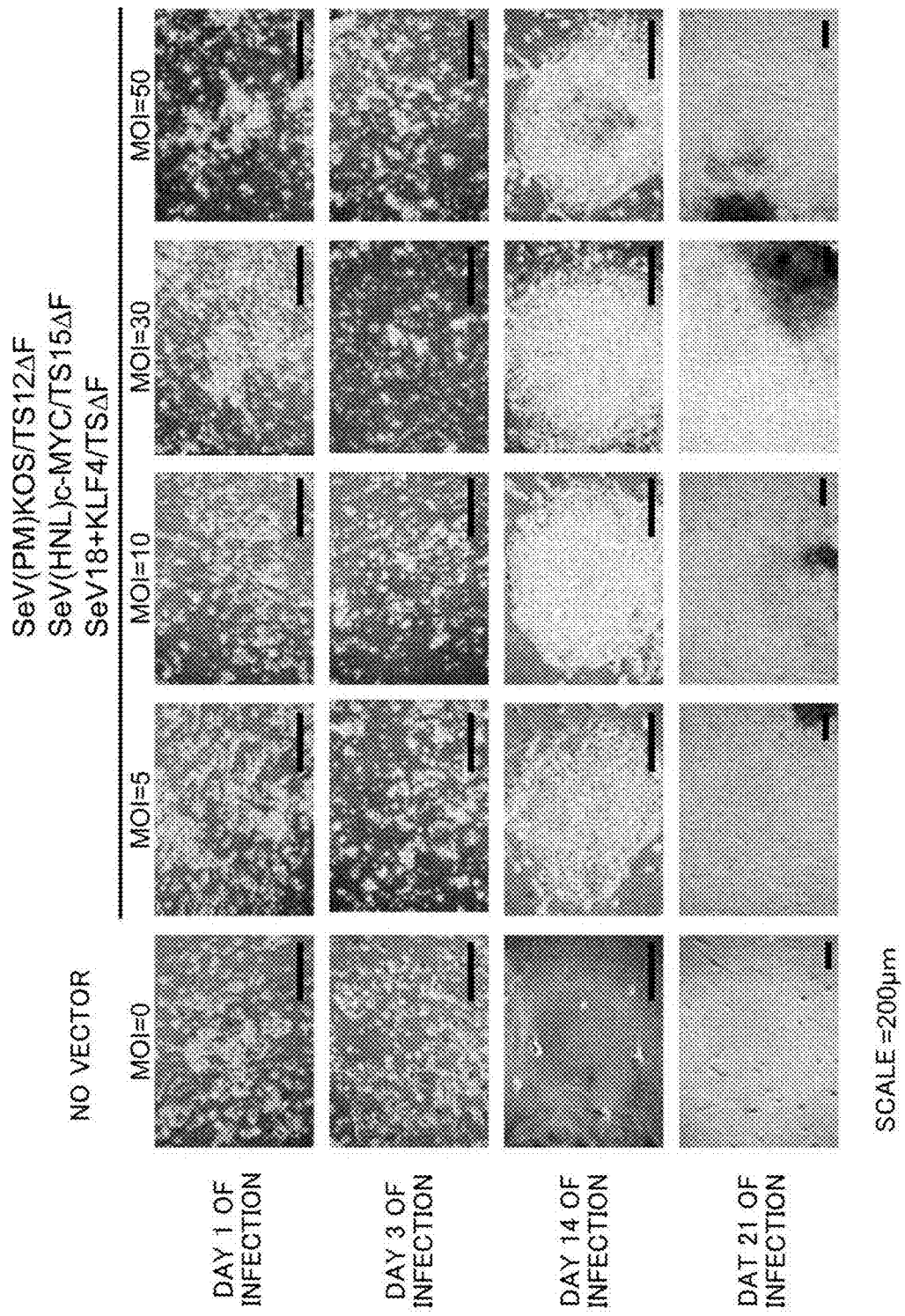
FIG. 22 shows induction of iPS cells from human peripheral blood mononuclear cells (appearance of cells of Donor 1).
Figure 23:
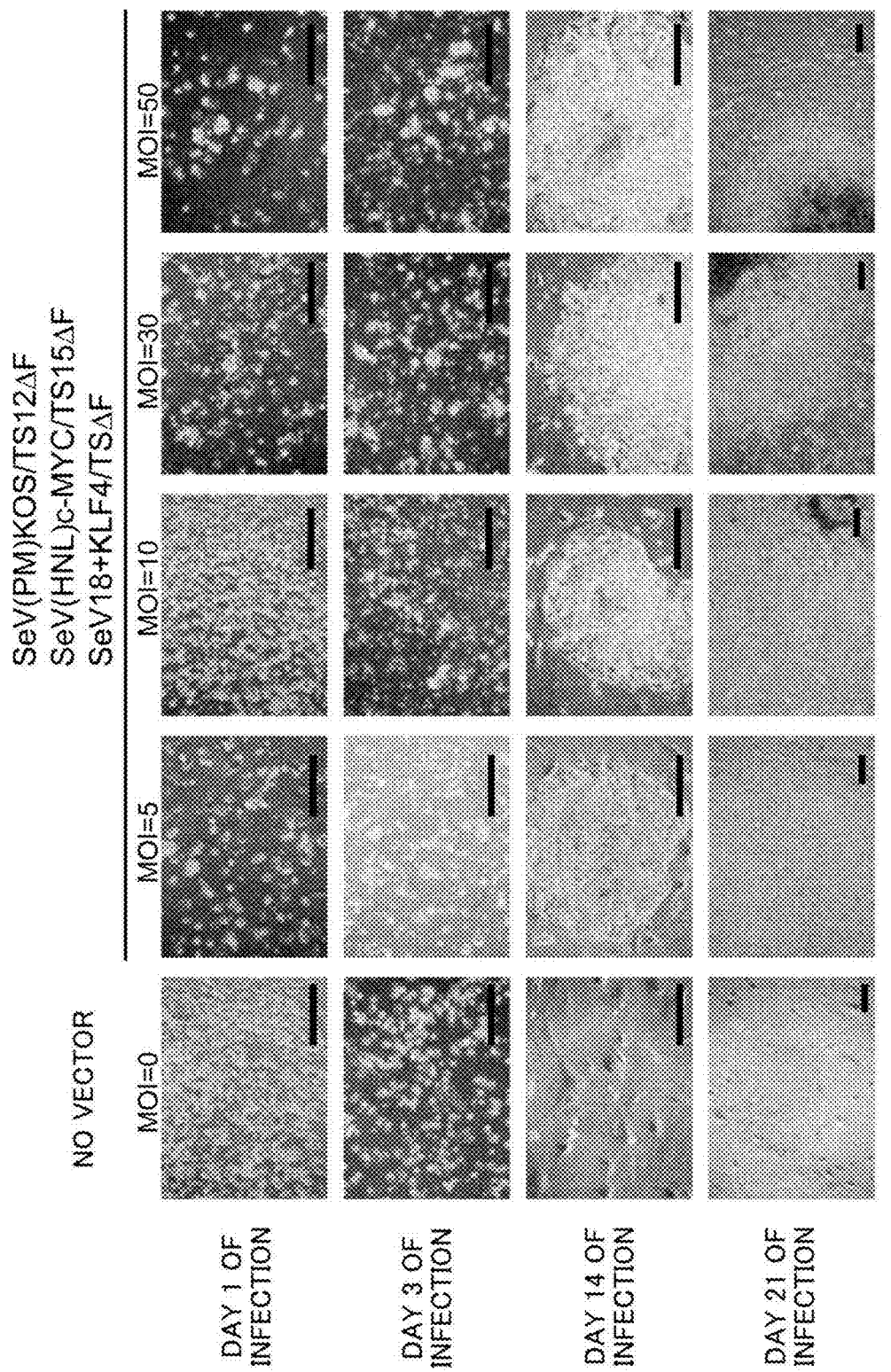
FIG. 23 shows induction of iPS cells from human peripheral blood mononuclear cells (appearance of cells of Donor 2).
Figure 24:
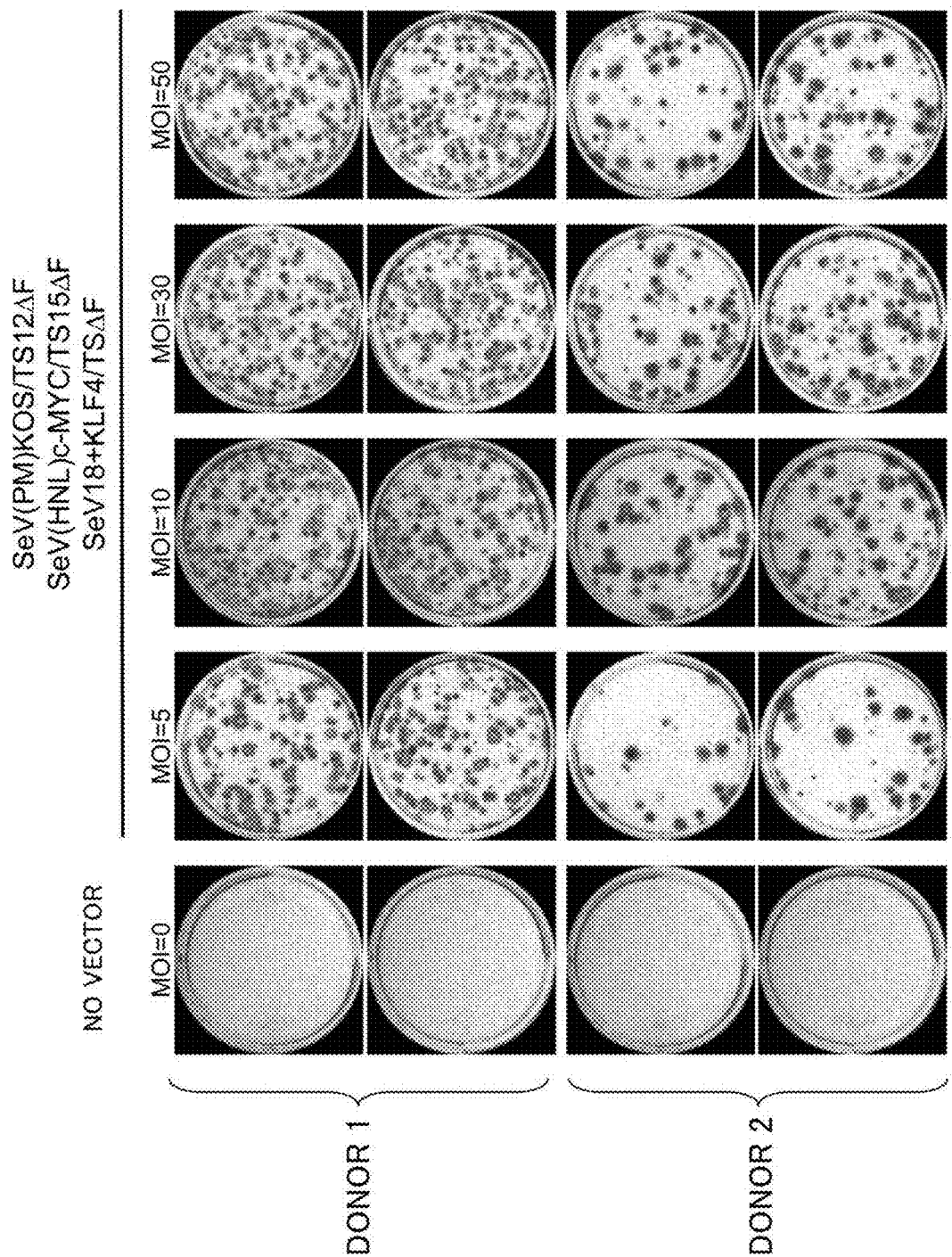
FIG. 24 shows induction of iPS cells from human peripheral blood mononuclear cells (alkaline phosphatase staining).
Figure 25:
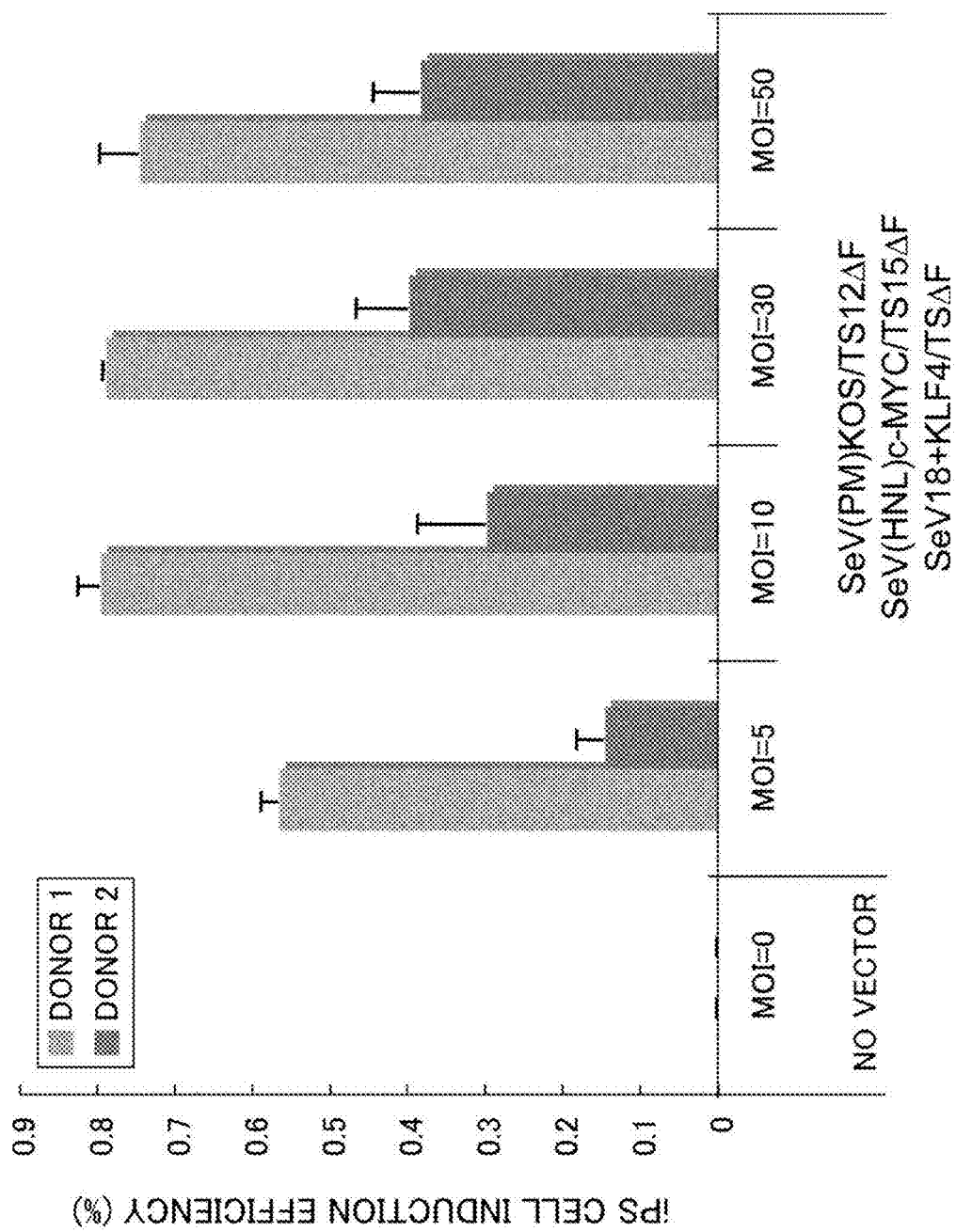
FIG. 25 shows induction of iPS cells from human peripheral blood mononuclear cells (induction efficiency).

Peripheral blood mononuclear cells were prepared by the Ficoll method from blood provided by two volunteers (as Donors 1 and 2). Culturing was carried out using a medium (PBMC+medium) prepared by adding cytokines (100 ng/mL SCF, 100 ng/mL FLT-3 Ligand, 20 ng/mL Thrombopoetin, 10 ng/mL IL-6) to the PBMC medium (medium prepared by adding StemPro-34 Nutrient, L-Glutamine and penicillin-streptomycin to StemPro-34 SFM). Vector infection was performed on day 4 of the culturing. The cell number of peripheral blood mononuclear cells was measured, and the vector quantity was calculated so that the MOI becomes 5, 10, 30 and 50. Vector solutions were prepared by adding the calculated vectors to the PBMC+ medium. After removal of the PBMC culture solution and addition of the vector solutions, the cells were cultured in a $CO_2$ incubator (37° C., 5% $CO_2$). The cells were detached using trypsin-EDTA on day 3 of the vector infection, suspended in the PBMC-H medium, added onto the feeder cells, and cultured in a $CO_2$ incubator (37° C., 5% $CO_2$). From the next day until day 6 of the infection, the medium was exchanged with the PBMC medium, and the cells were cultured in a CO2 incubator (37° C., 5% CO2). On day 7 of the infection, half of the medium was removed, and an equivalent amount of a primate ES cell medium (ReproCell, RCHEMD001) with an addition of bFGF at 4 ng/ml was added, and the cells were cultured in a $CO_2$ incubator (27° C., 5% $CO_2$). After this, culturing was done using the primate ES cell medium (ReproCell, RCHEMD001) with an addition of bFGF at 4 ng/ml, and iPS-like cells were observed on day 21 of the infection (FIG. 22 and FIG. 23). Then, alkaline phosphatase staining was carried out (FIG. 24). The results of calculating the efficiency of inducing alkaline phosphatase-positive iPS-like cells showed that an induction efficiency of 0.1%-0.8% was achieved, although the induction efficiency differed depending on the donor and the amount of vector (FIG. 25).

Example 18

Induction of iPS Cells from Human Monocytes-2

Figure 26:
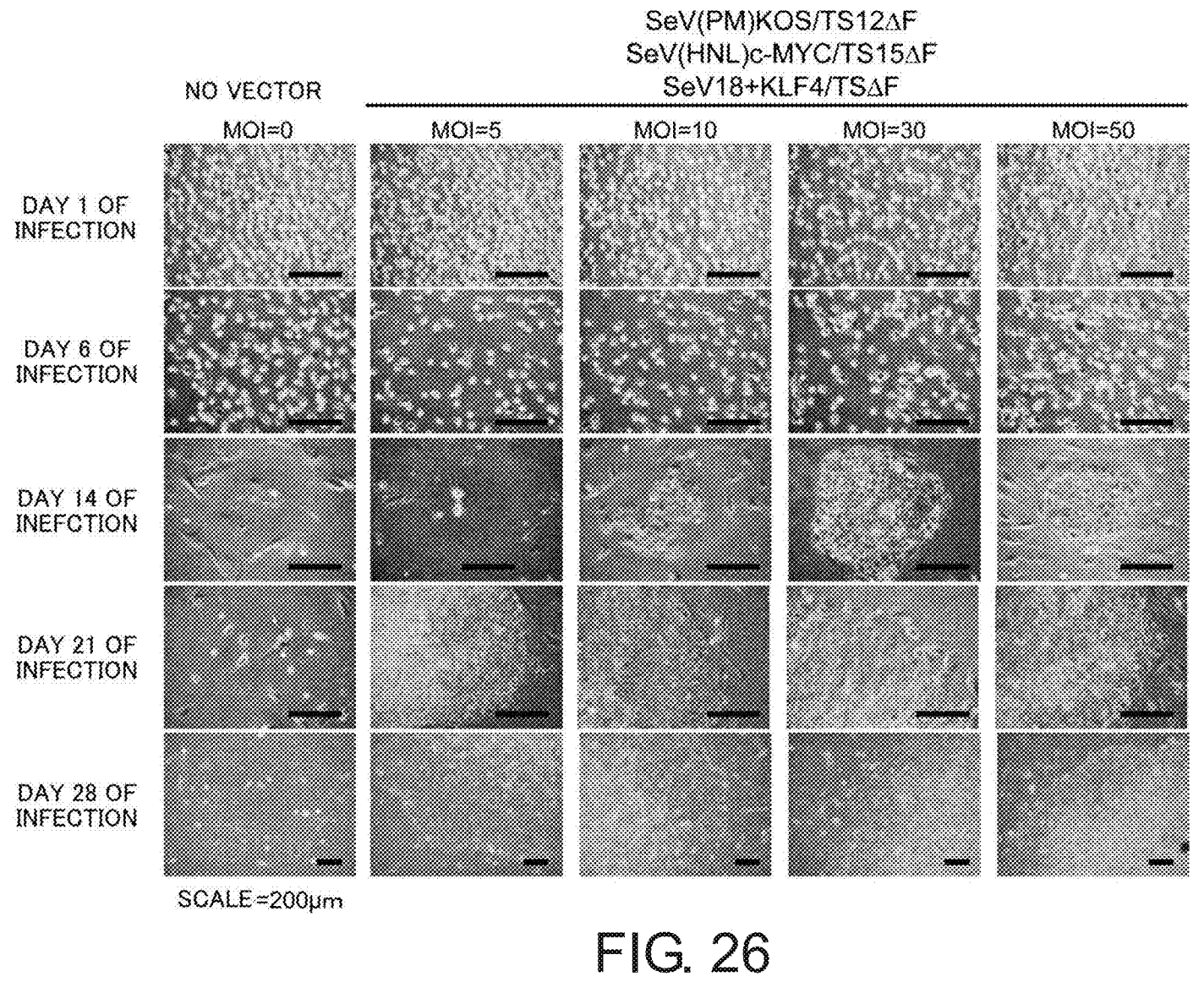
Figure 27:
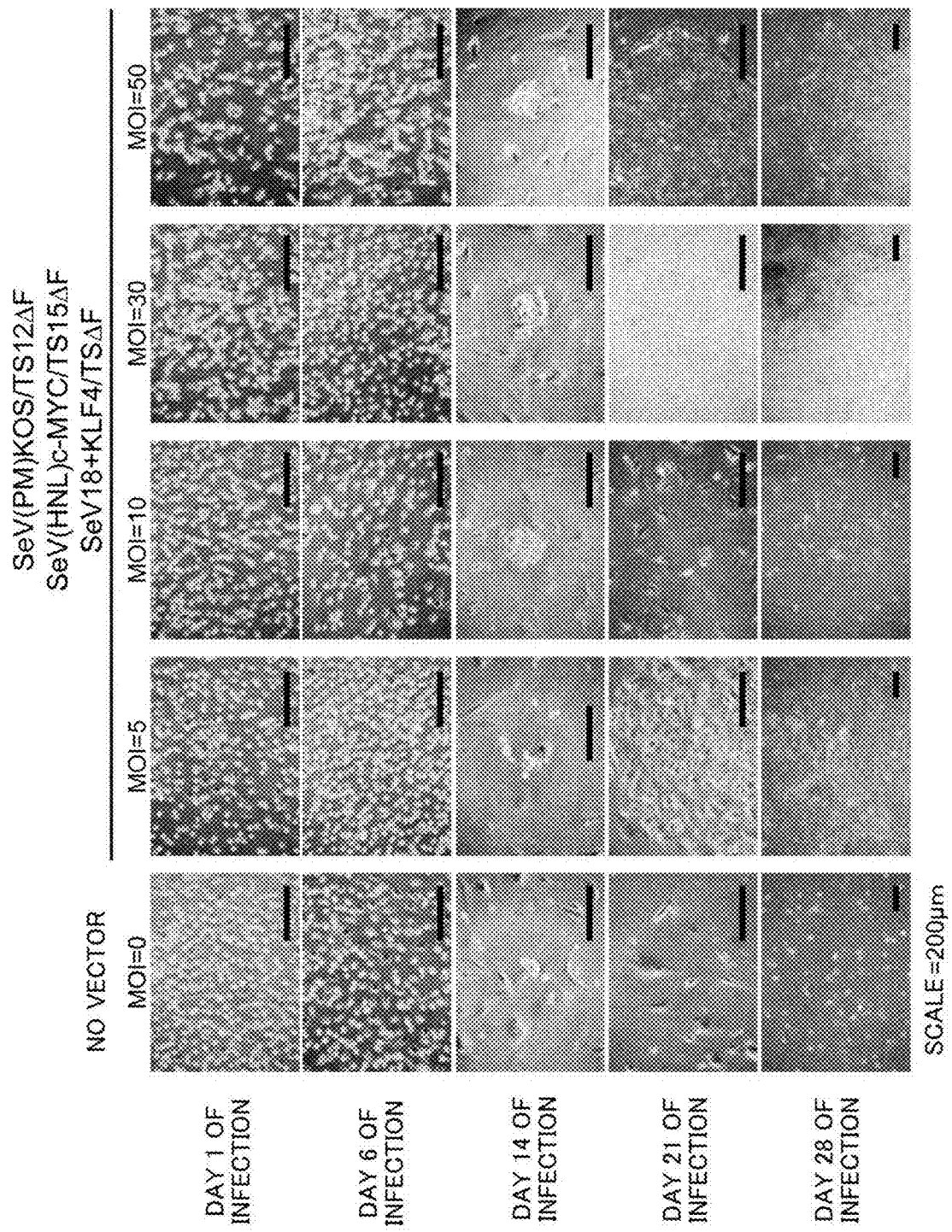
FIG. 27 shows induction of iPS cells from human monocytes (appearance of cells of Donor 4).
Figure 28:
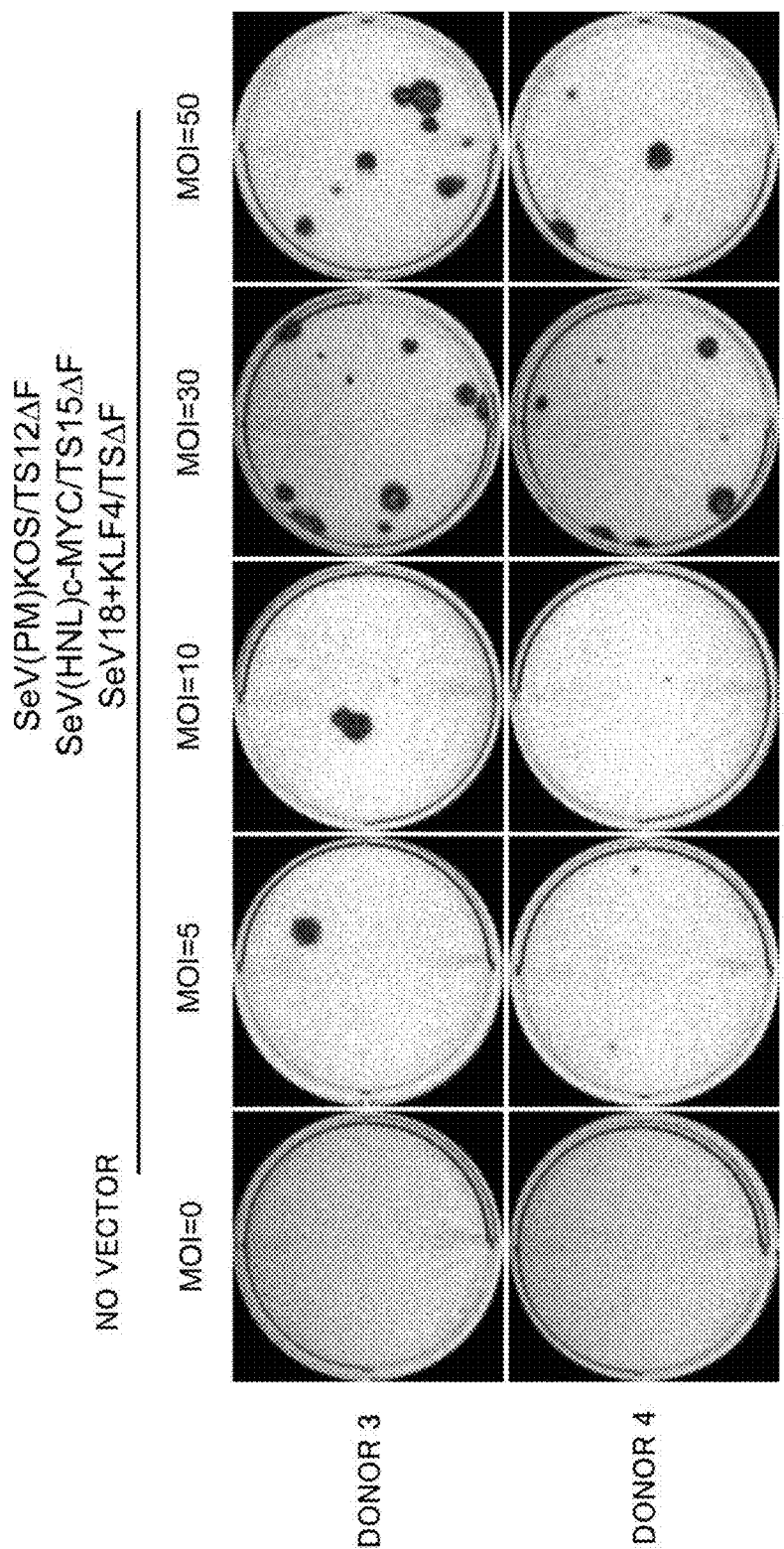
FIG. 28 shows induction of iPS cells from human monocytes (alkaline phosphatase staining).
Figure 29:
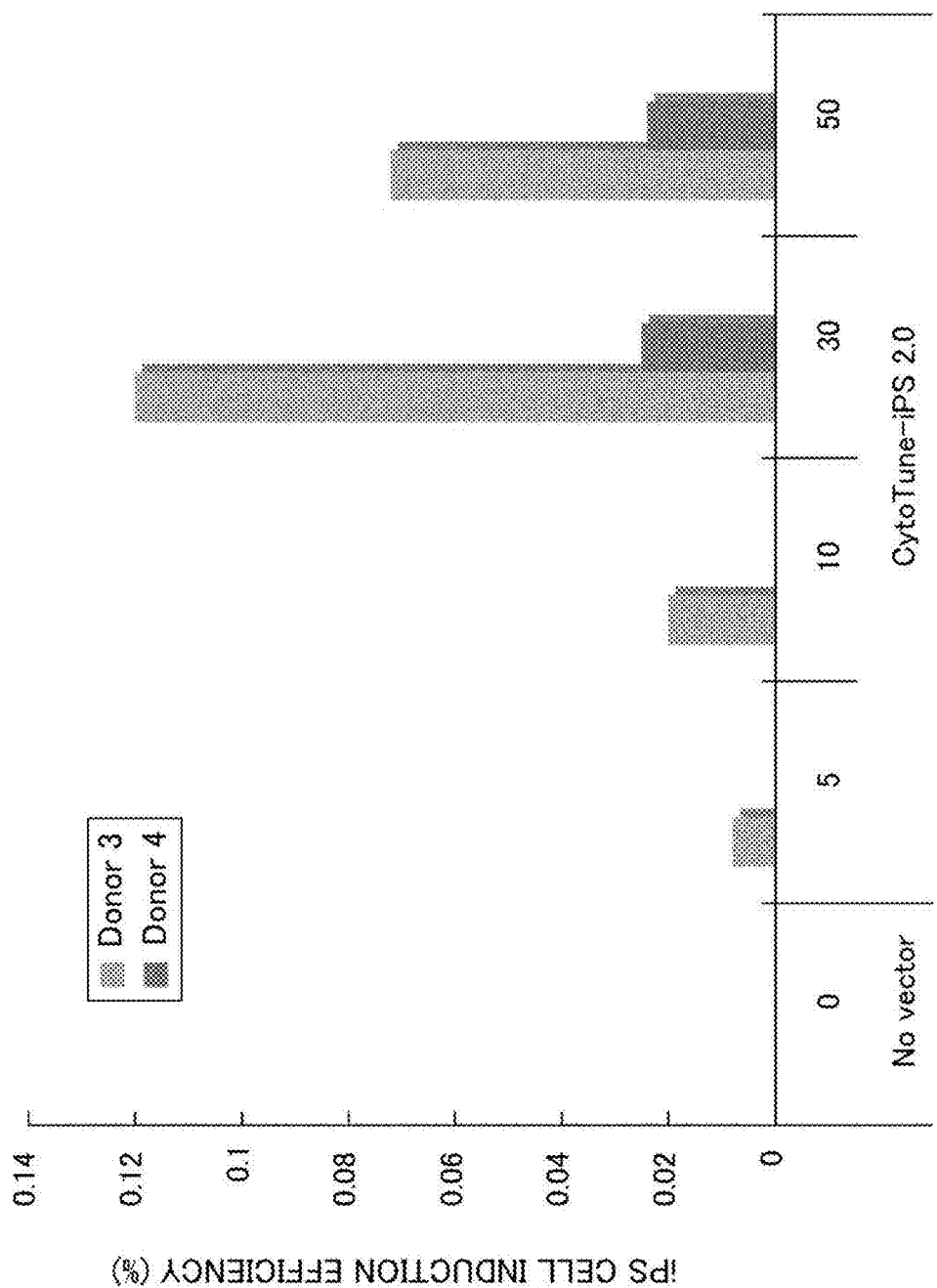
FIG. 29 shows induction of iPS cells from humonocytes (induction efficiency).

Peripheral blood mononuclear cells were prepared by the Ficoll method from blood provided by two volunteers (as Donors 3 and 4). From these peripheral blood mononuclear cells, CD14+ cells were separated as the starting material by using the EasySep positive selection Human CD14 positive Selection kit (Veritas, Cat. No. 18058). By FACS analysis using an anti-CD14 antibody, about 15% of the peripheral blood mononuclear cells were CD14-positive and it was confirmed that after separation, the purification was improved to 85% or above. These cells were infected with three types of vectors: SeV(PM)KOS/TS12ΔF vector, SeV (HNL)c-rMYC/TS15ΔF vector and SeV18+KLF4/TSΔF vector so that the MOI becomes 5, 10, 30 and 50, and induction of iPS cells was carried out by the same method as shown in Example 16. These results confirmed induction of alkaline phosphatase stain-positive iPS-like cells (FIG. 26, FIG. 27, FIG. 28), and the induction efficiency was 0.12% at maximum (FIG. 29).

INDUSTRIAL APPLICABILITY

By the present invention, i is possible to significantly improve the induction efficiency of pluripotent stem cells by using a vector that contains the KLF gene, OCT gene, and SOX gene in this order. It is useful that pluripotent stem cells can be induced with high efficiency without low-temperature culturing, and use of a temperature-sensitive vector, in particular, enables prompt vector removal in induction of pluripotent stem cells. With the methods of the present invention, one can expect to obtain more physiologically favorable pluripotent stem cells because low-temperature stimulus is not applied to the cells.

The invention claimed is:

1. A method of improving efficiency of pluripotent stem cell induction in a method of inducing pluripotent stem cells without culturing at 36° C. or lower which comprises introducing:
   (i) a temperature-sensitive Sendai virus vector that comprises in one vector the KLF gene, OCT gene, and SOX gene in this order, wherein said Sendai virus vector is an F gene-deleted Sendai virus vector introduced with the following substitutions: G69E, T116A, and A183S mutations in the M protein, A262T, G264R, and K461G mutations in the HN protein, D433A, R434A, K437A, and L511F mutations in the P protein, and N1197S and K1795E mutations in the L protein,
   (ii) a Sendai virus vector that comprises the KLF gene but not the OCT gene or the SOX gene, wherein said Sendai virus vector is an F gene-deleted Sendai virus vector introduced with the following substitutions: G69E, T116A, and A183S mutations in the M protein, A262T, G264R, and K461G mutations in the HN protein, L511F mutation in the P protein, and N1197S and K1795E mutations in the L protein; and
   (iii) a temperature-sensitive Sendai virus vector inserted with a MYC gene, wherein said Sendai virus vector is an F gene-deleted Sendai virus vector introduced with the following substitutions: G69E, T116A, and A183S in the M protein, A262T, G264R, and K461G in the HN protein, D433A, R434A, K437A, and L511F in the P protein, and L1361C, L1558I, N1197S, and K1795E in the L protein.

2. The method of claim 1, wherein the culturing is carried out at about 37° C.

3. A composition for inducing pluripotent stem cells at 37° C., wherein the composition comprises:
   (a) a temperature-sensitive Sendai virus vector comprising in one vector the KLF gene, OCT gene and SOX gene in this order, which is an F gene-deleted Sendai virus vector introduced with the following substitutions: G69E, T116A and A183S mutations in the M protein, A262T, G264R and K461G mutations in the HN protein, D433A, R434A, K437A and L511F mutations in the P protein, and N1197S and K1795E mutations in the L protein;
   (b) a Sendai virus vector comprising the KLF gene but not the OCT gene or the SOX gene, which is an F gene-deleted Sendai virus vector introduced with the following substitutions: G69E, T116A and A183S mutations in the M protein, A262T, G264R and K461G mutations in the HN protein, L511F mutation in the P protein, and N1197S and K1795E mutations in the L protein, and
   (c) a temperature-sensitive Sendai virus vector inserted with a MYC gene, which is an F gene-deleted Sendai virus vector introduced with the following substitutions: G69E, T116A, and A183S in the M protein, A262T, G264R, and K461G in the HN protein, D433A, R434A, K437A, and L511 F in the P protein, and L1361C, L1558I, N1197S, and K1795E in the L protein;
wherein the composition further comprises a differentiated cell at 37° C. or higher; and
wherein the pluripotent stem cells are induced at 37° C. at an induction efficiency that is at least 2.7 fold greater in comparison to a composition that does not include the vector of (b).

* * * * *

SEQUENCE LISTING

```
<160> NUMBER OF SEQ ID NOS: 15

<210> SEQ ID NO 1
<211> LENGTH: 10
<212> TYPE: RNA
<213> ORGANISM: Artificial sequence
<220> FEATURE:
<223> OTHER INFORMATION: artificially synthesized sequence

<400> SEQUENCE: 1 ucccwvuuwc                                                         10

<210> SEQ ID NO 2
<211> LENGTH: 10
<212> TYPE: RNA
<213> ORGANISM: Artificial sequence
<220> FEATURE:
<223> OTHER INFORMATION: artificially synthesized sequence

<400> SEQUENCE: 2
ucccaguuuc                                                         10

<210> SEQ ID NO 3
<211> LENGTH: 10
<212> TYPE: RNA
<213> ORGANISM: Artificial sequence
<220> FEATURE:
<223> OTHER INFORMATION: artificially synthesized sequence

<400> SEQUENCE: 3
ucccacuuac                                                         10
```

```
<210> SEQ ID NO 4
<211> LENGTH: 10
<212> TYPE: RNA
<213> ORGANISM: Artificial sequence
<220> FEATURE:
<223> OTHER INFORMATION: artificially synthesized sequence

<400> SEQUENCE: 4
ucccacuuuc                                                             10

<210> SEQ ID NO 5
<211> LENGTH: 10
<212> TYPE: DNA
<213> ORGANISM: Artificial sequence
<220> FEATURE:
<223> OTHER INFORMATION: artificially synthesized sequence

<400> SEQUENCE: 5
agggtcaaag                                                             10

<210> SEQ ID NO 6
<211> LENGTH: 10
<212> TYPE: DNA
<213> ORGANISM: Artificial sequence
<220> FEATURE:
<223> OTHER INFORMATION: artificially synthesized sequence

<400> SEQUENCE: 6
agggtgaatg                                                             10

<210> SEQ ID NO 7
<211> LENGTH: 10
<212> TYPE: DNA
<213> ORGANISM: Artificial sequence
<220> FEATURE:
<223> OTHER INFORMATION: artificially synthesized sequence

<400> SEQUENCE: 7
agggtgaaag                                                             10

<210> SEQ ID NO 8
<211> LENGTH: 1317
<212> TYPE: DNA
<213> ORGANISM: Artificial sequence
<220> FEATURE:
<223> OTHER INFORMATION: artificially synthesized sequence
<220> FEATURE:
<221> NAME/KEY: CDS
<222> LOCATION: (1)..(1317)

<400> SEQUENCE: 8 atg ccc ctc aac gtt agc ttc acc aac agg aac tat gac ctc gac tac        48
Met Pro Leu Asn Val Ser Phe Thr Asn Arg Asn Tyr Asp Leu Asp Tyr
1               5                   10                  15 gac tcg gtg cag ccg tat ttc tac tgc gac gag gag gag aac ttc tac        96
Asp Ser Val Gln Pro Tyr Phe Tyr Cys Asp Glu Glu Glu Asn Phe Tyr
                20                  25                  30 cag cag cag cag cag agc gag ctg cag ccc ccg gcg ccc agc gag gat       144
Gln Gln Gln Gln Gln Ser Glu Leu Gln Pro Pro Ala Pro Ser Glu Asp
            35                  40                  45 atc tgg aag aaa ttc gag ctg ctg ccc acc ccg ccc ctg tcc cct agc       192
Ile Trp Lys Lys Phe Glu Leu Leu Pro Thr Pro Pro Leu Ser Pro Ser
        50                  55                  60 cgc cgc tcc ggg ctc tgc tcg ccc tcc tac gtt gcg gtc aca ccc ttc       240
```

-continued

| | | | | | | | | | | | | | | | | |
|---|---|---|---|---|---|---|---|---|---|---|---|---|---|---|---|---|
| | Arg | Arg | Ser | Gly | Leu | Cys | Ser | Pro | Ser | Tyr | Val | Ala | Val | Thr | Pro | Phe |
| | 65 | | | | 70 | | | | 75 | | | | | 80 | | |

| tcc | ctt | cgg | gga | gac | aac | gac | ggt | ggc | ggg | agc | ttc | tcc | acg | gcc | | 288 |
|---|---|---|---|---|---|---|---|---|---|---|---|---|---|---|---|---|
| Ser | Leu | Arg | Gly | Asp | Asn | Asp | Gly | Gly | Gly | Ser | Phe | Ser | Thr | Ala | | |
| | | | | 85 | | | | | 90 | | | | | 95 | | |

| gac | cag | ctg | gag | atg | gtg | acc | gag | ctg | ctg | gga | gga | gac | atg | gtg | aac | 336 |
|---|---|---|---|---|---|---|---|---|---|---|---|---|---|---|---|---|
| Asp | Gln | Leu | Glu | Met | Val | Thr | Glu | Leu | Leu | Gly | Gly | Asp | Met | Val | Asn | |
| | | | 100 | | | | | 105 | | | | | 110 | | | |

| cag | agt | ttc | atc | tgc | gac | ccg | gac | gac | gag | acc | ttc | atc | aag | aac | atc | 384 |
|---|---|---|---|---|---|---|---|---|---|---|---|---|---|---|---|---|
| Gln | Ser | Phe | Ile | Cys | Asp | Pro | Asp | Asp | Glu | Thr | Phe | Ile | Lys | Asn | Ile | |
| | | | 115 | | | | | 120 | | | | | 125 | | | |

| atc | atc | cag | gac | tgt | atg | tgg | agc | ggc | ttc | tcg | gcc | gcc | gcc | aag | ctc | 432 |
|---|---|---|---|---|---|---|---|---|---|---|---|---|---|---|---|---|
| Ile | Ile | Gln | Asp | Cys | Met | Trp | Ser | Gly | Phe | Ser | Ala | Ala | Ala | Lys | Leu | |
| | | 130 | | | | | 135 | | | | | 140 | | | | |

| gtc | tca | gag | aag | ctg | gcc | tcc | tac | cag | gct | gcg | cgc | aaa | gac | agc | ggc | 480 |
|---|---|---|---|---|---|---|---|---|---|---|---|---|---|---|---|---|
| Val | Ser | Glu | Lys | Leu | Ala | Ser | Tyr | Gln | Ala | Ala | Arg | Lys | Asp | Ser | Gly | |
| 145 | | | | | 150 | | | | | 155 | | | | | 160 | |

| agc | ccg | aac | ccc | gcc | cgc | ggc | cac | agc | gtc | tgc | tcc | acc | tcc | agc | ttg | 528 |
|---|---|---|---|---|---|---|---|---|---|---|---|---|---|---|---|---|
| Ser | Pro | Asn | Pro | Ala | Arg | Gly | His | Ser | Val | Cys | Ser | Thr | Ser | Ser | Leu | |
| | | | | 165 | | | | | 170 | | | | | 175 | | |

| tac | ctg | cag | gat | ctg | agc | gcc | gcc | gcc | tca | gag | tgc | atc | gac | ccc | tcg | 576 |
|---|---|---|---|---|---|---|---|---|---|---|---|---|---|---|---|---|
| Tyr | Leu | Gln | Asp | Leu | Ser | Ala | Ala | Ala | Ser | Glu | Cys | Ile | Asp | Pro | Ser | |
| | | | 180 | | | | | 185 | | | | | 190 | | | |

| gtg | gtc | ttc | ccc | tac | cct | ctc | aac | gac | agc | agc | tcg | ccc | aag | tcc | tgc | 624 |
|---|---|---|---|---|---|---|---|---|---|---|---|---|---|---|---|---|
| Val | Val | Phe | Pro | Tyr | Pro | Leu | Asn | Asp | Ser | Ser | Ser | Pro | Lys | Ser | Cys | |
| | | 195 | | | | | 200 | | | | | 205 | | | | |

| gcc | tcg | caa | gac | tcc | agc | gcc | ttc | tct | ccg | tcc | tcg | gat | tct | ctg | ctc | 672 |
|---|---|---|---|---|---|---|---|---|---|---|---|---|---|---|---|---|
| Ala | Ser | Gln | Asp | Ser | Ser | Ala | Phe | Ser | Pro | Ser | Ser | Asp | Ser | Leu | Leu | |
| 210 | | | | | 215 | | | | | 220 | | | | | | |

| tcc | tcg | acg | gag | tcc | tcc | ccg | cag | ggc | agc | ccc | gag | ccc | ctg | gtg | ctc | 720 |
|---|---|---|---|---|---|---|---|---|---|---|---|---|---|---|---|---|
| Ser | Ser | Thr | Glu | Ser | Ser | Pro | Gln | Gly | Ser | Pro | Glu | Pro | Leu | Val | Leu | |
| 225 | | | | | 230 | | | | | 235 | | | | | 240 | |

| cat | gag | gag | aca | ccg | ccc | acc | acc | agc | agc | gac | tct | gag | gag | gaa | caa | 768 |
|---|---|---|---|---|---|---|---|---|---|---|---|---|---|---|---|---|
| His | Glu | Glu | Thr | Pro | Pro | Thr | Thr | Ser | Ser | Asp | Ser | Glu | Glu | Glu | Gln | |
| | | | 245 | | | | | 250 | | | | | 255 | | | |

| gaa | gat | gag | gaa | gaa | atc | gat | gtt | gtt | tct | gtg | gaa | aag | agg | cag | gct | 816 |
|---|---|---|---|---|---|---|---|---|---|---|---|---|---|---|---|---|
| Glu | Asp | Glu | Glu | Glu | Ile | Asp | Val | Val | Ser | Val | Glu | Lys | Arg | Gln | Ala | |
| | | 260 | | | | | 265 | | | | | 270 | | | | |

| cct | ggc | aaa | agg | tca | gag | tct | gga | tca | cct | tct | gct | gga | ggc | cac | agc | 864 |
|---|---|---|---|---|---|---|---|---|---|---|---|---|---|---|---|---|
| Pro | Gly | Lys | Arg | Ser | Glu | Ser | Gly | Ser | Pro | Ser | Ala | Gly | Gly | His | Ser | |
| | | 275 | | | | | 280 | | | | | 285 | | | | |

| aaa | cct | cct | cac | agc | cca | ctg | gtc | ctc | aag | agg | tgc | cac | gtc | tcc | aca | 912 |
|---|---|---|---|---|---|---|---|---|---|---|---|---|---|---|---|---|
| Lys | Pro | Pro | His | Ser | Pro | Leu | Val | Leu | Lys | Arg | Cys | His | Val | Ser | Thr | |
| | 290 | | | | | 295 | | | | | 300 | | | | | |

| cat | cag | cac | aac | tac | gca | gcg | cct | ccc | tcc | act | cgg | aag | gac | tat | cct | 960 |
|---|---|---|---|---|---|---|---|---|---|---|---|---|---|---|---|---|
| His | Gln | His | Asn | Tyr | Ala | Ala | Pro | Pro | Ser | Thr | Arg | Lys | Asp | Tyr | Pro | |
| 305 | | | | 310 | | | | | 315 | | | | | 320 | | |

| gct | gcc | aag | agg | gtc | aag | ttg | gac | agt | gtc | aga | gtc | ctg | aga | cag | atc | 1008 |
|---|---|---|---|---|---|---|---|---|---|---|---|---|---|---|---|---|
| Ala | Ala | Lys | Arg | Val | Lys | Leu | Asp | Ser | Val | Arg | Val | Leu | Arg | Gln | Ile | |
| | | | 325 | | | | | 330 | | | | | 335 | | | |

| agc | aac | aac | cga | aaa | tgc | acc | agc | ccc | agg | tcc | tcg | gac | acc | gag | gag | 1056 |
|---|---|---|---|---|---|---|---|---|---|---|---|---|---|---|---|---|
| Ser | Asn | Asn | Arg | Lys | Cys | Thr | Ser | Pro | Arg | Ser | Ser | Asp | Thr | Glu | Glu | |
| | | 340 | | | | | 345 | | | | | 350 | | | | |

| aat | gtc | aag | agg | cga | aca | cac | aac | gtc | ttg | gag | cgc | cag | agg | agg | aac | 1104 |
|---|---|---|---|---|---|---|---|---|---|---|---|---|---|---|---|---|
| Asn | Val | Lys | Arg | Arg | Thr | His | Asn | Val | Leu | Glu | Arg | Gln | Arg | Arg | Asn | |
| | | 355 | | | | | 360 | | | | | 365 | | | | |

| gag | cta | aaa | cgg | agc | ttc | ttc | gcc | ctg | cgt | gac | cag | atc | ccg | gag | ttg | 1152 |
|---|---|---|---|---|---|---|---|---|---|---|---|---|---|---|---|---|
| Glu | Leu | Lys | Arg | Ser | Phe | Phe | Ala | Leu | Arg | Asp | Gln | Ile | Pro | Glu | Leu | |
| | 370 | | | | | 375 | | | | | 380 | | | | | |

```
                                               -continued gaa aac aat gaa aag gcc ccc aag gta gtt atc ctt aag aag gcc aca    1200
Glu Asn Asn Glu Lys Ala Pro Lys Val Val Ile Leu Lys Lys Ala Thr
385                 390                 395                 400 gca tac atc ctg tcc gtc caa gca gag gag caa aag ctc att tct gaa    1248
Ala Tyr Ile Leu Ser Val Gln Ala Glu Glu Gln Lys Leu Ile Ser Glu
                405                 410                 415 gag gac ttg ttg cgg aaa cga cga gaa cag ttg aaa cac aaa ctt gaa    1296
Glu Asp Leu Leu Arg Lys Arg Arg Glu Gln Leu Lys His Lys Leu Glu
            420                 425                 430 cag cta cgg aac tct tgt gcg                                        1317
Gln Leu Arg Asn Ser Cys Ala
        435

<210> SEQ ID NO 9
<211> LENGTH: 439
<212> TYPE: PRT
<213> ORGANISM: Artificial sequence
<220> FEATURE:
<223> OTHER INFORMATION: Synthetic Construct

<400> SEQUENCE: 9

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
                20                  25                  30

Gln Gln Gln Gln Gln Ser Glu Leu Gln Pro Pro Ala Pro Ser Glu Asp
            35                  40                  45

Ile Trp Lys Lys Phe Glu Leu Leu Pro Thr Pro Pro Leu Ser Pro Ser
        50                  55                  60

Arg Arg Ser Gly Leu Cys Ser Pro Ser Tyr Val Ala Val Thr Pro Phe
65                  70                  75                  80

Ser Leu Arg Gly Asp Asn Asp Gly Gly Gly Ser Phe Ser Thr Ala
                85                  90                  95

Asp Gln Leu Glu Met Val Thr Glu Leu Leu Gly Gly Asp Met Val Asn
            100                 105                 110

Gln Ser Phe Ile Cys Asp Pro Asp Asp Glu Thr Phe Ile Lys Asn Ile
        115                 120                 125

Ile Ile Gln Asp Cys Met Trp Ser Gly Phe Ser Ala Ala Lys Leu
    130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175

Tyr Leu Gln Asp Leu Ser Ala Ala Ser Glu Cys Ile Asp Pro Ser
            180                 185                 190

Val Val Phe Pro Tyr Pro Leu Asn Asp Ser Ser Pro Lys Ser Cys
        195                 200                 205

Ala Ser Gln Asp Ser Ser Ala Phe Ser Pro Ser Ser Asp Ser Leu Leu
    210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
            260                 265                 270

Pro Gly Lys Arg Ser Glu Ser Gly Ser Pro Ser Ala Gly Gly His Ser
        275                 280                 285
```

```
Lys Pro Pro His Ser Pro Leu Val Leu Lys Arg Cys His Val Ser Thr
    290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
            340                 345                 350

Asn Val Lys Arg Arg Thr His Asn Val Leu Glu Arg Gln Arg Arg Asn
        355                 360                 365

Glu Leu Lys Arg Ser Phe Phe Ala Leu Arg Asp Gln Ile Pro Glu Leu
    370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
            420                 425                 430

Gln Leu Arg Asn Ser Cys Ala
        435

<210> SEQ ID NO 10
<211> LENGTH: 40
<212> TYPE: DNA
<213> ORGANISM: Artificial sequence
<220> FEATURE:
<223> OTHER INFORMATION: artificially synthesized sequence

<400> SEQUENCE: 10
gaaatttcac ctaagcggcc gcaatggcag atatctatag                          40

<210> SEQ ID NO 11
<211> LENGTH: 40
<212> TYPE: DNA
<213> ORGANISM: Artificial sequence
<220> FEATURE:
<223> OTHER INFORMATION: artificially synthesized sequence

<400> SEQUENCE: 11
ctatagatat ctgccattgc ggccgcttag gtgaaatttc                          40

<210> SEQ ID NO 12
<211> LENGTH: 22
<212> TYPE: DNA
<213> ORGANISM: Artificial sequence
<220> FEATURE:
<223> OTHER INFORMATION: artificially synthesized sequence

<400> SEQUENCE: 12
agagaacaag actaaggcta cc                                             22

<210> SEQ ID NO 13
<211> LENGTH: 21
<212> TYPE: DNA
<213> ORGANISM: Artificial sequence
<220> FEATURE:
<223> OTHER INFORMATION: artificially synthesized sequence

<400> SEQUENCE: 13
accttgacaa tcctgatgtg g                                              21
```

```
<210> SEQ ID NO 14
<211> LENGTH: 22
<212> TYPE: DNA
<213> ORGANISM: Artificial sequence
<220> FEATURE:
<223> OTHER INFORMATION: artificially synthesized sequence

<400> SEQUENCE: 14
ccatcaacac tccccaagga cc                                              22

<210> SEQ ID NO 15
<211> LENGTH: 22
<212> TYPE: DNA
<213> ORGANISM: Artificial sequence
<220> FEATURE:
<223> OTHER INFORMATION: artificially synthesized sequence

<400> SEQUENCE: 15
agacgtgatg cgtttgaggc cc                                              22
```